(12) United States Patent
Johnson et al.

(10) Patent No.: US 7,968,310 B2
(45) Date of Patent: Jun. 28, 2011

(54) TAGGED SIALYLTRANSFERASE PROTEINS

(75) Inventors: Karl Johnson, Hatboro, PA (US);
Aliakbar Mobasseri, Voorhees, NJ (US); Xiaomei Bai, San Diego, CA (US); Kyle Kinealy, Plymouth Meeting, PA (US)

(73) Assignee: BioGeneriX AG, Mannheim (DE)

( * ) Notice: Subject to any disclaimer, the term of this patent is extended or adjusted under 35 U.S.C. 154(b) by 0 days.

(21) Appl. No.: 12/162,952

(22) PCT Filed: Feb. 1, 2007

(86) PCT No.: PCT/US2007/002878
§ 371 (c)(1),
(2), (4) Date: Dec. 5, 2008

(87) PCT Pub. No.: WO2007/089923
PCT Pub. Date: Aug. 9, 2007

(65) Prior Publication Data
US 2009/0186377 A1 Jul. 23, 2009

Related U.S. Application Data

(60) Provisional application No. 60/764,499, filed on Feb. 1, 2006, provisional application No. 60/764,625, filed on Feb. 1, 2006, provisional application No. 60/774,088, filed on Feb. 15, 2006, provisional application No. 60/773,941, filed on Feb. 15, 2006.

(51) Int. Cl.
*C12P 21/06* (2006.01)
(52) U.S. Cl. ....... 435/68.1; 435/193; 530/350; 536/23.2
(58) Field of Classification Search .................. None
See application file for complete search history.

(56) References Cited

U.S. PATENT DOCUMENTS

| | | | |
|---|---|---|---|
| 6,096,529 A | 8/2000 | Gilbert et al. | |
| 6,210,933 B1 | 4/2001 | Gilbert et al. | |
| 6,503,744 B1 * | 1/2003 | Gilbert et al. | 435/193 |
| 6,689,604 B1 | 2/2004 | Gilbert et al. | |
| 6,699,705 B2 | 3/2004 | Gilbert et al. | |

FOREIGN PATENT DOCUMENTS

| WO | WO 2005/051327 | 6/2005 |
|---|---|---|
| WO | WO 2006/029538 | 3/2006 |

OTHER PUBLICATIONS

Wells, Biochemistry, vol. 29, pp. 8509-8517, 1990.*
Seffernick et al. (J. Bacteriology, vol. 183, pp. 2405-2410, 2001).*
Chiu et al., "Structural analysis of the sialyltransferase CstII from *Campylobacter jejuni* in complex with a substrate analog," *Nat. Struct. Mol. Biol.* 11:163-170 (2004).
Gilbert et al., "Biosynthesis of ganglioside mimics in *Campylobacter jejuni* OH4384. Identification of the glycosyltransferase genes, enzymatic synthesis of model compounds, and characterization of nanomole amounts by 600-mhz $^1$h and $^{13}$c NMR analysis," *J. Biol. Chem.* 275:3896-3906 (2000).
Gilbert et al., "The genetic bases for the variation in the lipo-oligosaccharide of the musocal pathogen, *Campylobacter jejuni*. Biosynthesis of sialylated ganglioside mimics in the core oligosaccharide," *J. Biol. Chem.* 277:327-337 (2002).
Hirel et al., "Extent of N-terminal methionine excision from *Escheria coli* proteins is governed by the side-chain length of the penultimate amino acid," *Proc. Natl. Acad. Sci. USA* 86:8247-8251 (1989).
New England BioLabs Datasheet. pMAL Protein Fusion and Purification System. <URL:web.archive.org/web/20040910192107/www. neb.com/nebecomm/products_intl/productE8000.asp> Sep. 10, 2004).
Wakarchuk and Cunningham, "Capillary electrophoresis as an assay method for monitoring glycosyltransferase activity," *Methods Mol. Biol.* 213:263-274 (2003).
Weisgerber et al., "Complete nucleotide and deduced protein sequence of CMP-NeuAc: poly-α-2,8 sialosyl sialyltransferase of *Escherichia coli* K1," *Glycobiol.* 1:357-365 (1991).
Hyung, Kim Gu et al., High-level expression of human glycosyltransferase in insect cells as biochemically active form. Biochem. and Biophysical Research Communications. 2003, pp. 488-493, vol. 305.
Hidari, Kazuya I.P.J., Purification and characterization of a soluble recombinant human ST6Gal I functionally expressed in *Escherichia coli*, Glycoconjugate J.. 2005. pp. 1-11, vol. 22.

* cited by examiner

*Primary Examiner* — Hope A Robinson
(74) *Attorney, Agent, or Firm* — Leydig, Voit & Mayer, Ltd.

(57) ABSTRACT

The present invention provides modified *Campylobacter* sialyltransferase proteins that exhibit enhanced expression as compared to its unmodified form. Nucleic acids that encode the sialyltransferase proteins are also included, as are methods to produce and use the sialyltransferase proteins.

8 Claims, 44 Drawing Sheets

FIGURE 2

(MGS)MKKVIIAGNGPSLKEIDYSRLPNDFDVFRCNQFYFEDKYYLGKKCKAVFYNPS
LFFEQYYTLKHLIQNQEYETELIMCSNYNQAHLENENFVKTFYDYFPDAHLGYDFFK
QLKDFNAYFKFHEIYFNQRITSGVYMCAVAIALGYKEIYLSGIDFYQNGSSYAFDTKQ
KNLLKLAPNFKNDNSHYIGHSKNTDIKALEFLEKTYKIKLYCLCPNSLLANFIELAPN
LNSNFIIQEKNNYTKDILIPSSEAYGKFSKNINF

Media Components

FIG 3

E1 Media

| Reagent | Concentration |
|---|---|
| Martone B-1 | 10g/L |
| Marcor Yeast Extract | 5g/L |
| Sodium Chloride | 10g/L |
| R.O. Water | As needed |
| PPG 2000 | 1mL/L |
| Phosphoric Acid | As needed to maintain pH=7 |
| Sodium Hydroxide | As needed to maintain pH=7 |

E6 Media

| Reagent | Concentration (g/L) |
|---|---|
| Martone B-1 | 37.5 |
| Marcor Yeast Extract | 19.75 |
| Dextrose | 3.13 |
| Ammonium Phosphate | 3.75 |
| PPG 2000 | 1 |
| Potassium Phosphate, Monobasic | 3.75 |
| Potassium Phosphate, Dibasic | 4.22 |
| Ferrous Sulfate | 0.0205 |
| Magnesium Sulfate, Heptahydrate | 1.01 |
| R.O. Water | As needed |

SEQUENCE LISTING

<160> NUMBER OF SEQ ID NOS: 38

<210> SEQ ID NO 1
<211> LENGTH: 783
<212> TYPE: DNA
<213> ORGANISM: Artificial Sequence
<220> FEATURE:
<223> OTHER INFORMATION: Description of Artificial Sequence:
      Campylobacter jejuni strain OH4384 sialyltransferase II (CST-II)
      insert in expression plasmid vector pNT1

<400> SEQUENCE: 1

```
atgaaaaaag ttattattgc tggaaatgga ccaagtttaa agaaattga ttattcaaga      60 ctaccaaatg attttgatgt atttagatgt aatcaattt attttgaaga taaatactat     120
cttggtaaaa aatgcaaggc agtattttac aatcctagtc ttttttttga acaatactac     180
actttaaaac atttaatcca aaatcaagaa tatgagaccg aactaattat gtgttctaat     240
tacaaccaag ctcatctaga aaatgaaaat tttgtaaaaa cttttacga ttattttcct      300 gatgctcatt tgggatatga ttttttcaaa caacttaaag atttttaatgc ttattttaaa    360 tttcacgaaa tttatttcaa tcaaagaatt acctcagggg tctatatgtg tgcagtagcc     420
atagccctag gatacaaaga aatttatctt tcgggaattg attttttatca aaatgggtca    480 tcttatgctt ttgatactaa acaaaaaaat ctttttaaaat tggctcctaa ttttaaaaat    540
gataattcac actatattgg acatagtaaa aatacagata taaagctttt agaatttcta    600
gaaaaaactt acaaaataaa actatattgc ttatgtccta acagtctttt agcaaatttt    660
atagaactag cgccaaattt aaattcaaat tttatcatac aagaaaaaaa taactacact    720
aaagatatac tcatacctcc tagtgaggct tatggaaaat tttcaaaaaa tattaatttt    780
taa                                                                 783
```

<210> SEQ ID NO 2
<211> LENGTH: 263
<212> TYPE: PRT
<213> ORGANISM: Artificial Sequence
<220> FEATURE:
<223> OTHER INFORMATION: Description of Artificial Sequence:protein
      sequence encoded by Campylobacter jejuni strain
      OH4384 sialyltransferase II (CST-II) insert in
      expression plasmid vector pNT1

<400> SEQUENCE: 2

```
Met Gly Ser Met Lys Lys Val Ile Ile Ala Gly Asn Gly Pro Ser Leu
  1               5                  10                  15

Lys Glu Ile Asp Tyr Ser Arg Leu Pro Asn Asp Phe Asp Val Phe Arg
                 20                  25                  30

Cys Asn Gln Phe Tyr Phe Glu Asp Lys Tyr Tyr Leu Gly Lys Lys Cys
             35                  40                  45

Lys Ala Val Phe Tyr Asn Pro Ser Leu Phe Phe Glu Gln Tyr Tyr Thr
         50                  55                  60

Leu Lys His Leu Ile Gln Asn Gln Glu Tyr Glu Thr Glu Leu Ile Met
 65                  70                  75                  80

Cys Ser Asn Tyr Asn Gln Ala His Leu Glu Asn Glu Asn Phe Val Lys
                 85                  90                  95

Thr Phe Tyr Asp Tyr Phe Pro Asp Ala His Leu Gly Tyr Asp Phe Phe
            100                 105                 110

Lys Gln Leu Lys Asp Phe Asn Ala Tyr Phe Lys Phe His Glu Ile Tyr
        115                 120                 125
```

```
Phe Asn Gln Arg Ile Thr Ser Gly Val Tyr Met Cys Ala Val Ala Ile
    130                 135                 140
Ala Leu Gly Tyr Lys Glu Ile Tyr Leu Ser Gly Ile Asp Phe Tyr Gln
145                 150                 155                 160
Asn Gly Ser Ser Tyr Ala Phe Asp Thr Lys Gln Lys Asn Leu Leu Lys
                165                 170                 175
Leu Ala Pro Asn Phe Lys Asn Asp Asn Ser His Tyr Ile Gly His Ser
            180                 185                 190
Lys Asn Thr Asp Ile Lys Ala Leu Glu Phe Leu Glu Lys Thr Tyr Lys
        195                 200                 205
Ile Lys Leu Tyr Cys Leu Cys Pro Asn Ser Leu Leu Ala Asn Phe Ile
    210                 215                 220
Glu Leu Ala Pro Asn Leu Asn Ser Asn Phe Ile Ile Gln Glu Lys Asn
225                 230                 235                 240
Asn Tyr Thr Lys Asp Ile Leu Ile Pro Ser Ser Glu Ala Tyr Gly Lys
                245                 250                 255
Phe Ser Lys Asn Ile Asn Phe
            260

<210> SEQ ID NO 3
<211> LENGTH: 5807
<212> TYPE: DNA
<213> ORGANISM: Artificial Sequence
<220> FEATURE:
<223> OTHER INFORMATION: Description of Artificial Sequence:expression
      plasmid vector pNT1 including tagged (MGS)
      Campylobacter jejuni strain OH4384
      sialyltransferase II (CST-II)

<400> SEQUENCE: 3
tcgcgctgtt agcgggccca ttaagttctg tctcggcgcg tctgcgtctg gctggctggc    60
ataaatatct cactcgcaat caaattcagc cgatagcgga acgggaaggc gactggagtg   120
ccatgtccgg ttttcaacaa accatgcaaa tgctgaatga gggcatcgtt cccactgcga   180
tgctggttgc caacgatcag atggcgctgg gcgcaatgcg cgccattacc gagtccgggc   240
tgcgcgttgg tgcggatatc tcggtagtgg gatacgacga taccgaagac agctcatgtt   300
atatcccgcc gttaaccacc atcaaacagg attttcgcct gctggggcaa accagcgtgg   360
accgcttgct gcaactctct cagggccagg cggtgaaggg caatcagctg ttgcccgtct   420
cactggtgaa agaaaaaacc accctggcgc ccaatacgca aaccgcctct ccccgcgcgt   480
tggccgattc attaatgcag ctggcacgac aggtttcccg actggaaagc gggcagtgag   540
cgcaacgcaa ttaatgtaag ttagctcact cattaggcac cccaggcttt acactttatg   600
cttccggctc gtatggcgtt tcggtgatga cggtgaaaac tctgacaca tgcagctccc    660
ggagacggtc acagcttgtc tgtaagcgga tgccgggagc agacaagccc gtcagggcgc   720
gtcagcgggt gttggcgggt gtcggggcgc agccatgacc cagtcacgta gcgatagcgg   780
agtgtatact ggcttaacta tgcggcatca gagcagattg tactgagagt gcaccattat   840
gcggtgtgaa ataccgcaca gatgcgtaag gagaaaatac cgcatcaggc gctcttccgc   900
ttcctcgctc actgactcgc tgcgctcggt cgttcggctg cggcgagcgg tatcagctca   960
ctcaaaggcg gtaatacggt tatccacaga atcaggggat aacgcaggaa agaacatgtg  1020
agcaaaaggc cagcaaaagg ccaggaaccg taaaaaggcc gcgttgctgg cgttttccca  1080
taggctccgc cccctgacg agcatcacaa aatcgacgc tcaagtcaga ggtggcgaaa    1140
cccgacagga ctataaagat accaggcgtt tccccctgga agctccctcg tgcgctctcc  1200
```

```
tgttccgacc ctgccgctta ccggatacct gtccgccttt ctcccttcgg aagcgtggc    1260 gctttctcat agctcacgct gtaggtatct cagttcggtg taggtcgttc gctccaagct    1320
gggctgtgtg cacgaacccc ccgttcagcc cgaccgctgc gccttatccg gtaactatcg    1380
tcttgagtcc aacccggtaa gacacgactt atcgccactg gcagcagcca ctggtaacag    1440
gattagcaga gcgaggtatg taggcggtgc tacagagttc ttgaagtggt ggcctaacta    1500
cggctacact agaaggacag tatttggtat ctgcgctctg ctgaagccag ttaccttcgg    1560
aaaaagagtt ggtagctctt gatccggcaa acaaaccacc gctggtagcg gtggtttttt    1620
tgtttgcaag cagcagatta cgcgcagaaa aaaggatctc aagaagatcc tttgatcttt    1680 tctacgggg tctgacgctc agtggaacga aaactcacgt taagggattt tggtcatgag    1740
attatcaaaa aggatcttca cctagatcct tttaaattaa aaatgaagtt ttaaatcaat    1800
ctaaagtata tatgagtaaa cttggtctga cagttaccaa tgcttaatca gtgaggcacc    1860
tatctcagcg atctgtctat ttcgttcatc catagttgcc tgactccccg tcgtgtagat    1920
aactacgata cgggagggct taccatctgg ccccagtgct gcaatgatac cgcgagaccc    1980
acgctcaccg gctccagatt tatcagcaat aaaccagcca gccggaaggg ccgagcgcag    2040
aagtggtcct gcaactttat ccgcctccat ccagtctatt aattgttgcc gggaagctag    2100
agtaagtagt tcgccagtta atagtttgcg caacgttgtt gccattgctg caggcatcgt    2160
ggtgtcacgc tcgtcgtttg gtatggcttc attcagctcc ggttcccaac gatcaaggcg    2220
agttacatga tcccccatgt tgtgcaaaaa agcggttagc tccttcggtc ctccgatcgg    2280 ggggggggg aaagccacgt tgtgtctcaa atctctgat gttacattgc acaagataaa    2340
aatatatcat catgaacaat aaaactgtct gcttacataa acagtaatac aagggggtgtt    2400 atgagccata ttcaacggga acgtcttgc tccaggccgc gattaaattc caacatggat    2460 gctgattat atgggtataa atgggctcgc gataatgtcg gcaatcagg tgcgacaatc    2520 tatcgactgt atgggaagcc cgatgcgcca gagttgtttc tgaaacatgg caaaggtagc    2580
gttgccaatg atgttacaga tgagatggtc agactaaact ggctgacgga atttatgcct    2640
cttccgacca tcaagcattt tatccgtact cctgatgatg catggttact caccactgcg    2700
atccccggga aaacagcatt ccaggtatta agaatatc ctgattcagg tgaaaatatt    2760
gttgatgcgc tggcagtgtt cctgcgccgg ttgcattcga ttcctgtttg taattgtcct    2820
tttaacagcg atcgcgtatt tcgtctcgct caggcgcaat cacgaatgaa taacggtttg    2880
gttgatgcga gtgattttga tgacgagcgt aatggctggc ctgttgaaca gtctggaaa    2940 gaaatgcata agctattgcc attctcaccg gattcagtcg tcactcatgg tgatttctca    3000
cttgataacc ttatttttga cgaggggaaa ttaataggtt gtattgatgt tggacgagtc    3060
ggaatcgcag accgatacca ggatcttgcc atcctatgga actgcctcgg tgagttttct    3120
ccttcattac agaaacggct ttttcaaaaa tatggtattg ataatcctga tatgaataaa    3180
ttgcagtttc atttgatgct cgatgagttt ttctaaagta ctactcttcc ttttcaata    3240 ttattgaagc atttatcagg gttattgtct catgagcgga tacatatttg aatgtattta    3300
gaaaaataaa caataggggg ttccgcgcac atttccccga aaagtgccac ctgacgatga    3360
aattgtaaac gttaatatt tgttaaaatt cgcgttaaat tttgttaaa tcagctcatt    3420 ttttaaccaa taggccgaaa tcggcaaaat cccttataaa tcaaaagaat agcccgagat    3480
agggttgagt gttgttccag tttggaacaa gagtccacta ttaaagaacg tggactccaa    3540
cgtcaagggg cgaaaaaccg tctatcaggg cgatggccca ctacgtgaac catcacccaa    3600
```

```
atcaagttttt tggggtcga ggtgccgtaa agctctaaat cggaaccta aagggagccc    3660
ccgatttaga gcttgacggg gaaagccggc gaacgtggcg agaaaggaag ggaagaaagc    3720
gaaaggagcg ggcgctaggg cgctggcaag tgtagcggtc acgctgcgcg taaccaccac    3780
acccgccgcg cttaatgcgc cgctacaggg cgcgtactat ggttgctttg acgcatcgtc    3840
taagaaacca ttattatcat gacattaacc tataaaaata ggcgtatcac gaggcccttt    3900
cgtcttcaag cagatctgaa aaaaagcccg ctcattagg cgggctcaga tctgctcatg    3960
tttgacagct tatcatcgat gtcgacggta ccgaattcct cgagctatta aaattaata    4020
tttttttgaaa attttccata agcctcacta gaaggtatga gtatatcttt agtgtagtta    4080
tttttttctt gtatgataaa atttgaattt aaatttggcg ctagttctat aaaatttgct    4140
aaaagactgt taggacataa gcaatatagt tttatttgt aagttttttc tagaaattct    4200
aaagctttta tatctgtatt tttactatgt ccaatatagt gtgaattatc attttttaaaa    4260
ttaggagcca attttaaaag attttttgt ttagtatcaa aagcataaga tgacccattt    4320
tgataaaaat caattcccga aagataaatt tctttgtatc ctagggctat ggctactgca    4380
cacatataga cccctgaggt aattctttga ttgaaataaa tttcgtgaaa tttaaaataa    4440
gcattaaaat ctttaagttg tttgaaaaaa tcatatccca aatgagcatc aggaaaataa    4500
tcgtaaaaag tttttacaaa attttcattt tctagatgag cttggttgta attgaaacac    4560
ataattagtt cggtctcata ttcttgattt tggattaaat gttttaaagt gtagtattgt    4620
tcaaaaaaaa gactaggatt gtaaaatact gccttgcatt ttttaccaag atagtattta    4680
tcttcaaaat aaaattgatt acatctaaat acatcaaaat catttggtag tcttgaataa    4740
tcaatttctt ttaaacttgg tccatttcca gcaataataa cttttttcat ggatcccata    4800
tgacctccta agcatcgata gatcctgttt cctgtgtgaa attgttatcc gctcacaatt    4860
ccacacatta tacgagccga tgattaattg tcaacagggg gatggggagt aagctgatcc    4920
tgtttcctgt gtgaaattgt tatccgctca caattccaca cattatacga gccgatgatt    4980
aattgtcaac aggggggatgg ggagtaagct catcgatgga tcgatcctgt ttcctgtgtg    5040
aaattgttat ccgctcacaa ttccacacat tatacgagcc ggaagcataa agtgtaaagc    5100
ctggggtgcc taatgagtga gctaacttac attaattgcg ttgcgctcac tgcccgcttt    5160
ccagtcggga aacctgtcgt gccaggacac catcgaatgg tgcaaaacct ttcgcggtat    5220
ggcatgatag cgcccggaag agagtcaatt cagggtggtg aatgtgaaac cagtaacgtt    5280
atacgatgtc gcagagtatg ccggtgtctc ttatcagacc gtttcccgcg tggtgaacca    5340
ggccagccac gtttctgcga aaacgcggga aaaagtggaa gcggcgatgg cggagctgaa    5400
ttacattccc aaccgcgtgg cacaacaact ggcgggcaaa cagtcgttgc tgattggcgt    5460
tgccacctcc agtctggccc tgcacgcgcc gtcgcaaatt gtcgcggcga ttaaatctcg    5520
cgccgatcaa ctgggtgcca gcgtggtggt gtcgatggta gaacgaagcg cgtcgaagc    5580
ctgtaaagcg gcggtgcaca atcttctcgc gcaacgcgtc agtgggctga tcattaacta    5640
tccgctggat gaccaggatg ccattgctgt ggaagctgcc tgcactaatg ttccggcgtt    5700
atttcttgat gtctctgacc agacacccat caacagtatt attttctccc atgaagacgg    5760
tacgcgactg ggcgtggagc atctggtcgc attgggtcac cagcaaa                 5807
```

<210> SEQ ID NO 4
<211> LENGTH: 291
<212> TYPE: PRT
<213> ORGANISM: Campylobacter jejuni

```
<220> FEATURE:
<223> OTHER INFORMATION: native Campylobacter jejuni strain OH4384
      sialyltransferase II (CST-II)

<400> SEQUENCE: 4

Met Lys Lys Val Ile Ile Ala Gly Asn Gly Pro Ser Leu Lys Glu Ile
1               5                   10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ile Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 5
<211> LENGTH: 260
<212> TYPE: PRT
<213> ORGANISM: Artificial Sequence
<220> FEATURE:
<223> OTHER INFORMATION: Description of Artificial Sequence:
      Campylobacter jejuni strain OH4384 sialyltransferase II (CST-II)
      amino aids 1-260 with Ile53Ser mutation

<400> SEQUENCE: 5

Met Lys Lys Val Ile Ile Ala Gly Asn Gly Pro Ser Leu Lys Glu Ile
1               5                   10                  15

Asp Tyr Ser Arg Leu Pro Asn Asp Phe Asp Val Phe Arg Cys Asn Gln
            20                  25                  30
```

Phe Tyr Phe Glu Asp Lys Tyr Tyr Leu Gly Lys Lys Cys Lys Ala Val
            35                  40                  45

Phe Tyr Asn Pro Ser Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Lys Gln Leu
            100                 105                 110

Lys Asp Phe Asn Ala Tyr Phe Lys Phe His Glu Ile Tyr Phe Asn Gln
            115                 120                 125

Arg Ile Thr Ser Gly Val Tyr Met Cys Ala Val Ala Ile Ala Leu Gly
        130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe
            260

<210> SEQ ID NO 6
<211> LENGTH: 291
<212> TYPE: PRT
<213> ORGANISM: Campylobacter jejuni
<220> FEATURE:
<223> OTHER INFORMATION: Campylobacter jejuni strain OH4382
      sialyltransferase II (CST-II)

<400> SEQUENCE: 6

Met Lys Lys Val Ile Ile Ala Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
            35                  40                  45

Phe Tyr Asn Pro Ile Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Lys Gln Leu
            100                 105                 110

Lys Asp Phe Asn Ala Tyr Phe Lys Phe His Glu Ile Tyr Phe Asn Gln
            115                 120                 125

```
Arg Ile Thr Ser Gly Val Tyr Met Cys Ala Val Ala Ile Ala Leu Gly
        130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Lys Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 7
<211> LENGTH: 291
<212> TYPE: PRT
<213> ORGANISM: Campylobacter jejuni
<220> FEATURE:
<223> OTHER INFORMATION: Campylobacter jejuni strain HB93-13
      sialyltransferase II (CST-II)

<400> SEQUENCE: 7

Met Lys Lys Val Ile Ile Ala Gly Asn Gly Pro Ser Leu Lys Glu Ile
  1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ile Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Phe Lys Gln Leu
            100                 105                 110

Lys Asp Phe Asn Ala Tyr Phe Lys Phe His Glu Ile Tyr Phe Asn Gln
        115                 120                 125

Arg Ile Thr Ser Gly Val Tyr Met Cys Ala Val Ala Ile Ala Leu Gly
    130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190
```

```
Asp Ile Lys Ala Leu Glu Phe Leu Glu Lys Thr Tyr Lys Ile Lys Leu
            195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
            245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
            275                 280                 285

Lys Gly Lys
        290

<210> SEQ ID NO 8
<211> LENGTH: 291
<212> TYPE: PRT
<213> ORGANISM: Campylobacter jejuni
<220> FEATURE:
<223> OTHER INFORMATION: Campylobacter jejuni strain O:10 ATCC 43438
      sialyltransferase II (CST-II)

<400> SEQUENCE: 8

Met Lys Lys Val Ile Ile Ser Gly Asn Gly Pro Ser Leu Lys Glu Ile
  1               5                  10                  15

Asp Tyr Ser Arg Leu Pro Asn Asp Phe Asp Val Phe Arg Cys Asn Gln
             20                  25                  30

Phe Tyr Phe Glu Asp Lys Tyr Tyr Leu Gly Lys Lys Phe Lys Ala Val
         35                  40                  45

Phe Tyr Asn Pro Gly Leu Phe Phe Glu Gln Tyr Tyr Thr Leu Lys His
     50                  55                  60

Leu Ile Gln Asn Gln Glu Tyr Glu Thr Glu Leu Ile Met Cys Ser Asn
 65                  70                  75                  80

Tyr Asn Gln Ala His Leu Glu Asn Glu Asn Phe Val Lys Thr Phe Tyr
             85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Leu Asn Gln
        115                 120                 125

Arg Ile Thr Ser Gly Val Tyr Met Cys Ala Val Ala Ile Ala Leu Gly
130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Glu Asn Leu Leu Lys Leu Ala Pro
            165                 170                 175

Asp Phe Lys Asn Asp Arg Ser His Tyr Ile Gly His Ser Lys Asn Thr
            180                 185                 190

Asp Ile Lys Ala Leu Glu Phe Leu Glu Lys Thr Tyr Lys Ile Lys Leu
            195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Ser Lys
            245                 250                 255
```

```
Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 9
<211> LENGTH: 291
<212> TYPE: PRT
<213> ORGANISM: Campylobacter jejuni
<220> FEATURE:
<223> OTHER INFORMATION: Campylobacter jejuni strain O:23 ATCC 43449
      sialyltransferase II (CST-II)

<400> SEQUENCE: 9

Met Lys Lys Val Ile Ile Ser Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ser Leu Phe Phe Glu Gln Tyr Tyr Thr Leu Lys His
    50                  55                  60

Leu Ile Gln Asn Gln Glu Tyr Glu Ile Glu Leu Ile Met Cys Ser Asn
65                  70                  75                  80

Tyr Asn Gln Ala His Leu Glu Asn Glu Asn Phe Val Lys Thr Phe Tyr
                85                  90                  95

Asp Tyr Phe Pro Asp Ala His Leu Gly Tyr Asp Phe Phe Lys Gln Leu
            100                 105                 110

Lys Glu Phe Asn Ala Tyr Phe Lys Phe His Glu Ile Tyr Phe Asn Gln
        115                 120                 125

Arg Ile Thr Ser Gly Val Tyr Met Cys Thr Val Ala Ile Ala Leu Gly
    130                 135                 140

Tyr Lys Glu Ile Tyr Leu Ser Gly Ile Asp Phe Tyr Asp Asn Gly Gly
145                 150                 155                 160

Gly Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Glu Ile Lys Leu
        195                 200                 205

Tyr Cys Leu Cys Pro Asn Ser Leu Leu Ala Asn Phe Ile Glu Leu Ala
    210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Thr Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Lys Leu Pro Ser Asp Ile Lys His Tyr Phe
        275                 280                 285

Lys Gly Lys
    290

<210> SEQ ID NO 10
```

```
<211> LENGTH: 291
<212> TYPE: PRT
<213> ORGANISM: Campylobacter jejuni
<220> FEATURE:
<223> OTHER INFORMATION: Campylobacter jejuni strain O:41 ATCC 43460
      sialyltransferase II (CST-II)

<400> SEQUENCE: 10

Met Lys Lys Val Ile Ile Ser Gly Asn Gly Pro Ser Leu Lys Glu Ile
 1               5                  10                  15

Asp Tyr Ser Arg Leu Pro Asn Asp Phe Asp Val Phe Arg Cys Asn Gln
            20                  25                  30

Phe Tyr Phe Glu Asp Lys Tyr Tyr Leu Gly Lys Lys Cys Lys Ala Val
        35                  40                  45

Phe Tyr Asn Pro Ser Leu Phe Phe Glu Gln Tyr Tyr Thr Leu Lys His
    50                  55                  60

Leu Ile Gln Asn Gln Glu Tyr Glu Thr Glu Leu Ile Met Cys Ser Asn
65                  70                  75                  80

Phe Asn Gln Ala His Leu Glu Asn Gln Asn Phe Val Lys Thr Phe Tyr
                85                  90                  95

Asp Tyr Phe Pro Asp Ala His Leu Gly Tyr Asp Phe Pro Lys Gln Leu
           100                 105                 110

Lys Glu Phe Asn Ala Tyr Phe Lys Phe His Glu Ile Tyr Phe Asn Gln
       115                 120                 125

Arg Ile Thr Ser Gly Val Tyr Met Cys Thr Val Ala Ile Ala Leu Gly
130                 135                 140

Tyr Lys Glu Ile Tyr Leu Ser Gly Ile Asp Phe Tyr Gln Asn Gly Ser
145                 150                 155                 160

Ser Tyr Ala Phe Asp Thr Lys Gln Lys Asn Leu Leu Lys Leu Ala Pro
                165                 170                 175

Asn Phe Lys Asn Asp Asn Ser His Tyr Ile Gly His Ser Lys Asn Thr
            180                 185                 190

Asp Ile Lys Ala Leu Glu Phe Leu Glu Lys Thr Tyr Glu Ile Lys Leu
        195                 200                 205

Tyr Cys Leu Cys Pro Asn Ser Leu Leu Ala Asn Phe Ile Glu Leu Ala
210                 215                 220

Pro Asn Leu Asn Ser Asn Phe Ile Ile Gln Glu Lys Asn Asn Tyr Thr
225                 230                 235                 240

Lys Asp Ile Leu Ile Pro Ser Ser Glu Ala Tyr Gly Lys Phe Thr Lys
                245                 250                 255

Asn Ile Asn Phe Lys Lys Ile Lys Ile Lys Glu Asn Ile Tyr Tyr Lys
            260                 265                 270

Leu Ile Lys Asp Leu Leu Arg Leu Pro Ser Asp Ile Lys His Tyr Phe
        275                 280                 285

Lys Gly Lys
    290

<210> SEQ ID NO 11
<211> LENGTH: 12
<212> TYPE: PRT
<213> ORGANISM: Artificial Sequence
<220> FEATURE:
<223> OTHER INFORMATION: Description of Artificial
      Sequence:sialyltransferase motif A
<220> FEATURE:
<221> NAME/KEY: MOD_RES
<222> LOCATION: (12)
<223> OTHER INFORMATION: Xaa = Asp or Glu

<400> SEQUENCE: 11
```

```
Asp Val Phe Arg Cys Asn Gln Phe Tyr Phe Glu Xaa
 1               5                   10
```

```
<210> SEQ ID NO 12
<211> LENGTH: 9
<212> TYPE: PRT
<213> ORGANISM: Artificial Sequence
<220> FEATURE:
<223> OTHER INFORMATION: Description of Artificial
      Sequence:sialyltransferase motif B

<400> SEQUENCE: 12

Arg Ile Thr Ser Gly Val Tyr Met Cys
 1               5
```

```
<210> SEQ ID NO 13
<211> LENGTH: 12
<212> TYPE: PRT
<213> ORGANISM: Artificial Sequence
<220> FEATURE:
<223> OTHER INFORMATION: Description of Artificial
      Sequence:sialyltransferase motif A

<400> SEQUENCE: 13

Asp Val Phe Arg Cys Asn Gln Phe Tyr Phe Glu Asp
 1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: Description of Artificial
      Sequence:sialyltransferase motif A

<400> SEQUENCE: 14

Asp Val Phe Arg Cys Asn Gln Phe Tyr Phe Glu Glu
 1               5                   10
```

```
<210> SEQ ID NO 15
<211> LENGTH: 262
<212> TYPE: PRT
<213> ORGANISM: Artificial Sequence
<220> FEATURE:
<223> OTHER INFORMATION: Description of Artificial Sequence:major
      Campylobacter jejuni sialyltransferase II (CST-II)
      species produced by pNT1 expression plasmid vector

<400> SEQUENCE: 15

Gly Ser Met Lys Lys Val Ile Ile Ala Gly Asn Gly Pro Ser Leu Lys
 1               5                   10                  15

Glu Ile Asp Tyr Ser Arg Leu Pro Asn Asp Phe Asp Val Phe Arg Cys
            20                  25                  30

Asn Gln Phe Tyr Phe Glu Asp Lys Tyr Leu Gly Lys Lys Cys Lys
        35                  40                  45

Ala Val Phe Tyr Asn Pro Ser Leu Phe Phe Glu Gln Tyr Tyr Thr Leu
    50                  55                  60

Lys His Leu Ile Gln Asn Gln Glu Tyr Glu Thr Glu Leu Ile Met Cys
65                  70                  75                  80

Ser Asn Tyr Asn Gln Ala His Leu Glu Asn Glu Asn Phe Val Lys Thr
                85                  90                  95

Phe Tyr Asp Tyr Phe Pro Asp Ala His Leu Gly Tyr Asp Phe Phe Lys
            100                 105                 110

Gln Leu Lys Asp Phe Asn Ala Tyr Phe Lys Phe His Glu Ile Tyr Phe
```

115                 120                 125
Asn Gln Arg Ile Thr Ser Gly Val Tyr Met Cys Ala Val Ala Ile Ala
    130                 135                 140

Leu Gly Tyr Lys Glu Ile Tyr Leu Ser Gly Ile Asp Phe Tyr Gln Asn
145                 150                 155                 160

Gly Ser Ser Tyr Ala Phe Asp Thr Lys Gln Lys Asn Leu Leu Lys Leu
                165                 170                 175

Ala Pro Asn Phe Lys Asn Asp Asn Ser His Tyr Ile Gly His Ser Lys
            180                 185                 190

Asn Thr Asp Ile Lys Ala Leu Glu Phe Leu Glu Lys Thr Tyr Lys Ile
        195                 200                 205

Lys Leu Tyr Cys Leu Cys Pro Asn Ser Leu Leu Ala Asn Phe Ile Glu
    210                 215                 220

Leu Ala Pro Asn Leu Asn Ser Asn Phe Ile Ile Gln Glu Lys Asn Asn
225                 230                 235                 240

Tyr Thr Lys Asp Ile Leu Ile Pro Ser Ser Glu Ala Tyr Gly Lys Phe
                245                 250                 255

Ser Lys Asn Ile Asn Phe
            260

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:N-terminal
      amino acid sequence of CST-II protein in
      expression plasmid vector pNT1

<400> SEQUENCE: 16

Met Gly Ser Met Lys Lys Val
  1               5

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:N-terminal
      nucleic acid sequence of CST-II protein in
      expression plasmid vector pNT1

<400> SEQUENCE: 17
atgggatcca tgaaaaaagt t                                        21

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence:N-terminal
      nucleic acid sequence of CST-II protein in
      expression plasmid vector pNT2

<400> SEQUENCE: 18
catatgaaaa aagtt                                               15

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:FLAG tag
      epitope tag

```
<400> SEQUENCE: 19

Asp Tyr Lys Asp Asp Asp Asp Lys
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:
      hexahistidine peptide affinity tag, (His)-6 tag, 6 His tail, six
      adjacent histidines

<400> SEQUENCE: 20

His His His His His His
 1               5

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence:PCR
      amplification primer CJ18F: 5' for CST-I

<400> SEQUENCE: 21
cttaggaggt catatgacaa ggactagaat ggaaaatgaa c                    41

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence:PCR
      amplification primer CJ40R: 3' with 6 His tail
      for CST-I

<400> SEQUENCE: 22
cctaggtcga ctcattagtg gtgatggtgg tgatgttccc ctttctcaaa ctctctcttc    60

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence:PCR
      amplification primer CJ-131 for CST-II

<400> SEQUENCE: 23
cttaggaggt catatgaaaa aagttattat tgctggaaat g                    41

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence:PCR
      amplification primer CJ-132 for CST-II

<400> SEQUENCE: 24
cctaggtcga cttattttcc tttgaaataa tgctttatat c                    41

<210> SEQ ID NO 25
<211> LENGTH: 33
<212> TYPE: DNA
<213> ORGANISM: Artificial Sequence
<220> FEATURE:
```

```
<223> OTHER INFORMATION: Description of Artificial Sequence:PCR
      amplification primer CstH-5p for CST-III

<400> SEQUENCE: 25 gggggggcata tgagtatgaa tattaatgct ttg                              33

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence:PCR
      amplification primer CstH-3p for CST-III

<400> SEQUENCE: 26
gggggggtcg actcattatc tatttttatt tgcatatttt tc                     42

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer CJ42 for heptosylTase-II in
      LOS locus

<400> SEQUENCE: 27
gccattaccg tatcgcctaa ccagg                                        25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer CJ43 for heptosylTase-I in
      LOS locus

<400> SEQUENCE: 28
aaagaatacg aatttgctaa agagg                                        25

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence of purified CST-II expressed from plasmid
      pNT1

<400> SEQUENCE: 29

Met Gly Ser Met Lys Lys
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:N-terminal
      sequence of purified CST-II expressed from plasmid
      pNT1

<400> SEQUENCE: 30

Gly Ser Met Lys Lys
 1               5

<210> SEQ ID NO 31
```

```
<211> LENGTH: 4
<212> TYPE: PRT
<213> ORGANISM: Artificial Sequence
<220> FEATURE:
<223> OTHER INFORMATION: Description of Artificial Sequence:C-terminal
      sequence of purified CST-II expressed from plasmid
      pNT1

<400> SEQUENCE: 31

Asn Ile Asn Phe
  1

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence of purified CST-II (Major), Band A
      (Major) and Band B (Major)

<400> SEQUENCE: 32

Gly Ser Met Lys Lys Val Ile Ile Ala Gly
  1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence of purified CST-II (Minor) and Band A
      (Minor)

<400> SEQUENCE: 33

Met Lys Lys Val Ile Ile Ala Gly Asn Gly
  1               5                  10

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:N-terminal
      sequence of purified CST-II Band B (Minor)

<400> SEQUENCE: 34

Met Lys Lys Val Ile
  1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence of purified CST-II Band C (Major)
      internal fragment

<400> SEQUENCE: 35

Asn Leu Leu Lys Leu Ala
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence of purified CST-II Band C (Minor)
```

```
        internal fragment

<400> SEQUENCE: 36

Leu Ala Pro Asn Phe Lys
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence of purified CST-II Band C (Minor)
      internal fragment

<400> SEQUENCE: 37

Phe Lys Asn Asp Asn Ser
 1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence:N-terminal
      sequence of purified CST-II expressed from plasmid
      pNT1

<400> SEQUENCE: 38

Gly Ser Met Lys
 1
```

US 7,968,310 B2

TAGGED SIALYLTRANSFERASE PROTEINS

CROSS-REFERENCES TO RELATED APPLICATIONS

This application is a U.S. National Phase Application under 35 U.S.C. §371 of International Application No. PCT/US2007/002878, filed on Feb. 1, 2007, which claims the benefit of U.S. Provisional Application No. 60/764,499, filed Feb. 1, 2006; U.S. Provisional Application No. 60/764,625 filed Feb. 1, 2006; U.S. Provisional Application No. 60/774,088 filed Feb. 15, 2006; U.S. Provisional Application No. 60/773,941 filed Feb. 15, 2006; each of which is herein incorporated by reference for all purposes.

FIELD OF THE INVENTION

The present invention provides modified *Campylobacter* sialyltransferase proteins that exhibit enhanced expression as compared to its unmodified form. Nucleic acids that encode the sialyltransferase proteins are also included, as are methods to produce and use the sialyltransferase proteins.

BACKGROUND OF THE INVENTION

Carbohydrates are now recognized as being of major importance in many cell-cell recognition events, notably the adhesion of bacteria and viruses to mammalian cells in pathogenesis and leukocyte-endothelial cell interaction through selectins in inflammation (Varki (1993) *Glycobiology* 3: 97-130). Moreover, sialylated glycoconjugates that are found in bacteria (Preston et al. (1996) *Crit. Rev. Microbiol.* 22:139-180; Reuter et al. (1996) *Biol. Chem. Hoppe-Seyler* 377:325-342) are thought to mimic oligosaccharides found in mammalian glycolipids to evade the host immune response (Moran et al. (1996) *FEMS Immunol. Med. Microbiol.* 16:105-115). Molecular mimicry of host structures by the saccharide portion of lipopolysaccharide (LPS) is considered to be a virulence factor of various mucosal pathogens, which use this strategy to evade a host immune response (Moran et al. (1996) *FEMS Immunol. Med. Microbiol.* 16: 105-115; Moran et al. (1996) *J. Endotoxin Res.* 3: 521-531).

The oligosaccharide structures involved in these and other processes are potential therapeutic agents, but they are time consuming and expensive to make by traditional chemical means. A very promising route to production of specific oligosaccharide structures is through the use of the enzymes which make them in vivo, the glycosyltransferases. Such enzymes can be used as regio- and stereoselective catalysts for the in vitro synthesis of oligosaccharides (Ichikawa et al. (1992) *Anal. Biochem.* 202: 215-238). Sialyltransferases are a group of glycosyltransferases that transfer sialic acid from an activated sugar nucleotide to acceptor oligosaccharides found on glycoproteins, glycolipids or polysaccharides. The large number of sialylated oligosaccharide structures has led to the characterization of many different sialyltransferases involved in the synthesis of various structures. Sialyltransferases have been isolated and characterized from mammals and other eukaryotes and from microbes, including *C. jeuni, Neisseria, Haemophilus*, and *E. coli*. (Tsuji et al. (1996) *Glycobiology* 6:v-vii; U.S. Pat. Nos. 6,503,744; 6,699,705; 6,096,529; 6,210,933; and Weisgerber et al. (1991) *Glycobiol.* 1:357-365).

Large scale enzymatic synthesis of oligosaccharides depends on the availability of sufficient quantities of the required glycosyltransferases. However, production of glycosyltransferases in sufficient quantities for use in preparing oligosaccharide structures has been problematic. The present invention solves this and other problems.

BRIEF SUMMARY OF THE INVENTION

In one aspect, the present invention provides a tagged sialyltransferase protein that includes an amino acid sequence with 85% identity to SEQ ID NO:4 and an MGS tag at the amino terminus of SEQ ID NO:4. The tagged sialyltransferase protein has sialyltransferase activity. In one embodiment, the tagged sialyltransferase protein, wherein the sialyltransferase polypeptide is a truncated sialyltransferase polypeptide as compared to a naturally occurring form of the sialyltransferase amino acid sequence. In another embodiment, tagged sialyltransferase protein includes an amino acid sequence with 95% identity to SEQ ID NO:4. In another embodiment, the tagged sialyltransferase protein includes an amino acid sequence selected from SEQ ID NO:4, 5, 6, 7, 8, 9, and 10. In a further embodiment, the tagged sialyltransferase protein includes an amino acid sequence that is 95% identical to SEQ ID NO:5. In another embodiment, the tagged sialyltransferase protein includes SEQ ID NO:5.

In another aspect, the present invention provides a nucleic acid that encodes the tagged sialyltransferase protein above. In one embodiment, the invention provides an expression vector that includes the nucleic acid. In another embodiment, the present invention provides an expression vector of SEQ ID NO:3 to express a tagged a tagged sialyltransferase protein. In a further embodiment, the invention provides a host cell that comprises the expression vector.

In another aspect the invention provides a method of making a tagged sialyltransferase protein, by growing the host cell above under conditions suitable for expression of the tagged sialyltransferase protein. The method of making the tagged sialyltransferase protein can also include a step of purifying the tagged sialyltransferase protein.

In another aspect the present invention provides a method of producing a sialylated oligosaccharide product, by contacting an acceptor substrate comprising an oligosaccharide with a tagged-sialyltransferase from above, and a sialic acid donor substrate; and then allowing transfer of the sialic acid from the donor substrate to the acceptor substrate, to produce the sialylated oligosaccharide product. Production of the sialylated oligosaccharide product can occur in vitro or in vivo.

BRIEF DESCRIPTION OF THE DRAWINGS

FIG. 1 provides a restriction map of plasmid pNT1, the pcwin2 vector constructed to express an MGS tagged CSTII protein. The inset shows the N-terminal amino acid and 5' nucleic acid sequences of the CSTII proteins in expression vectors pNT1 (SEQ ID NOS:16-17) and pNT2 (SEQ ID NO:18).

FIG. 2 provides the complete translated amino acid sequence of the CSTII protein expressed from expression vector pNT1 (SEQ ID NO:2). The amino terminal MGS tag is parenthesized.

FIG. 3 provides the components of rich and simple media.

FIG. 4 provides a CST-II Purification Process Scheme.

FIG. 5 provides a Q-SEPHAROSE™ Step Gradient. Column: XK26 Q-SEPHAROSE™ FF resin (40 mL). Equilibration: 5 column columns (CV) 20 mM Tris, pH 8.3 (Buffer A). Load 130 mL clarified homogenate (13 g pellet without EDTA). Column was washed with 5 CV Buffer A. Step gradient elution with Buffer B (1 M NaCl in Buffer A): 4 CV at 15% Buffer B, 4 CV at 25% Buffer B, 4 CV at 50% Buffer B. Flow rate: 115 cm/h. Absorbance at 280 nm Fractions were sampled for SDS-PAGE (FIG. 4) and CST-II enzyme assay. CST-II enzyme activity histogram is plotted on the chromatogram in red. Q-SEPHAROSE™ Elution Fraction 5 pooled for subsequent purification. FT=Flow Through.

Figure 6:
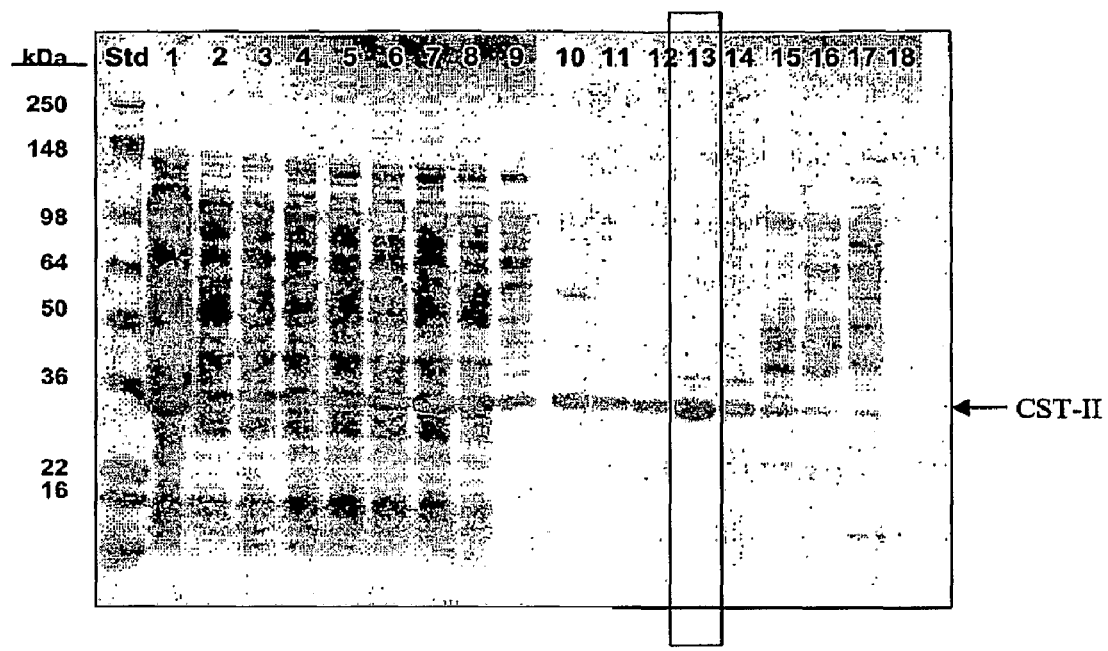

FIG. 6 provides SDS-PAGE Analysis of the Q-SEPHAROSE™ Step Gradient Fractions. Samples of the Q-SEPHAROSE™ fractions from FIG. 3 are shown. Std=SEEBLUE® Plus 2 (15mcL). Lane 1: CST-II Homogenate (10mcL). Lane 2: Flow Through Fraction 1 (10 mcL). Lane 3: Flow Through Fraction 2 (10 mcL). Lane 4: Flow Through Fraction 3 (10 mcL). Lane 5: Flow Through Fraction 4 (10 mcL). Lane 6: Flow Through Fraction 5 (10 mcL). Lane 7: Flow Through Fraction 6 (10 mcL). Lane 8: Flow Through/Wash Pool (22.5 mcL). Lane 9: Elution Fraction 1 (14 mcL). Lane 10: Elution Fraction 2 (2.8 mcL). Lane 11: Elution Fraction 3 (2.4 mcL). Lane 12: Elution Fraction 4 (3 mcL). Lane 13: Elution Fraction 5 (1.5 mcL). Lane 14: Elution Fraction 6 (4.4 mcL). Lane 15: Elution Fraction 7 (4.4 mcL). Lane 16: Elution Fraction 8 (11.8 mcL). Lane 17: Elution Fraction 9 (3 mcL) Lane 18: Elution Fraction 10 (1.8 mcL). 4-20% Tris-glycine SDS PAGE gels were stained by SIMPLYBLUE™ Safe Stain. Q-SEPHAROSE™ Elution Fraction 5 (shown in lane 13) was collected for subsequent purification.

Figure 7:
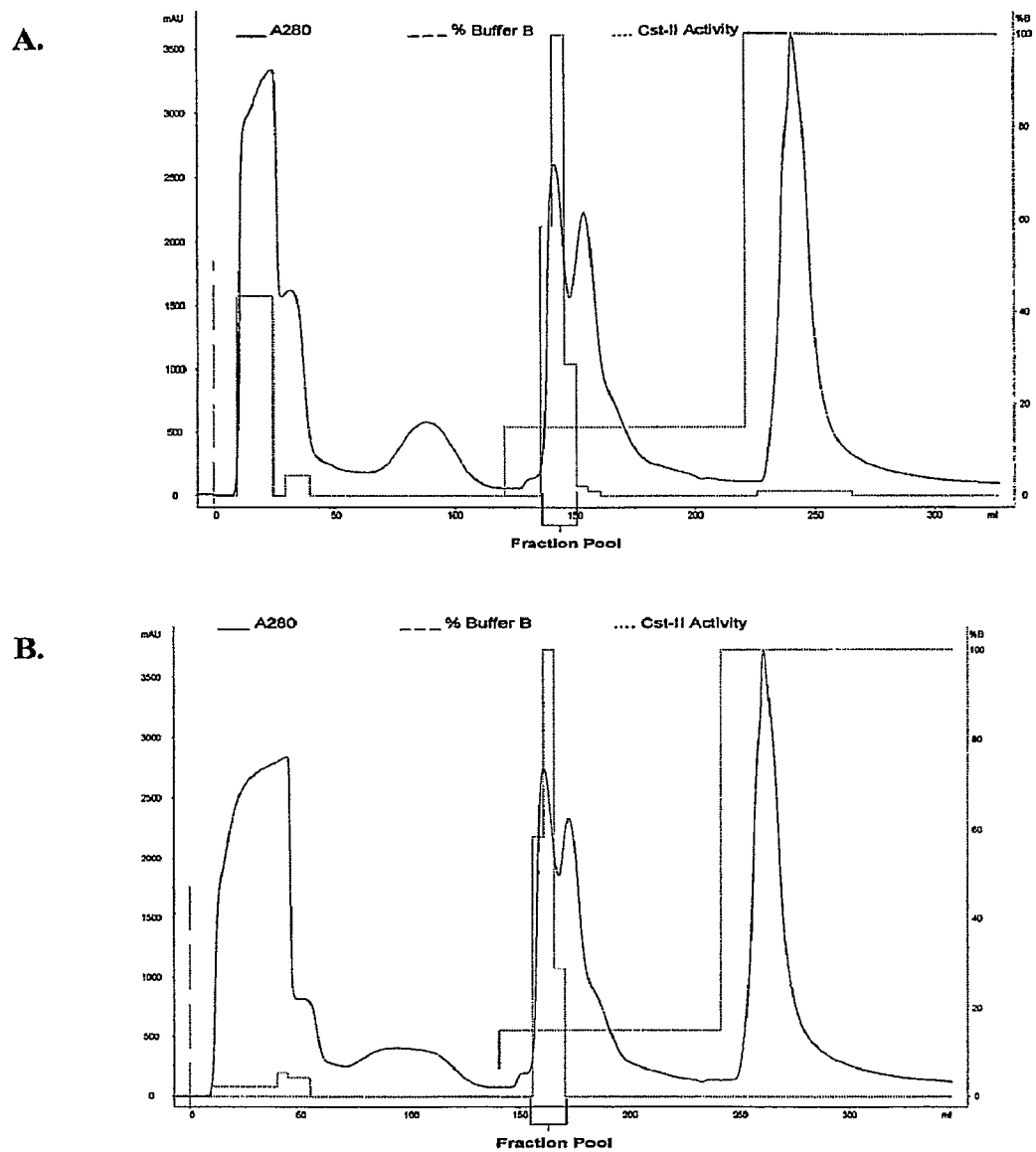

FIG. 7 provides Q-SEPHAROSE™ Step Gradients with and without Dilution of the Loading Solution. Column: XK16 Q-SEPHAROSE™ FF (20 mL). Loaded clarified homogenate (2 g with 5 mM EDTA, 20 mL) FIG. 7A: undiluted, conductivitiy: 4.66 ms/cm. FIG. 7B: diluted 1:1 with Buffer A (50 mM Tris, pH 8.3), conductivity: 3.3 ms/cm. Washed columns with 5 CV Buffer A. Step gradient elution with Buffer B (1 M NaCl jn Buffer A): 5 CV at 15% Buffer B, 5 CV at 100% Buffer B. Flow rate: 115 cm/h. Absorbance at 280 nm. CST-II 20 activity histogram plotted on chromatogram in red. CST-II fractions pooled as indicated.

Figure 8:
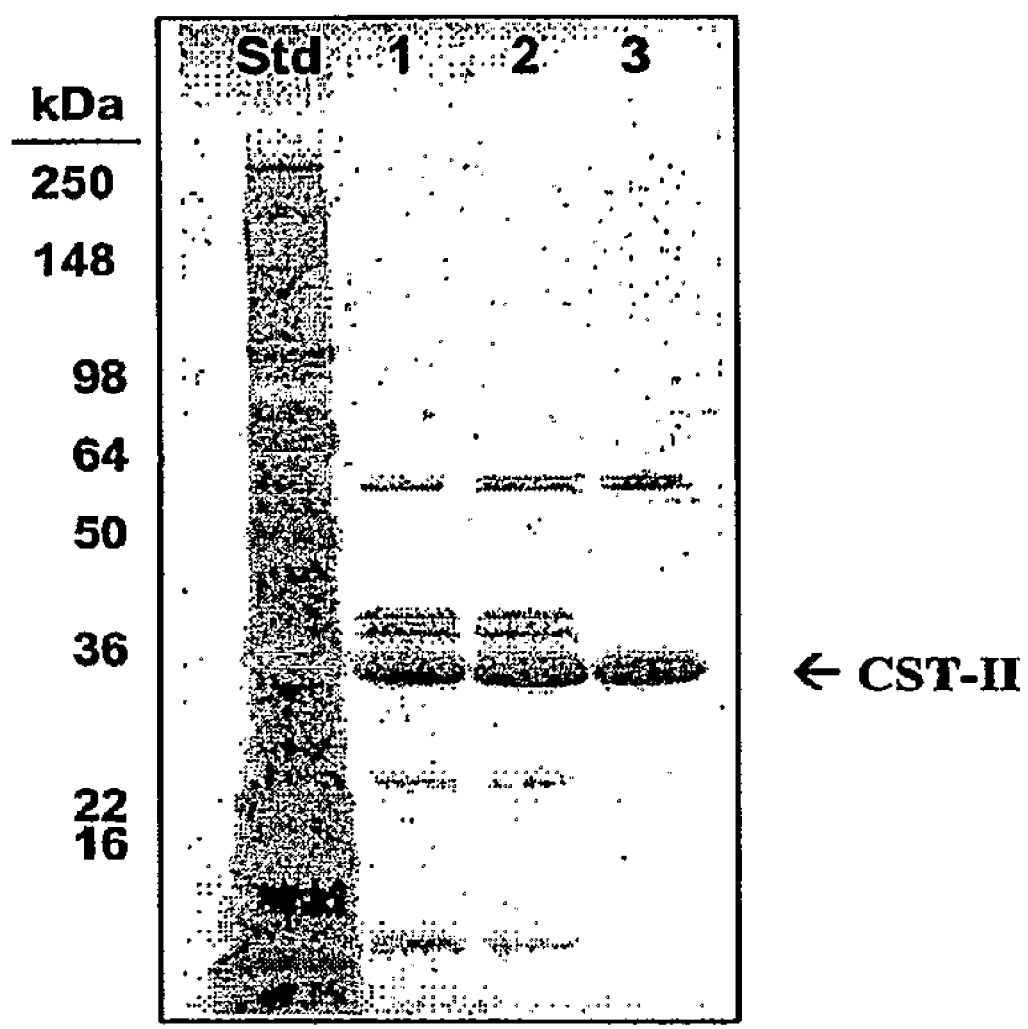

FIG. 8 provides SDS-PAGE Analysis of Pooled Fractions from Q-SEPHAROSE™ Purifications of CST-II. Std=SEEBLUE® Plus 2 (15 mcL). Lane 1: Q-SEPHAROSE™ step gradient fraction pool from undiluted homogenate (FIG. 5A) (10 mcg). Lane 2: Q-SEPHAROSE™ step gradient fraction pool from diluted homogenate (FIG. 5B) (10 mcg). Lane 3: Q-SEPHAROSE· 25 linear gradient fraction pool from diluted homogenate (FIG. 7) (10 mcg). 4-20% Trisglycine SDS PAGE gel was stained by SIMPLYBLUE™ Safe Stain.

Figure 9:
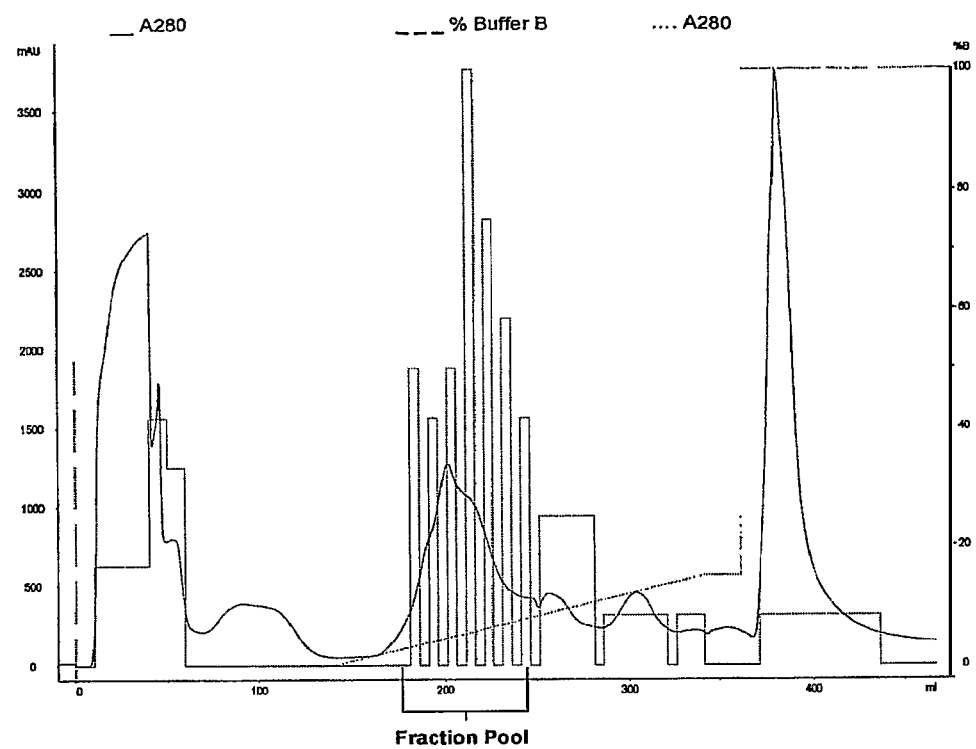

FIG. 9 provides Q-SEPHAROSE™ Linear Gradient Elution. Column: XK16 Q-SEPHAROSE™ FF resin (20 mL). Equilibration: 5 column volumes (CV) 50 mM Tris-HCl, pH 8.3 (Buffer A). Clarified homogenate (2 g pellet with EDTA, 20 mL diluted 1:1 with buffer A, 30 conductivity: 3.3 ms/cm). Washed column with 5 CV Buffer A. Linear elution gradient with Buffer B (1 M NaCl in Buffer A): 0-15% Buffer B over 10 CV followed by 5 CV at 100% Buffer B. Flow rate: 115 cmJh Absorbance at 280 nm. Fractions were pooled as shown. CST-II enzyme activity histogram plotted on chromatogram in red.

Figure 10:
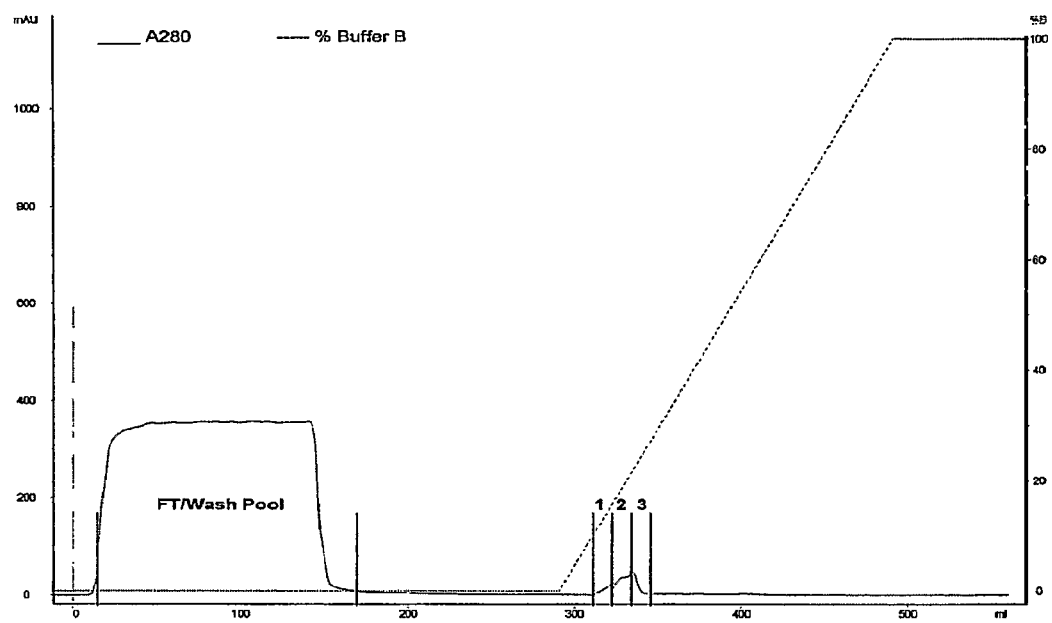

FIG. 10 provides SP-SEPHAROSE™ HP-pH 6.8. Column: XK16 SP-SEPHAROSE™ HP resin (20 mL). Equilibration: 5 column volumes (CV) 25 mM sodium phosphate, pH 6.8 (Buffer A). Purified (Q-SEPHAROSE™ from FIG. 3) CST-II (24 mL) diluted and pH adjusted to 6.5 and 0.2 micron filtered. The conditioned CST-II (µmL, 3.8 ms/cm, A280: 0.855 AU) was loaded. Column was washed with 5 CV buffer A. Elution gradient with Buffer B (1 M NaCl in Buffer A): 0-100% Buffer B over 10 CV. Flow rate: Equilibration, load and wash at 150 cm/hr, Elution at 80 cm/h. Absorbance at 280 nm. Flow through (FT) and Elution Fractions 1-3 were sampled for SDS-PAGE.

Figure 11:
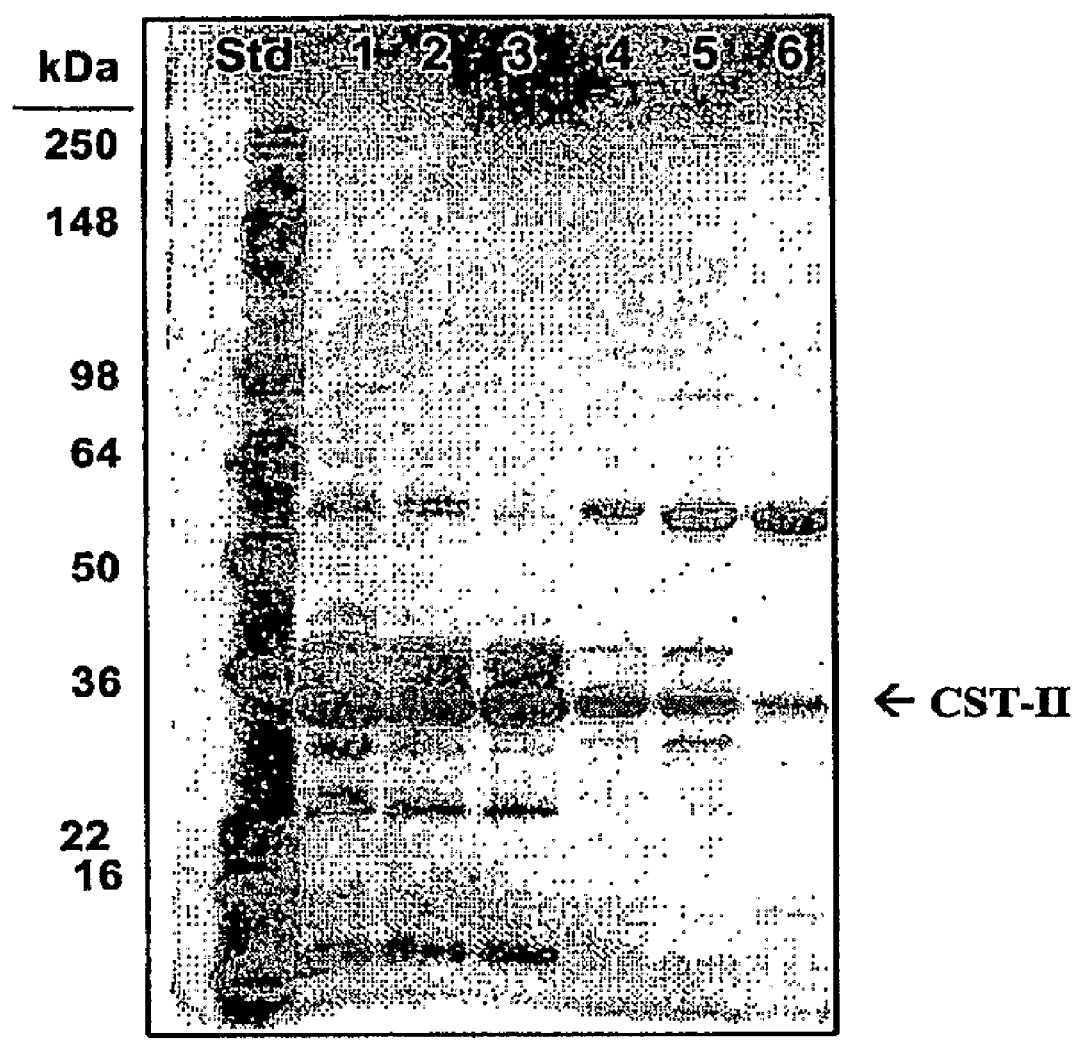

FIG. 11 provides SDS-PAGE Analysis of SP-SEPHAROSE™ HP-pH 6.8 Fractions. Std=SEEBLUE® Plus 2 (15 mcL). Lane 1: CST-II Purified by Q-SEPHAROSE™ (from FIG. 3) (10 mcg). Lane 2: SP-SEPHAROSE™ HP Load (FIG. 8) (19.8 mcL). Lane 3: SP-SEPHAROSE™ HP Flow Through/Wash pool (23.6 mcL). Lane 4: SP-SEPHAROSE™ HP Elution Pool 1 concentrated 13.times.(30 mcL). Lane 5: SP-SEPHAROSE™ HP Elution Pool 2 concentrated 4.8.times.(30 mcL). Lane 6: SP SEPHAROSE™ HP Elution Pool 3 concentrated 3.3.times. (30 mcL). 4-20% Tris-glycine SDS PAGE gel was stained with SIMPLYBLUE™ Safe Stain.

Figure 12:
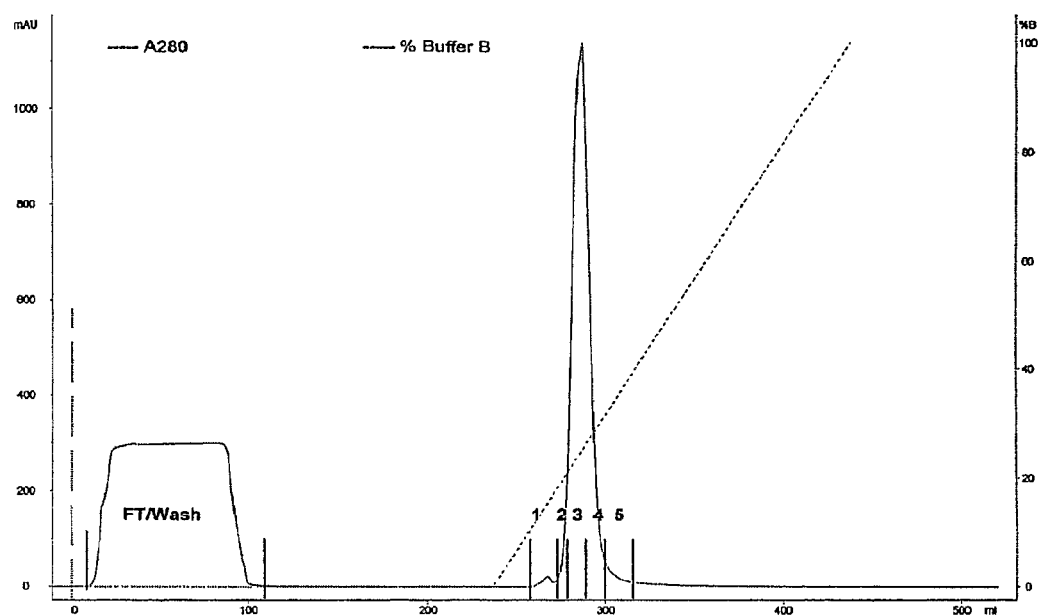

FIG. 12 provides SP-SEPHAROSE™ HP-pH 6.0. Column: XK16 SP-SEPHAROSE™ HP resin (20 mL). Equilibration: 5 column volumes (CV) 25 mM MES, pH 6.0 (Buffer A). Purified (Q-SEPHAROSE™ from FIG. 3) CST-II (20 mL) was diluted, pH adjusted to 6.0 and 0.2 micron filtered. The conditioned CST-II (40 mL, 2.4 ms/cm, A280:1.20 AU) was loaded. The column was washed with 5 CV Buffer A. Elution gradient with Buffer B (1 M NaCl in Buffer A): 0-100% Buffer B over 10 CV. Flow rate: equilibration, load and wash at 150 cm/hr, elution at 80 cm/h. Absorbance at 280 nm. Flow through (FT)/wash and elution fractions 1-5 were sampled for SDS-PAGE (FIG. 11). Fractions 2-5 were pooled for subsequent purification.

Figure 13:
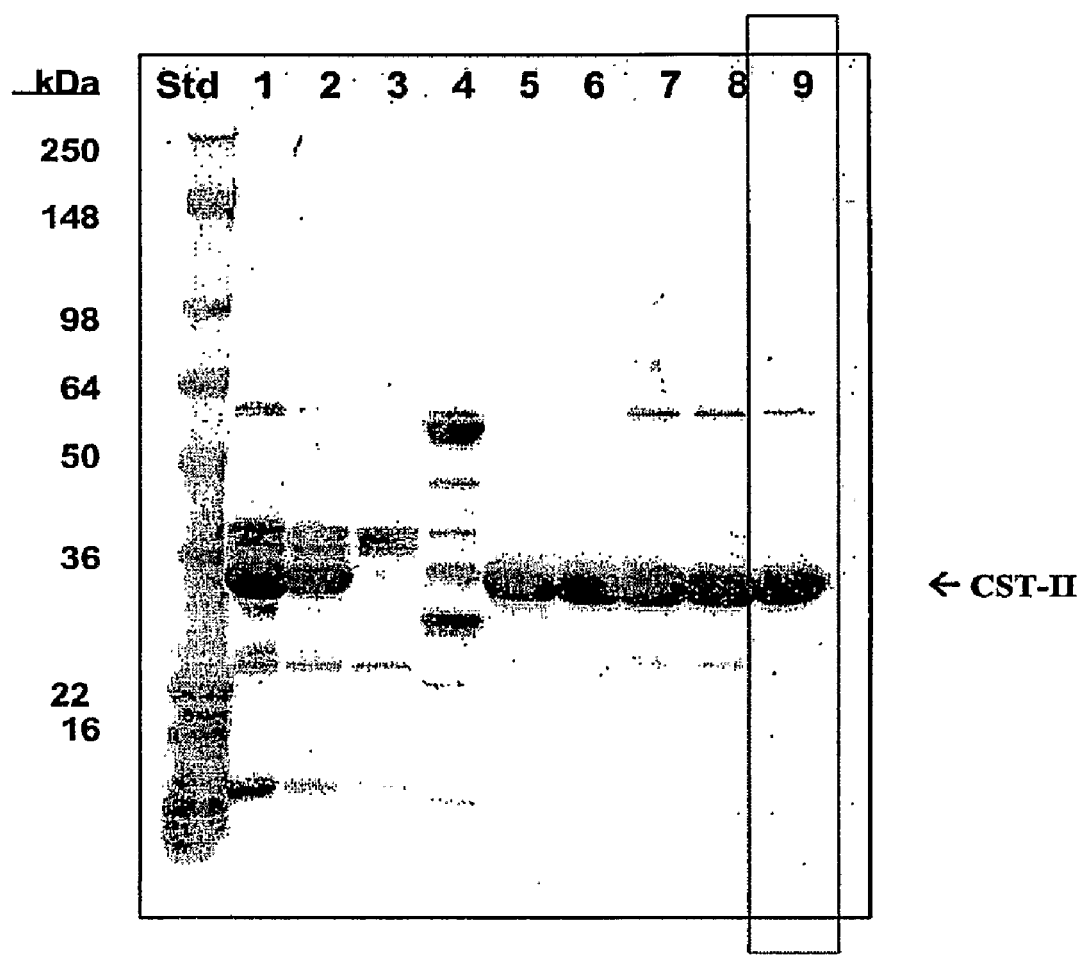

FIG. 13 provides SDS-PAGE Analysis of SP-SEPHAROSE™ HP-pH 6.0 Fractions. Std=SEEBLUE® Plus 2 (15 mcL). Lane 1: CST-II Purified by Q-SEPHAROSE™ (10 mcg). Lane 2: SP-SEPHAROSE™ HP Load (FIG. 10)(10 mcL). Lane 3: SP-SEPHAROSE™ HP Flow Through/Wash pool (30 mcL). Lane 4: SP-SEPHAROSE™ HP Fraction 1 (10 meg). Lane 5: SP-SEPHAROSE™ HP Fraction 2(10 mcg). Lane 6: SP-SEPHAROSE™ HP Fraction 3 (10 mcg). Lane 7: SP-SEPHAROSE™ HP Fraction 4 (10 mcg). Lane 8: SP-SEPHAROSE™ HP Fraction 5 (10 mcg). Lane 9: Elution Pool of SP-SEPHAROSE™ HP Fractions 2-5 (10 mcg). 4-20% Tris-glycine SDS PAGE gel was stained by SIMPLYBLUE™ Safe Stain.

Figure 14:
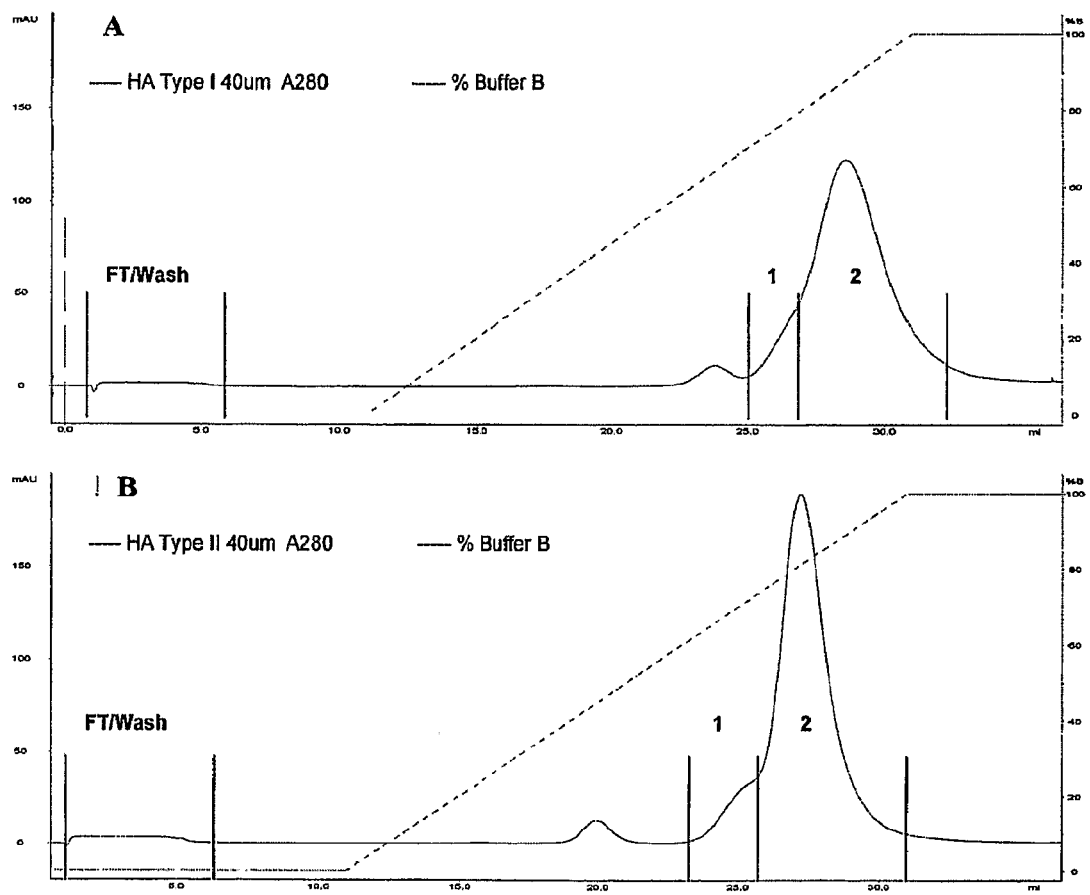

FIG. 14 provides Comparison of Hydroxyapatite Type I and Type II. Column: Tricorn 5 packed with FIG. 14A: Hydroxyapatite Type I (1 mL)-40 micron, FIG. 14B: Hydroxyapatite Type II (1 mL-40 micron). Equilibration: 5 column volumes (CV) 5 mM sodium phosphate, pH 6.5 (Buffer A). CST-II purified by Q-SEPHAROSE™ and SP-SEPHAROSE™ HP (from FIG. 10) (1 mL, 50% glycerol, A280:1.22 AU) was diluted with 5 mM sodium phosphate, pH 6.5 (3 mL) and loaded. Column washed with 10 CV Buffer A. Elution gradient of Buffer B (1.5 M NaCl in Buffer A): from 0-100% B over 20 CV. Flow rate: 153 cm/hr (0.5 mL/min). Absorbance at 280 nm. Flow through (FT)/wash and fraction Pools 1 and 2 were sampled for SDS-PAGE.

Figure 15:
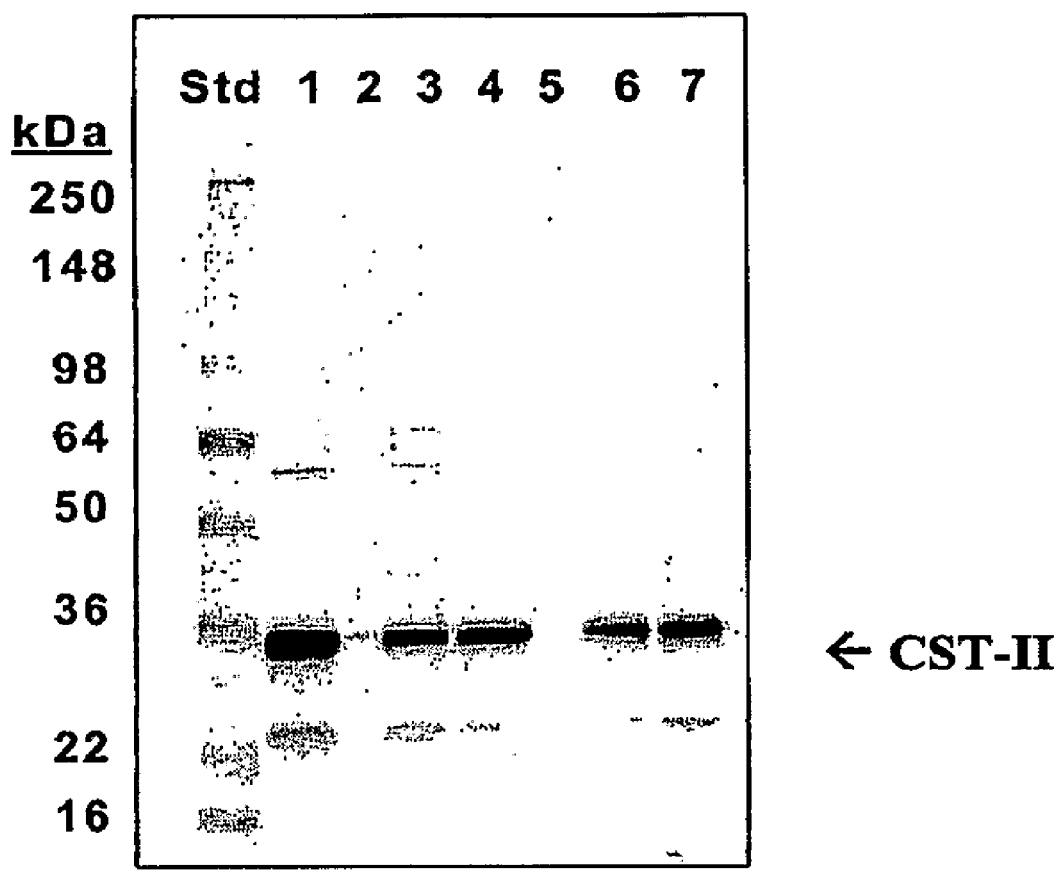

FIG. 15 provides SDS-PAGE Analysis of CST-II Fraction Pools from Hydroxyapatite (HA) Type I and Type II Chromatography (40 micron). Std=SEEBLUE® Plus 2 (1.5 mcL). Lane 1: CST-II purified by Q-SEPHAROSE™ and SP-SEPHAROSE™ HP (FIG. 10) (1.0 mcg). Lane 2: HA Type I Flow Through/Wash pool (20 mcL). Lane 3: HA Type I Elution Pool 1 (1.0 mcg). Lane 4: HA Type I Elution Pool 2 (1.0 mcg). Lane 5: HA Type II Flow Through/Wash Pool (20 mcL). Lane 6: HA Type II Elution Pool 1 (1.0 mcg). Lane 7: HA Type II Elution Pool 2 (1.0 mcg). 4-20% Tris-glycine SDS PAGE gel was stained with Wako Silver Stain kit.

Figure 16:
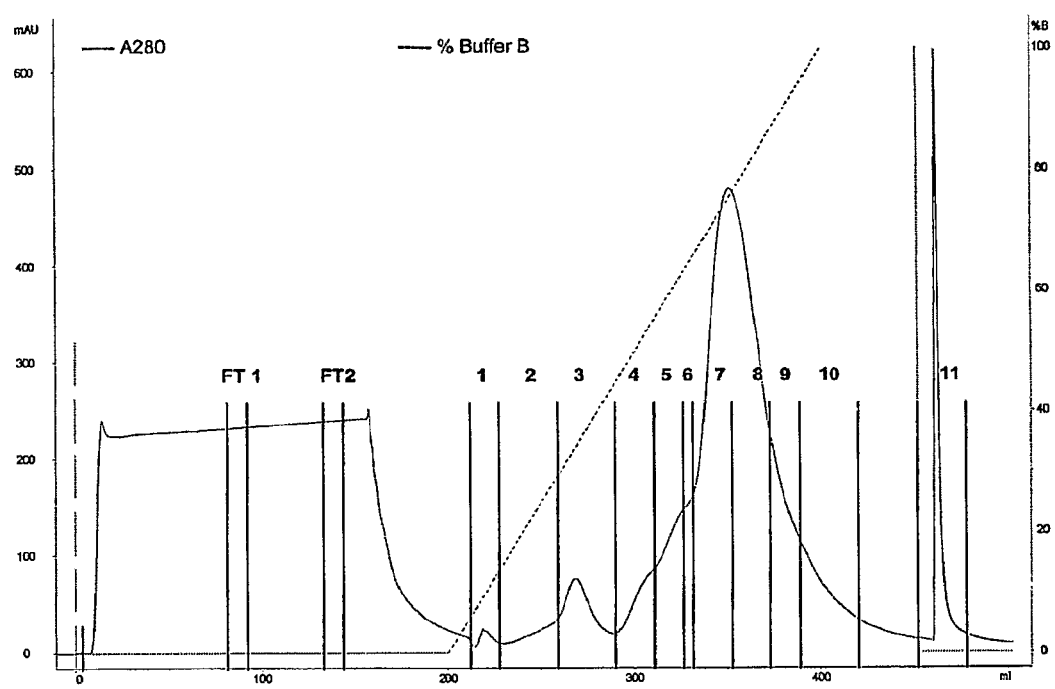

FIG. 16 provides Hydroxyapatite Type II (40 micron) Chromatography-1 mL. Column: XK16 Hydroxyapatite Type 11-40 micron (10 mL). Equilibration: 5 CV 5 mM sodium phosphate, pH 6.5 (Buffer A). CST-II purified by Q-SEPHAROSE™ (30 mL, 50% glycerol, A280:5.56 AU) diluted with 5 mM sodium phosphate, pH 6.5 (120 mL). The pH was adjusted to 6.0 and 0.2 micron filtered. The conditioned CST-II (150 mL, conductivity: 1.65 ms/cm, A280: 1.043 Au) was loaded. Column washed with 5 CV Buffer. Gradient elution with Buffer B (1.5 M NaCl in Buffer A): from 0-100% B over 20 CV, followed by 5 CV of 500 mM sodium phosphate, pH 6.5). Flow rate: 11 g cm/hr (4 mL/min). Absorbance at 280 nm. Fraction Pools were sampled for SDS-PAGE. FT=Flow Through.

Figure 17:
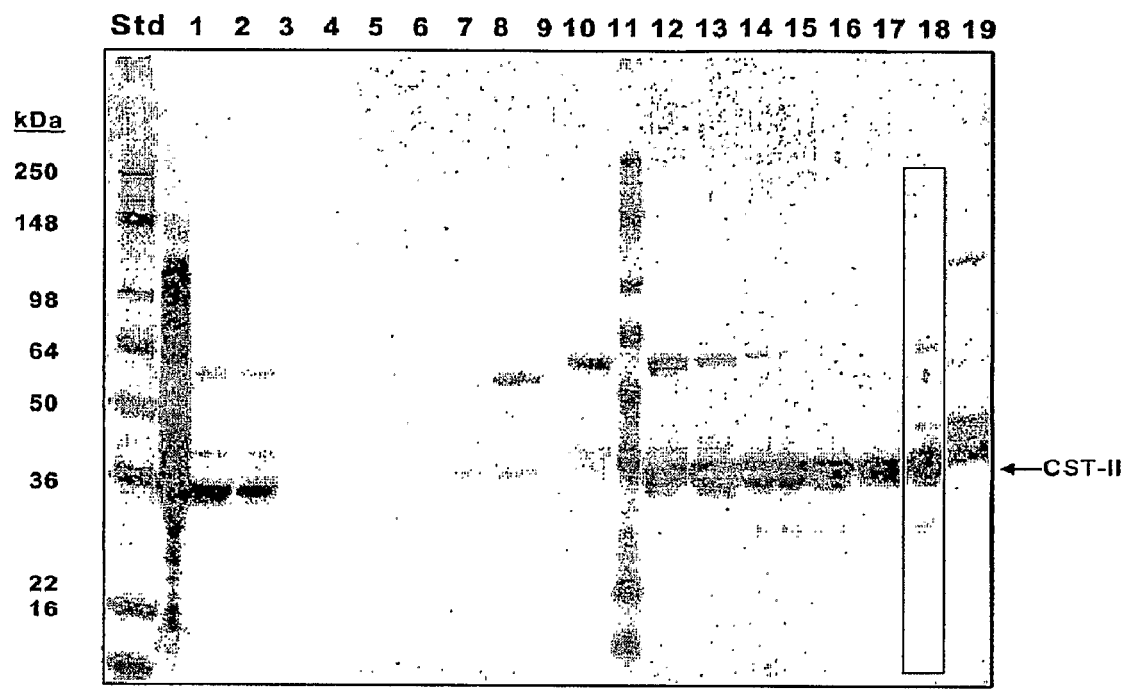

FIG. 17 provides SDS-PAGE Analysis of Hydroxyapatite (HA) Type II (40 micron, 10 mL) Chromatography Fractions. Std=SEEBLUE® Plus 2 (15 mcL). Lane 1: CST-II Homogenate (10 mcL). Lane 2: CST-II purified by Q-SEPHAROSE™ (10 mcg). Lane 3: HA Load (FIG. 14) (10 mcg). Lane 4: HA Flow Through Fraction 1 (10 mcL). Lane 5: HA Flow Through Fraction 2 (10 mcL). Lane 6: HA Flow Through/Wash Pool (12.7 mcL). Lane 7: HA Elution Fraction 1 (20 mcL). Lane 8: HA Elution Fraction 2 (30 mcL). Lane 9: HA Elution Fraction 3 (30 mcL). Lane 10: HA Elution Fraction 4 (30 mcL). Lane 11: SEEBLUE® Plus 2 (15 mcL). Lane 12: HA Elution Fraction 5 (30 mcL). Lane 13: HA Elution Fraction 6 (10 meg). Lane 14: HA Elution Fraction 7 (10 mcg). Lane 15: HA Elution Fraction 8 (10 mcg). Lane 16: HA Elution Fraction 9 (10 mcg). Lane 17: HA Elution Fraction 10 (30 mcL). Lane 18: HA Elution Pool of Fractions 7-9 (10 mcg). Lane 19: HA Elution Fraction 11 (10 mcg). 4-20% Tris-glycine SDS PAGE gels were stained with SIMPLYBLUE™ Safe Stain.

Figure 18:
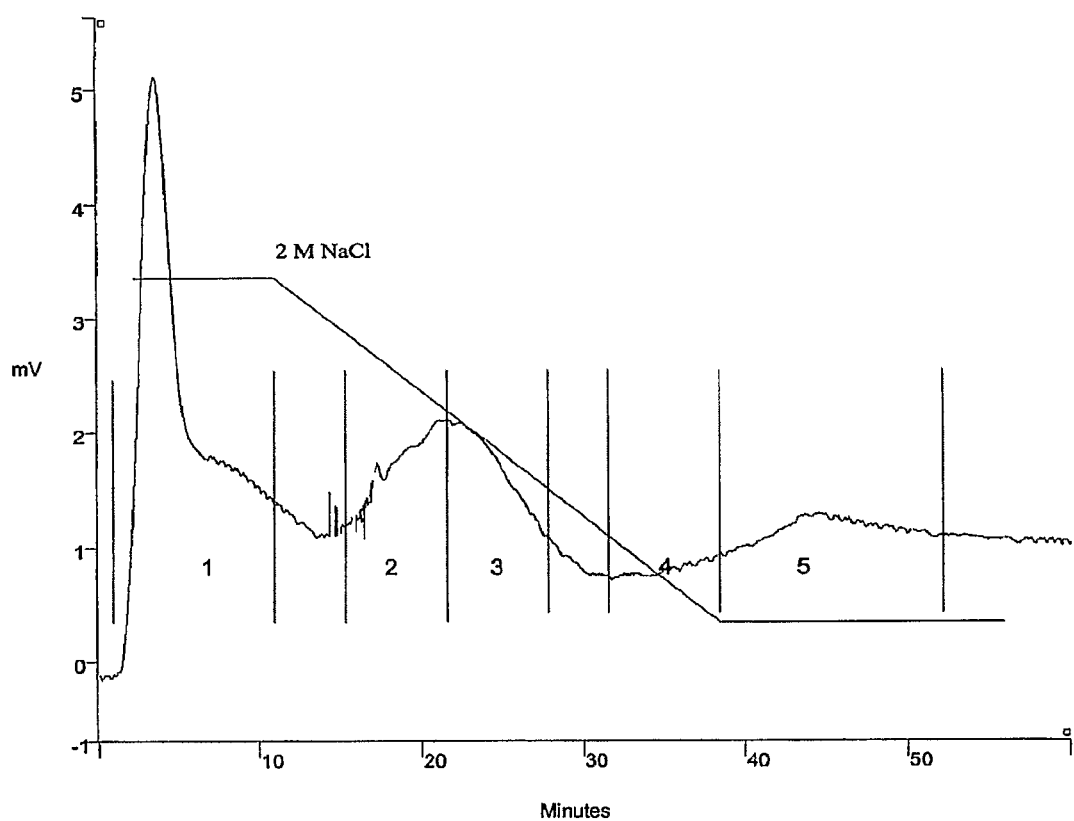

FIG. 18 provides Phenyl SEPHAROSE™ (High Substitution) Chromatography. Column: Phenyl SEPHAROSE™ high sub (1.0 mL). Absorbance at 280 nm. Sample: CST-II purified by Q-SEPHAROSE™ (conditioned in Buffer B: 2 M NaCl 25 mM Tris-HCl, pH 7.2), 1.0 mL, 4.2 mg. Gradient: 0-10 min, 100% B, 10-40 min, 100-0% B; 40-60 min, 100% Buffer A (25 mM Tris-HCl, pH 7.2). Fractions 1-5 were collected and analyzed by SDS-PAGE. Fractions were stored at 4° C.

Figure 19:
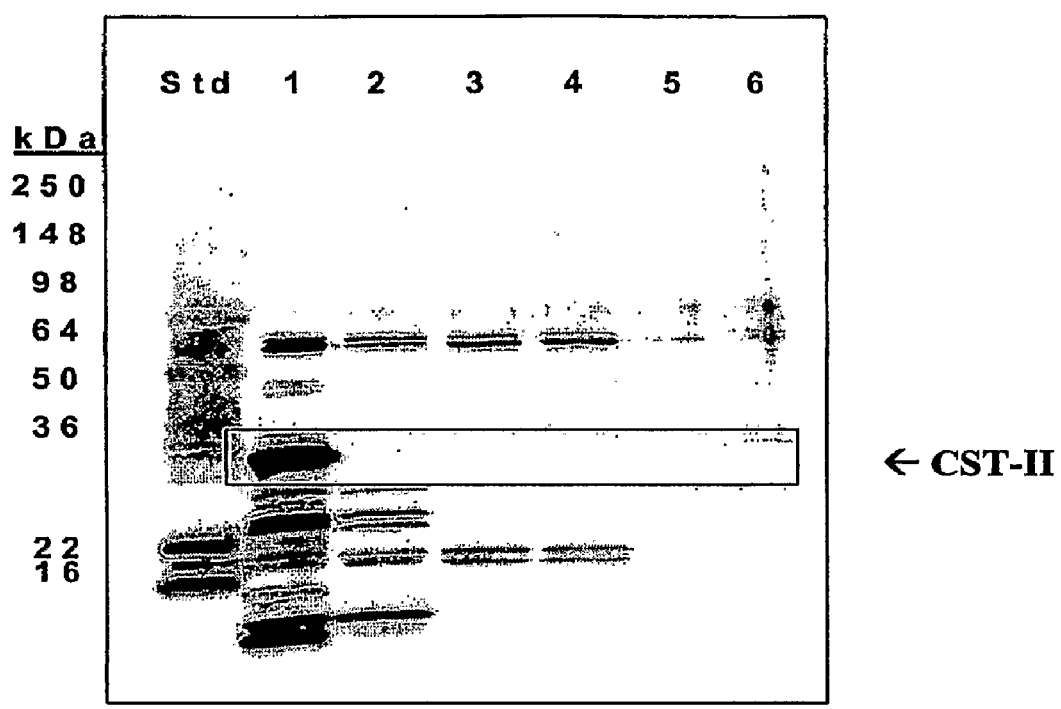

FIG. 19 provides SDS-PAGE Analysis of Phenyl SEPHAROSE™ (High Substitution) Chromatography Fractions. Std=SEEBLUE® Plus 2 (5 mcL). Lane 1: CST-II purified by Q SEPHAROSE™ (10 mcL). Lane 2: Phenyl High Sub Fraction 1 (FIG. 16) (5.0 mcL). Lane 3: Phenyl High Sub Fraction 2 (5.0 mcL). Lane 4: Phenyl High Sub Fraction 3 (5.0 mcL). Lane 5: Phenyl High Sub Fraction 4 (5.0 mcL). Lane 6: Phenyl High Sub Fraction 5 (5.0 mcL). 4-20% Tris-glycine SDS PAGE gel was stained by Wako Silver Stain kit.

Figure 20:
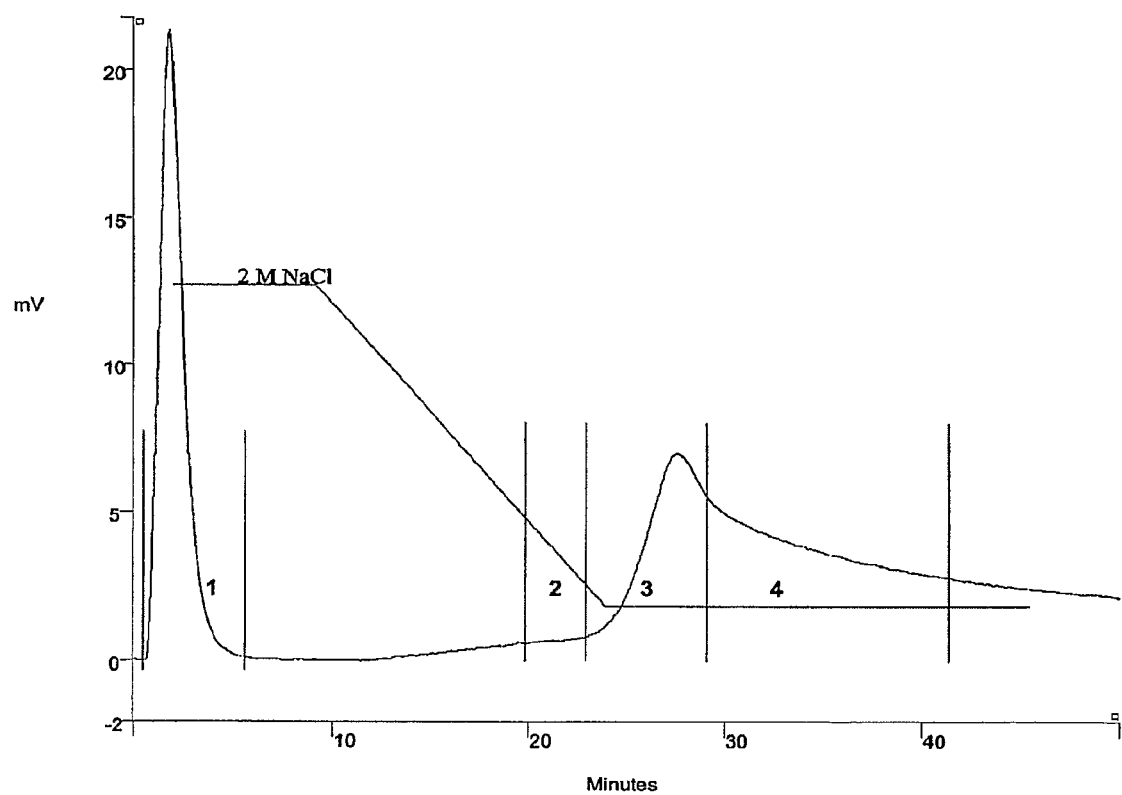

FIG. 20 provides Phenyl SEPHAROSE™ (Low Substitution) Chromatography. Column: Phenyl SEPHAROSE™ low sub (1.0 mL). Absorbance at 280 nm. Sample: CST-II purified by Q-SEPHAROSE™ (conditioned in Buffer B: 2 M NaCl, 25 mM Tris-HCl, pH 7.2), 1.0 mL, 4.2 mg. Gradient: 0-10 min, 100% B, 10-25 min, 100-0% B; 25-50 min, 100% Buffer A (25 mM Tris-HCl, pH 7.2). Fractions 1-4 were collected and analyzed by SDS-PAGE. Fractions were stored at 4° C.

Figure 21:
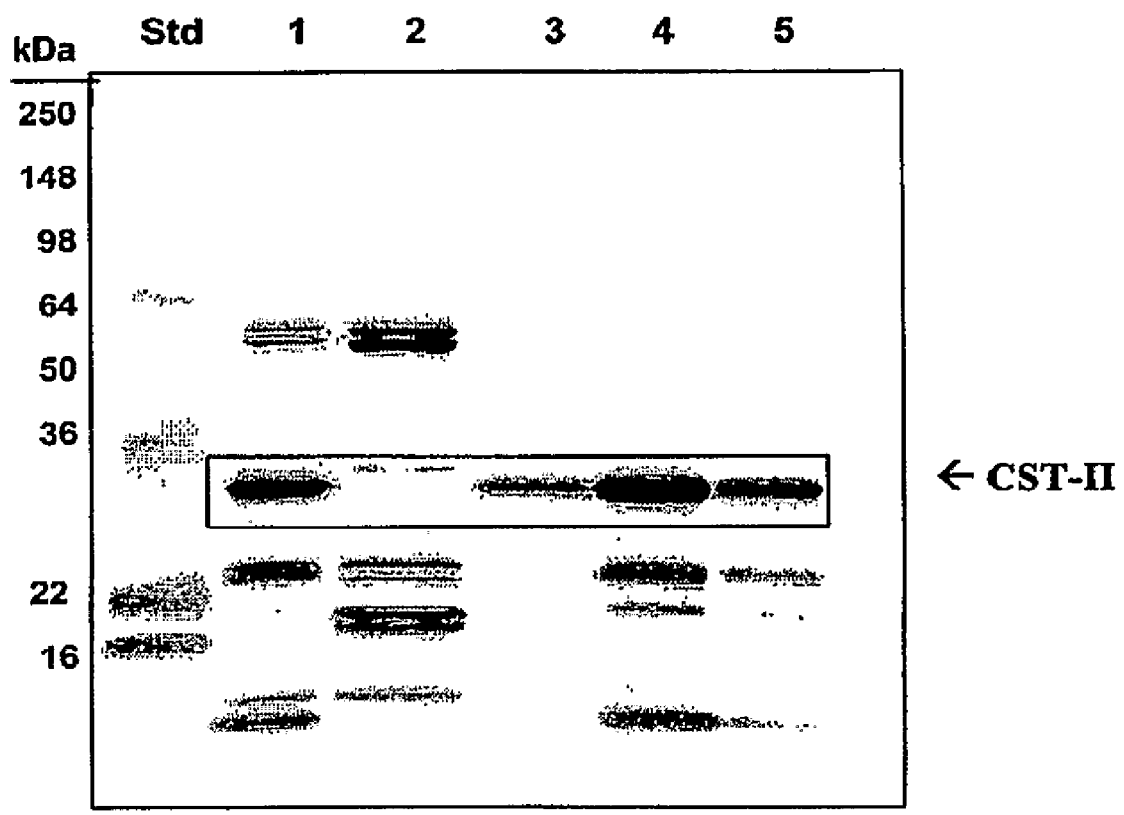

FIG. 21 provides SDS-PAGE Analysis of Phenyl SEPHAROSE™ (Low Substitution) Chromatography Fractions. Std=SEEBLUE® Plus 2 (5 mcL). Lane 1: CST-II Purified by Q SEPHAROSE™ (10 mcL). Lane 2: Phenyl Low Sub Fraction 1 (FIG. 18) (5.0 mcL). Lane 3: Phenyl Low Sub Fraction Fraction 2 (5.0 mcL). Lane 4: Phenyl Low Sub Fraction Fraction 3 (5.0 mcL). Lane 5: Phenyl Low Sub Fraction Fraction 4 (5.0 mcL). 4-20% Tris-glycine SDS PAGE gel was stained with Wako Silver Stain kit.

Figure 22:
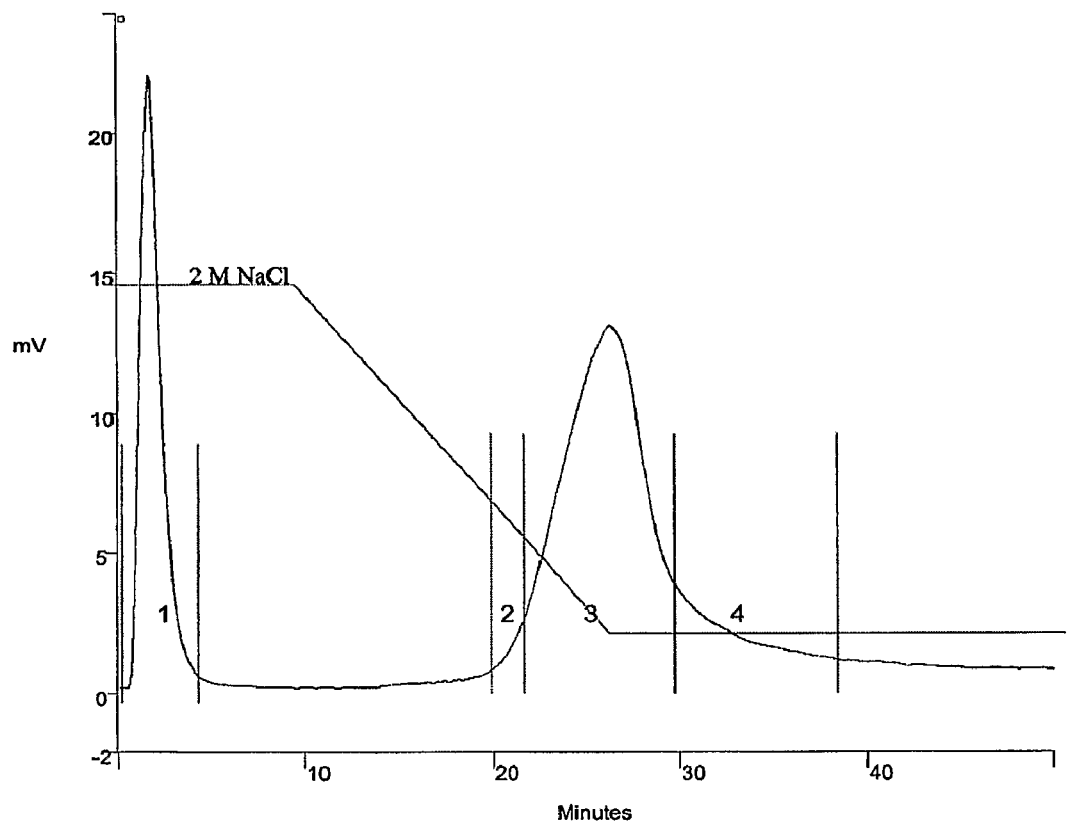

FIG. 22 provides Phenyl SEPHAROSE™ (Low Substitution) Chromatography with 20% Ethylene glycol. Column: Phenyl SEPHAROSE™ low sub (1.0 mL). Absorbance at 280 nm. Sample: CST-II purified by Q-SEPHAROSE™ (conditioned in Buffer B: 2 M NaCl, 25 mM Tris-HCl, pH 7.2), 1.0 mL, 4.2 mg. Gradient: 0-10 min, 100% B, 10-25 min, 100-0% B; 25-50 min, 100% Buffer A (25 mM Tris-HCl, 20% ethylene glycol, pH 7.2). Fractions 1-4 were collected and analyzed by SDS-PAGE (FIG. 21). Fractions were stored at 4° C.

Figure 23:
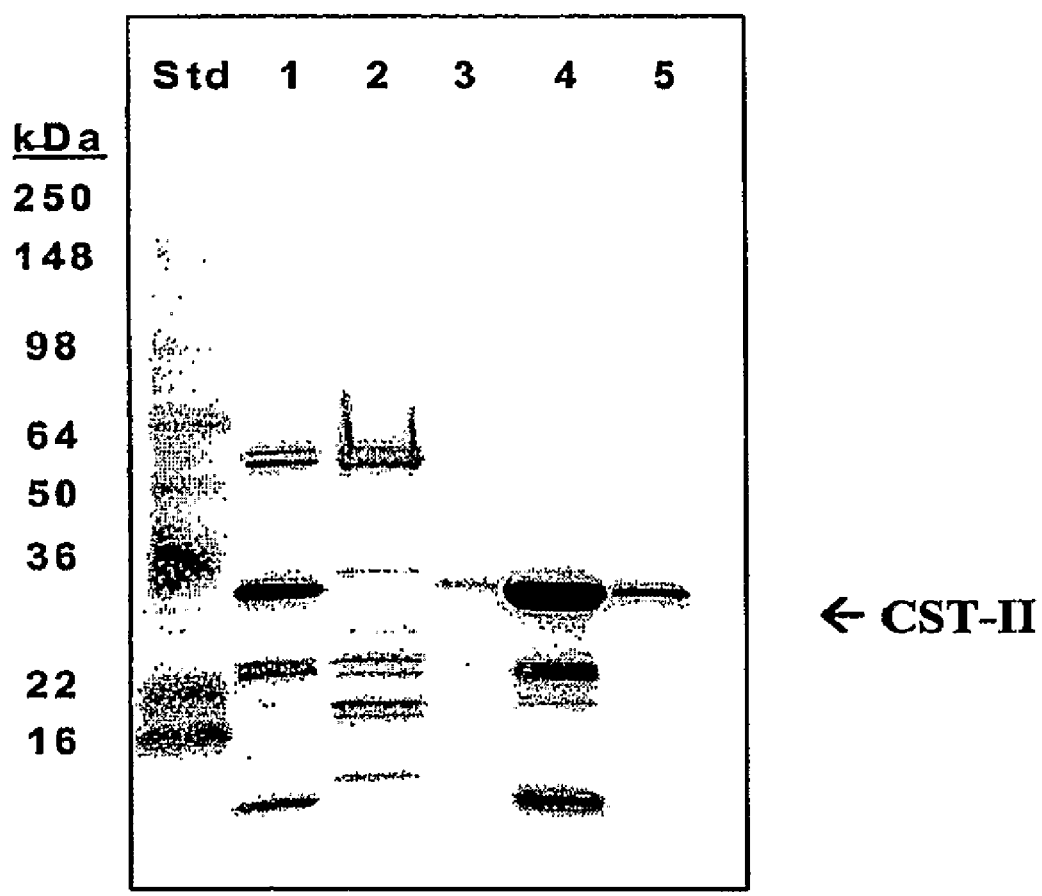

FIG. 23 provides SDS-PAGE Analysis of Phenyl SEPHAROSE™ (Low Substitution) Chromatography (with 20% Ethylene glycol) Fractions. Std=SEEBLUE® Plus 2 (15 mcL). Lane 1: CST-II Purified by Q SEPHAROSE™ (10 mcL). Lane 2: Phenyl SEPHAROSE™ low sub (ethylene glycol) Fraction 1 (FIG. 20) (5.0 mcL). Lane 3: Phenyl SEPHAROSE™ low sub (ethylene glycol) Fraction 2 (5.0 mcL). Lane 4: Phenyl SEPHAROSE™ low sub (ethylene glycol) Fraction 3 (5.0 mcL). Lane 5: Phenyl SEPHAROSE™ low sub (ethylene glycol) Fraction 4 (5.0 mcL). 4-20% Tris-glycine SDS PAGE gel was stained with Wako Silver Stain kit.

Figure 24:
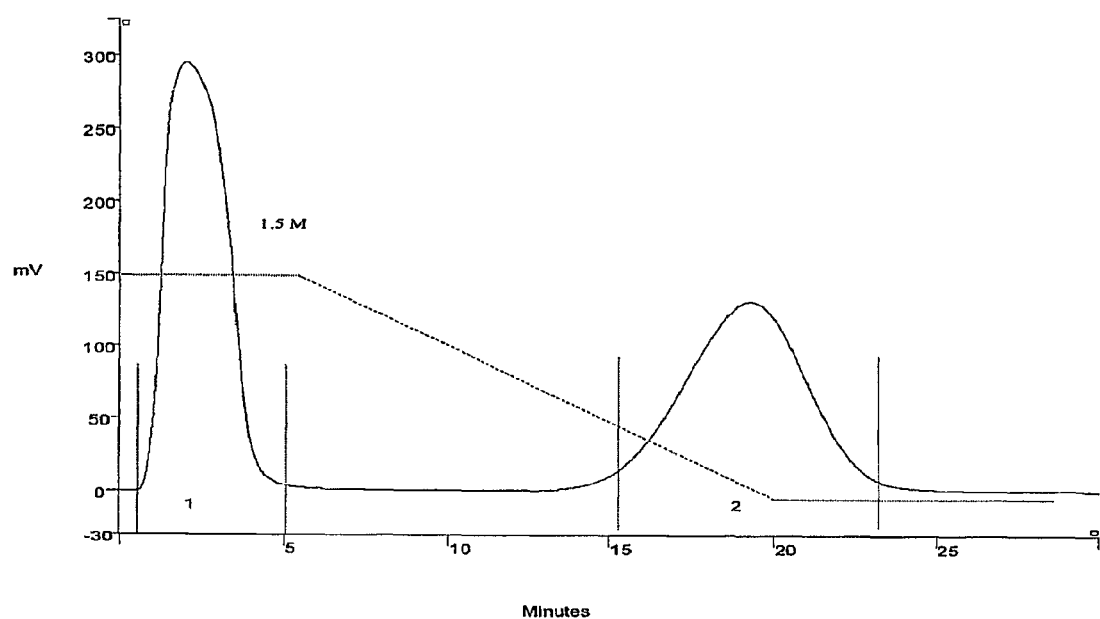

FIG. 24 provides Butyl SEPHAROSE™ Chromatography with 20% Ethylene glycol. Column: Butyl SEPHAROSE™ (1.0 mL). Absorbance at 280 nm. Sample: CST-II purified by Q-SEPHAROSE™ (conditioned in Buffer B: 3 M NaCl, 25 mM Tris-HCl, pH 7.2), 1.0 mL, 4.2 mg. Gradient: 0-10 min, 50% B, 10-20min, 50-0% B; 20-30 min, 100% Buffer A (25 mM Tris-HCl, 20% ethylene glycol, pH 7.2). Fractions 1 and 2 were collected and analyzed by SDS-PAGE (FIG. 23). Fractions were stored at 4° C.

Figure 25:
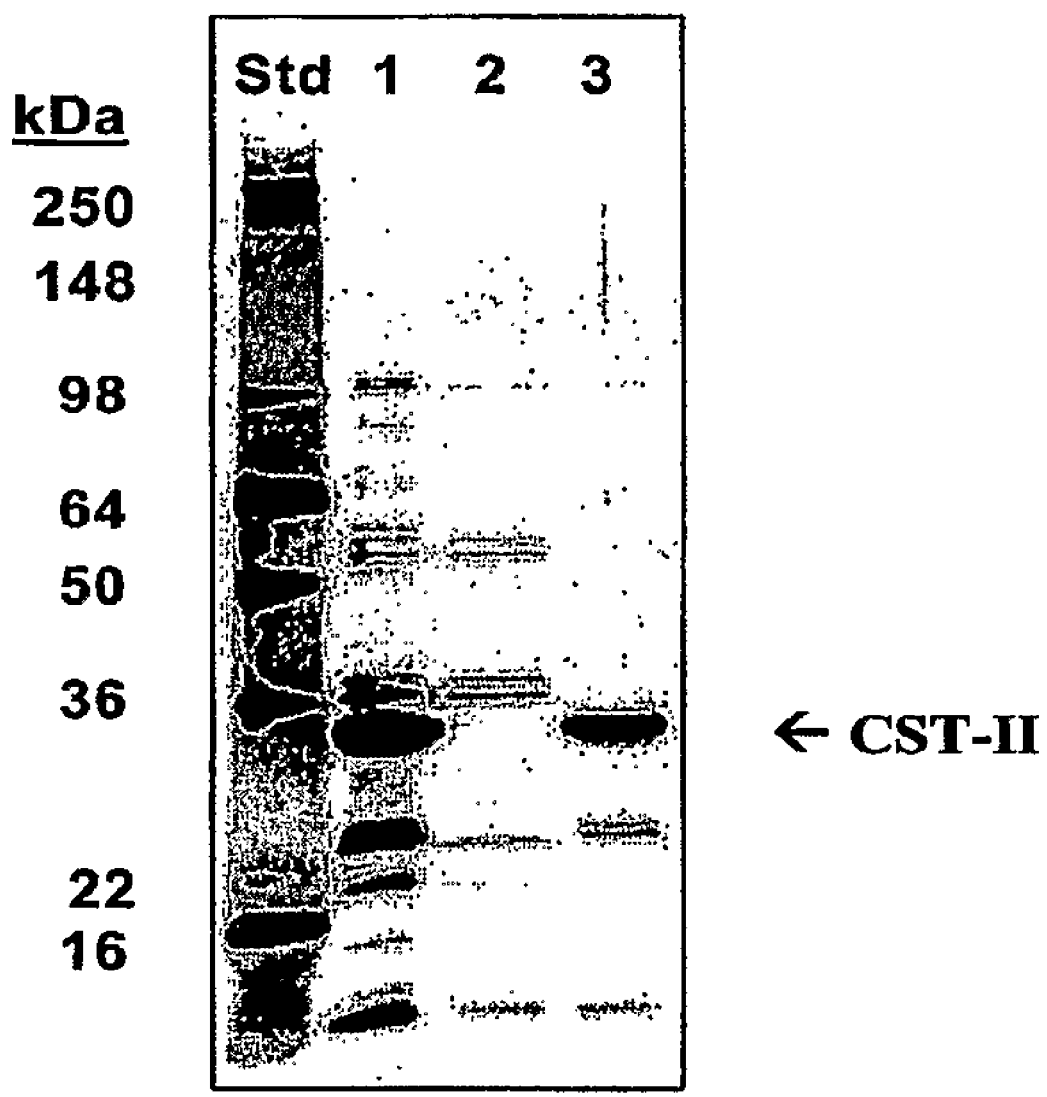

FIG. 25 provides SDS-PAGE Analysis of Butyl SEPHAROSE™ Chromatography Fractions (with 20% Ethylene glycol). Std=SEEBLUE® Plus 2 (10 mcL). Lane 1: CST-II Purified by Q SEPHAROSE™ (10 mcL). Lane 2: Butyl SEPHAROSE™ with Ethylene glycol Fraction 1 (FIG. 22) (5.0 mcL). Lane 3: Butyl SEPHAROSE™ with Ethylene glycol Fraction 2 (5.0 mcL). 4-20% Tris-glycine SDS PAGE gel was stained with Wako Silver Stain kit.

Figure 26:
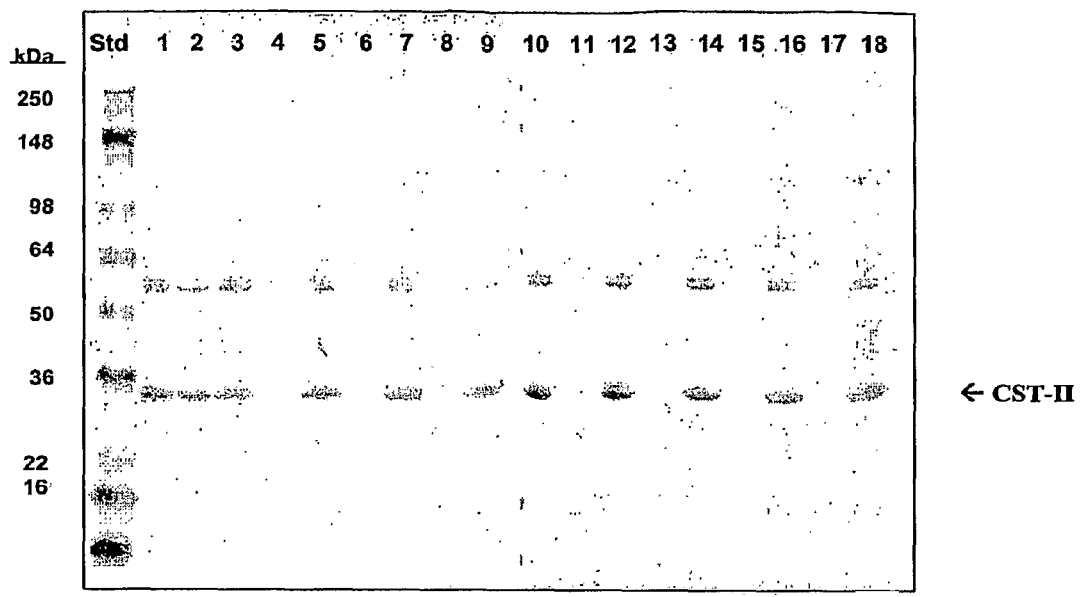

FIG. 26 provides SDS-PAGE Analysis of CST-II Excipient Screen (Cellulose Acetate). CST-II was buffer exchanged into sodium phosphate buffers containing various excipients (described in Table 2) using cellulose acetate centrifugal filters. Each buffer exchanged CST-II solution was sampled for SDS-PAGE (30 mcL) to compare and confirm protein recovery. Std=SEEBLUE® Plus 2 (15 mcL). Lane 1: CST-II Initial Dilution and pH adjustment (30 mcL). Lane 2: CST-II Buffer exchanged with 10 mM sodium phosphate, 10 mM NaCl, pH 6.5 (30 mcL). Lane 3: CST-II Buffer exchanged with 0.1 M NaCl, 10 mM sodium phosphate, pH 6.5 (30 mcL). Lanes 4, 6, 8, 11, 13, 15, 17: Blank. Lane 5: CST-II Buffer exchanged with 0.2 M NaCl, 10 mM sodium phosphate, pH 6.5 (30 mcL). Lane 7: CST-II Buffer exchanged with 0.5 M sucrose, 10 mM sodium phosphate, 10 mM NaCl, pH 6.5 (30 mcL). Lane 9: CST-II Buffer exchanged with 0.1 M mannitol, 10 mM sodium phosphate, 10 mM NaCl, pH 6.5 (30 mcL). Lane 10: CST-II Buffer exchanged with 0.1 mannitol, 0.5 M sucrose, 10 mM sodium phosphate, 10 mM NaCl, pH 6.5 (30 mcL). Lane 12: CST-II Buffer exchanged with 10% glycerol, 10 mM sodium phosphate, 10 mM NaCl, pH 6.5 (30 mcL). Lane 14: CST-II Buffer exchanged with 0.1 M sorbitol, 10 mM sodium phosphate, 10 mM NaCl, pH 6.5 (30 mcL). Lane 16: CST-II Buffer exchanged with 0.02% TWEEN®-20, 10 mM sodium phosphate, 10 mM NaCl, pH 6.5 (30 mcL) Lane 18: CST-II Buffer exchanged with 0.1 M trehalose, 10 mM sodium phosphate, 10 mM NaCl, pH 6.5 (30 mcL). 4-20% Tris-glycine SDS PAGE gels were stained with SIMPLY-BLUE™ Safe Stain.

Figure 27:
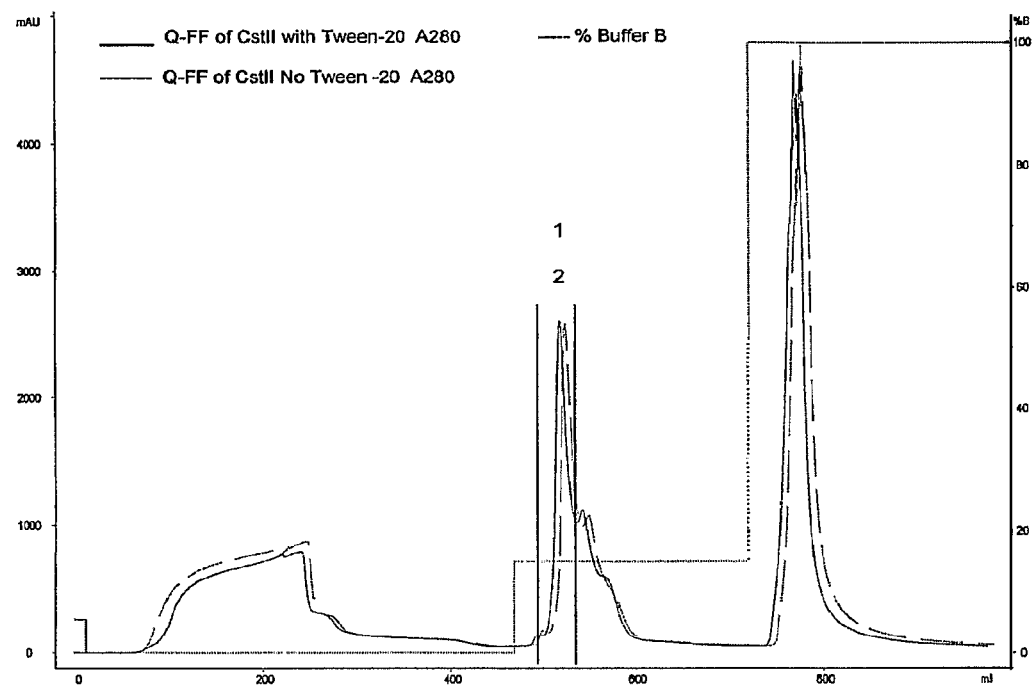

FIG. 27 provides Q-SEPHAROSE™ Purification of CST-II (Step Gradient Elution) with and without TWEEN®-20. Overlay of Chromatograms showing Q-SEPHAROSE™ purification with (blue chromatogram) and without TWEEN®-20 (red dashed chromatogram) in loading and elution solutions. Column: XK26 Q SEPHAROSE™ FF resin (50 mL). Buffer A: 50 mM Tris, pH 8.3 (blue chromatogram: no TWEEN®-20, red dashed chromatogram: 0.005% TWEEN®-20). Buffer B: 1 M NaCl in Buffer A. Column equilibration: 5 column volumes (CV) Buffer A. Loaded clarified homogenate (5 g pellet with 10 mM EDTA, (and for the blue chromatogram only: 0.02% TWEEN®-20), 50 mL, diluted with 150 mL buffer A, conductivity: 3.12 ms/cm). Washed column with 5 CV Buffer A. Step gradient elution with Buffer B: 4 CV at 15% Buffer B, 4 CV at 100% Buffer B. Flow rate of 113 cm/h (10 mL/min). Absorbance at 280 nm. Fraction pools 1 (TWEEN®-20) and 2 (no TWEEN®-20) were collected and sampled for SDS-PAGE.

Figure 28:
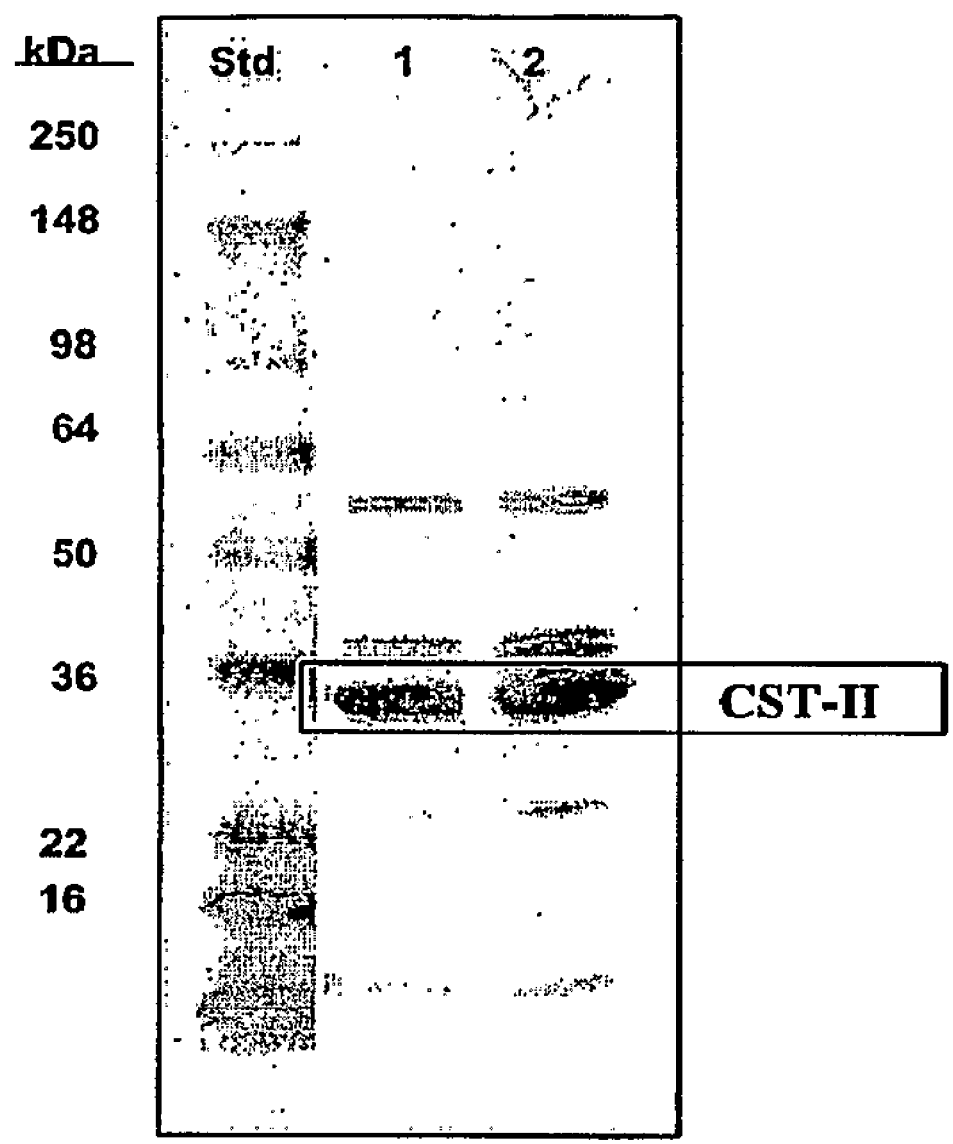

FIG. 28 provides SDS-PAGE Analysis of CST-II Purifications on Q-SEPHAROSE™ with and without TWEEN®-20. Std=SEEBLUE® Plus 2 (15 mcL). Lane 1: CST-II Purified by Q-SEPHAROSE™ with TWEEN®-20 (5.0 mcg). Lane 2: CST-II Purified by Q SEPHAROSE™ without TWEEN®-20 (5.0 mcg). 4-20% Tris-glycine SDS PAGE gel was stained with SIMPLYBLUE™ Safe Stain.

Figure 29:
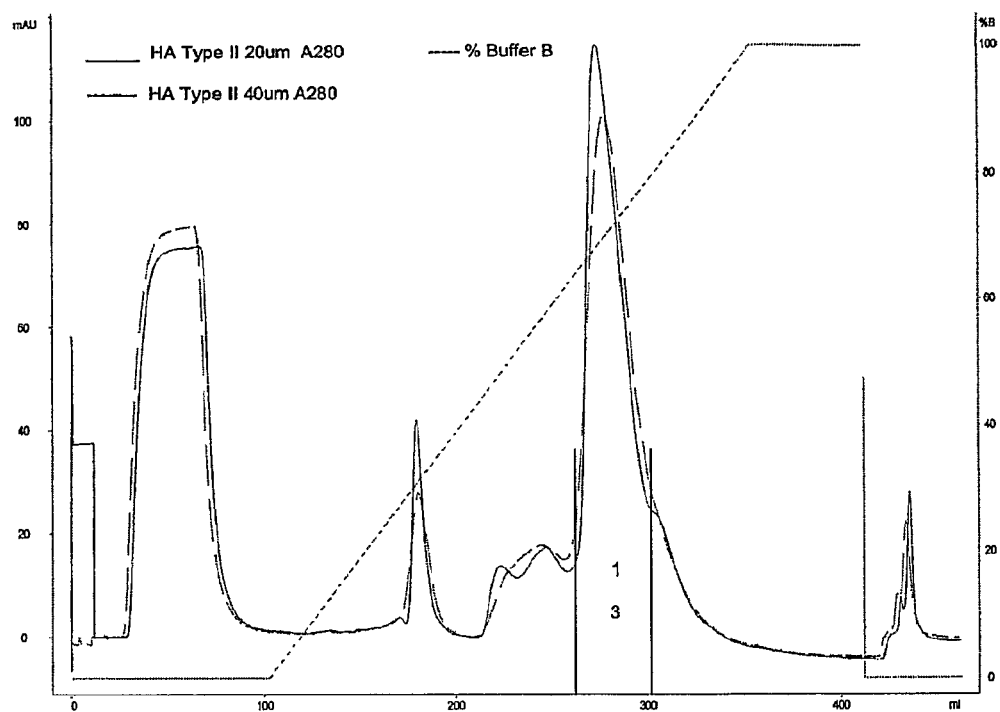

FIG. 29 provides CST-II Purification on Hydroxyapatite Type II—20 micron (blue) and 40 micron (red). Overlay of chromatograms showing purification of CST-II (after Q SEPHAROSE™ with TWEEN®-20, FIG. 25) on hydroxyapatite (HA) Type II 20 micron particle size (blue trace) or 40 micron particle size (red dashed trace). Column: XK16 column Hydroxyapatite Type II (10 mL) resin (Blue chromatogram: 20 micron, Red dashed chromatogram: 40 micron). Equilibration: 5 column volumes (CV) 5 mM sodium phosphate, 0.005% TWEEN®-20, pH 6.5 (Buffer A). Load: CST-II purified by Q SEPHAROSE™ (5 mL, from FIG. 25). Washed column with 10 CV Buffer A. Gradient elution from 0-100% Buffer B (1.5 M NaCl in Buffer A) over 25 CV, followed by 5 CV of 100% Buffer B and 5 CV 500 mM sodium phosphate, pH 6.5. Flow rate 4.0 mL/min (120 cm/h). Absorbance at 280 nm. CST-II fraction pools 1 (20 micron, blue) and 3 (40 micron, red) were collected as shown and analyzed by SDS-PAGE.

Figure 30:
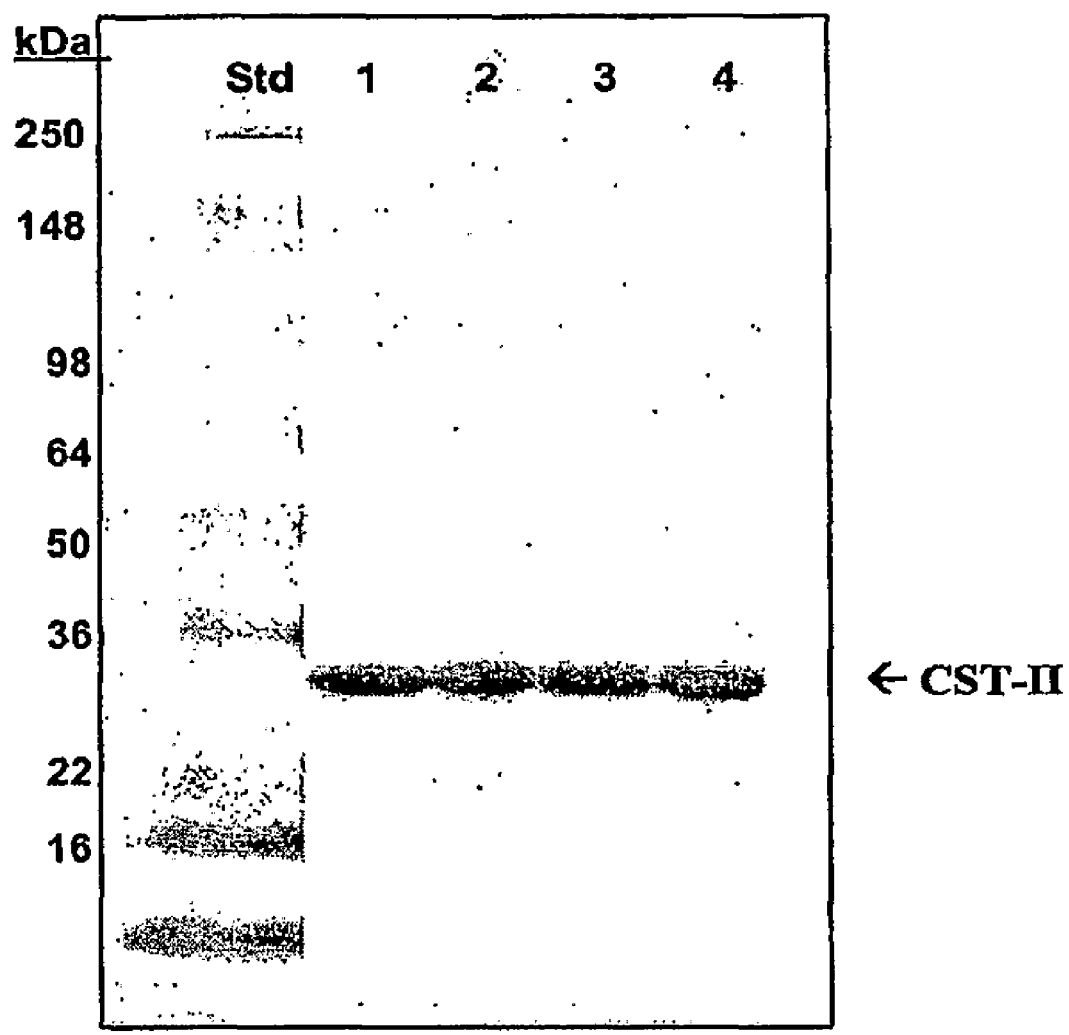

FIG. 30 provides SDS-PAGE Analysis of Hydroxyapatite Type II Fraction Pools (20 micron and 40 micron) before and after SP SEPHAROSE™ HP Chromatography. Std=SEEBLUE® Plus 2(15 mcL). Lane 1: CST-II purified by Q SEPHAROSE™ and hydroxyapatite (HA) Type II (20 micron) (FIG. 27, Fraction pool 1, 5.0 mcg). Lane 2: CST-II purified by Q SEPHAROSE™ HA Type II (20 micron), and SP SEPHAROSE™ HP (FIG. 29, Fraction pool 2, 5.0 mcg). Lane 3: CST-II purified by Q SEPHAROSE™ and HA Type II (40 micron) (FIG. 27, Fraction pool 3, 5.0 mcg). Lane 4: CST-II purified by Q SEPHAROSE™, HA Type II (40 micron), and SP SEPHAROSE™ HP (FIG. 29, Fraction pool 4, 5.0 mcg). 4-20% Tris-glycine SDS PAGE gel was stained with SIMPLYBLUE™ Safe Stain.

Figure 31:
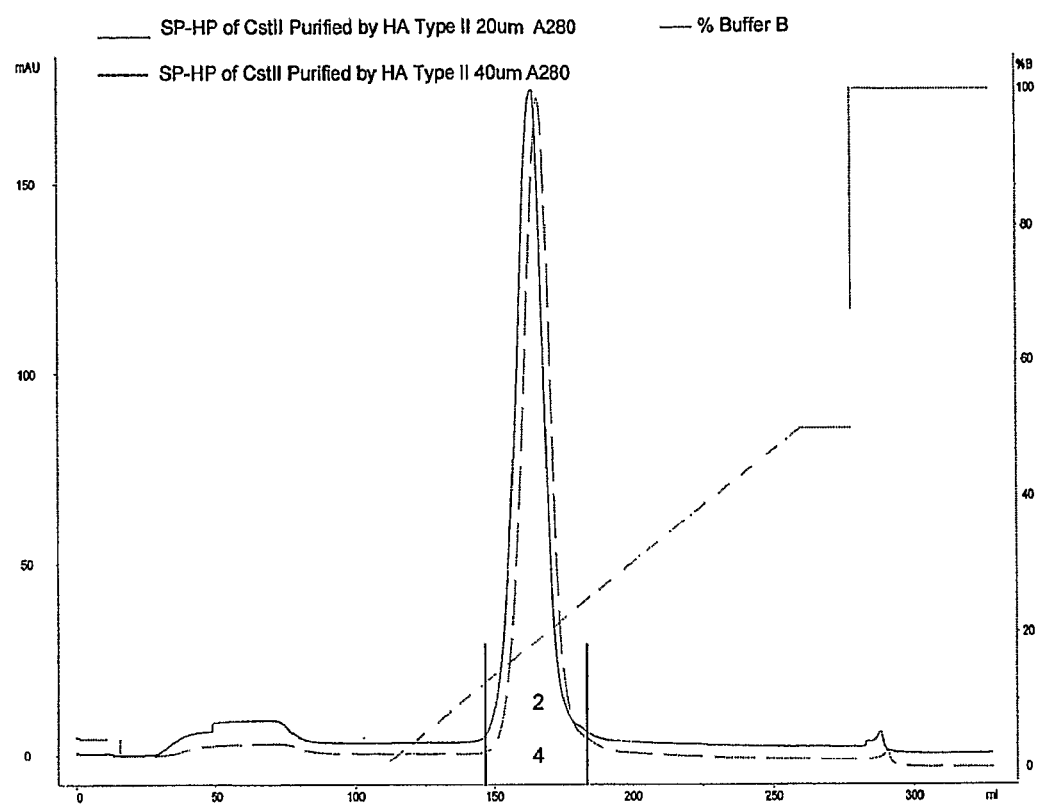

FIG. 31 provides SP-SEPHAROSE™ HP Chromatography of CST-II Partially Purified by Q SEPHAROSE™ and Hydroxyapatite Type II (20 micron and 40 micron). SP SEPHAROSE™ HP purification of CST-II partially purified by Q-SEPHAROSE™ and Hydroxyapatite Type II (20 micron) chromatogram is shown in blue. Overlay chromatogram (red dashes) represents SP SEPHAROSE™ HP purification of CST-II partially purified by Q-SEPHAROSE™ and Hydroxyapatite Type II (40 micron). Column: XK16 SP-SEPHAROSE™ HP resin (10 mL). Equilibration: 5 column volumes (CV) 25 mM MES, pH 6.0 containing 0.005% TWEEN® 20 (Buffer A). Loading: Partially purified CST-II (from FIG. 27) adjusted to 0.02% TWEEN® 20 and dialyzed against 25 mM MES, 10 mM NaCl, pH 6.0 and 0.2 micron filtered (42.3 mL each, pH 6.0, conductivity: 3.6 ms/cm, A280:0.261 Au). Column was washed with 5 CV Buffer A. Gradient elution with Buffer B (1 M NaCl in Buffer A): 0-50% Buffer B over 15 CV, 50% Buffer B for 1 CV, 5 CV of 100% Buffer B. Flow rate: 120 cm/h (4 mL/min). Absorbance at 280 nm. CST-II fraction pools 2 (HA 20 micron, blue) and 4 (HA 40 micron, red) were sampled for SDS-PAGE.

Figure 32:
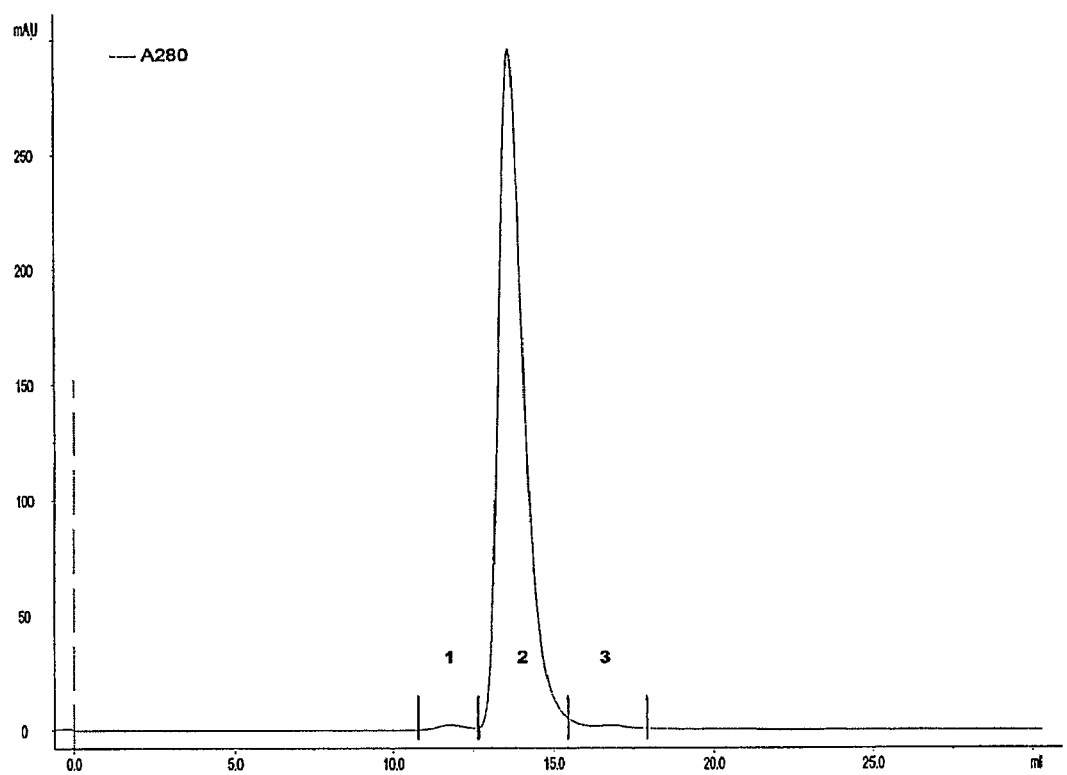

FIG. 32 provides SUPERDEX™ 200 Chromatography of Purified CST-II. Column: SUPERDEX™ 200 10/30 GL. Purified CST-II (Q SEPHAROSE™, Hydroxyapatite Type II, SP SEPHAROSE™ HP, filtered (MUSTANG® E) and formulated in 50% glycerol) stored at −20° C. Injected 250 mcL (711 mcg) on column. Mobile phase: 50 mM sodium phosphate, 150 mM NaCl, pH 7.2. Flow rate 0.5 mL/min. Absorbance at280 nm. Fraction pools 1-3 were collected and analyzed by SDS-PAGE.

Figure 33:
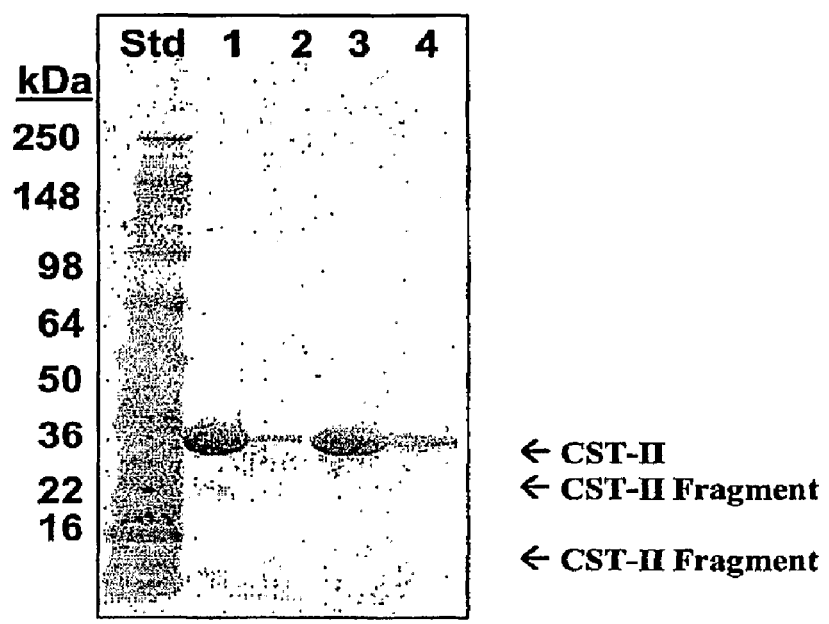

FIG. 33 provides SDS-PAGE Analysis of SUPERDEX™ 200 Fractions of CST-II. Std=SEEBLUE® Plus 2 (15 mcL). Lane 1: Purified CST-II: SUPERDEX™ 200 load (10 meg). Lane 2: SUPERDEX™ 200 Fraction 1 (FIG. 30) concentrated 17.6.times.(30 mcL). Lane 3: SUPERDEX™ 200 Fraction 2 (10 mcg). Lane 4: SUPERDEX™ 200 Fraction 3 concentrated 16.3.times.(30 mcL). 4-20% Tris-glycine SDS PAGE gel was stained with SIMPLYBLUE™ Safe Stain.

Figure 34:
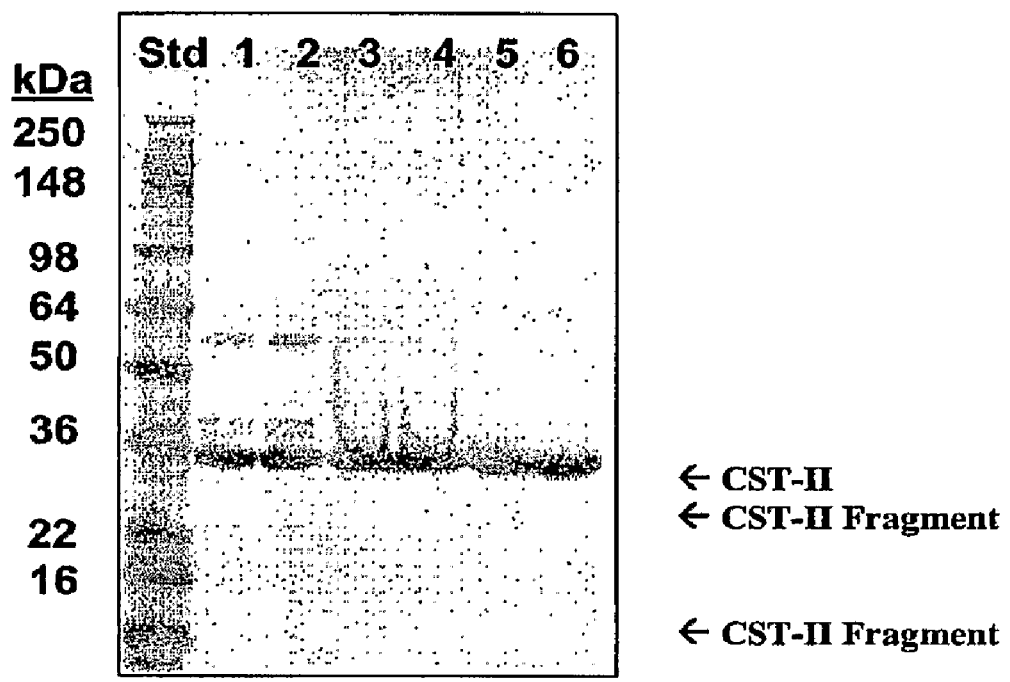

FIG. 34 provides SDS-PAGE Analysis for Proteolytic Activity in CST-II Purification Pools. CST-II purification pools were incubated at 32° C. for 14 hours and analyzed by SDS PAGE gel for evidence of proteolytic activity (increase in number or intentsity of proteolytic fragments). Std=SEEBLUE® Plus 2 (15 mcL). Lane 1: CST-II purified by Q SEPHAROSE™, stored at −20° C. (10 mcg). Lane 2: CST-II purified by Q SEPHAROSE™ incubated at 32° C. (10 meg). Lane 3: CST-II purified by Q SEPHAROSE™ and HA Type II, stored at −20° C. (10 mcg). Lane 4: CST-II purified by Q SEPHAROSE™ and HA Type II incubated at 32° C. (10 mcg). Lane 5: CST-II purified by Q SEPHAROSE™ HA Type II and SP SEPHAROSE™ HP Stored at −20° C. (10 mcg). Lane 6: CST-II purified by Q SEPHAROSE™, HA Type II, and SP SEPHAROSE™ HP incubated at 32° C. (10 mcg). 4-20% Tris-glycine SDS PAGE gel was stained by SIMPLYBLUE™ Safe Stain.

Figure 35:
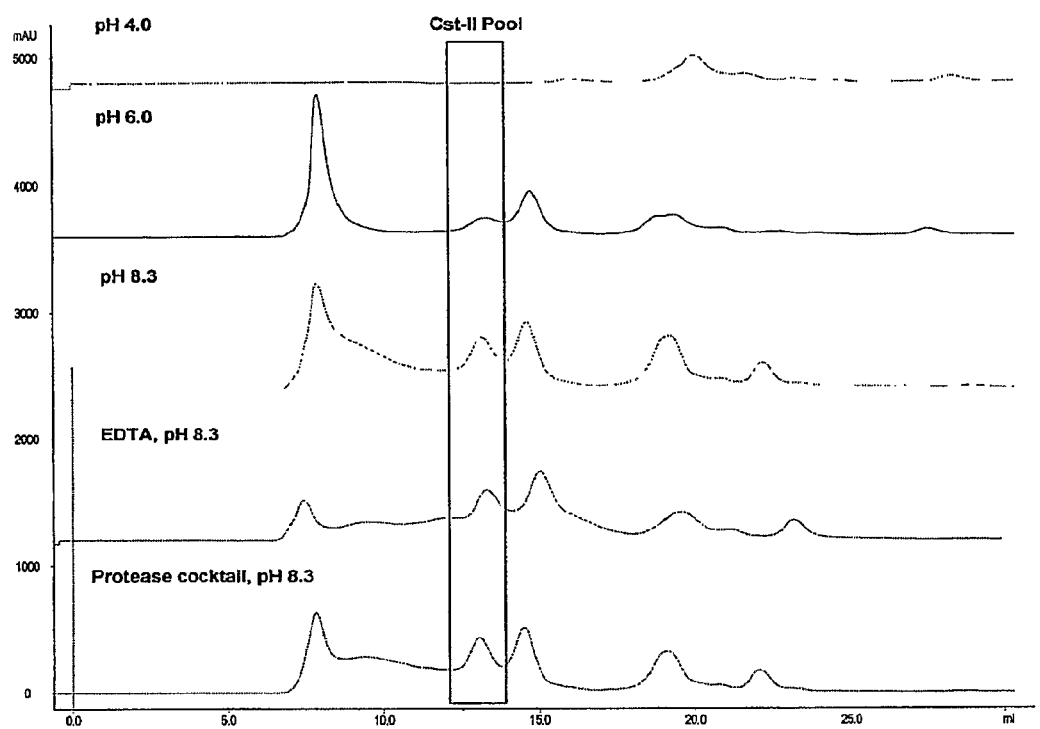

FIG. 35 provides Size Exclusion Chromatography of CST-II Homogenized under Various Conditions (Proteolysis Prevention). Column: SUPERDEX™ 200 10/30GL. Mobile phase: Homogenation test buffer (described below) with 150 mM NaCl. Absorbance at 280 nm Sample: Injected 250 mcL (0.2 micron filtered) CST-II homogenated in following buffers: pH 4 chromatogram: 50 mM sodium acetate, pH 4.0. pH 6.0 chromatogram: 50 mM MES, pH 6.0. pH 8.3 chromatogram: 50 mM Tris, pH 8.3. EDTA, pH 8 chromatogram: 50 mM Tris, 10 mM EDTA, pH 8.3. Protease cocktail, pH 8.3 chromatogram: 50 mM Tris, pH 8.3 plus Protease Inhibitor Cocktail. Collected CST-II elution fractions (shown in box) were analyzed by SDS-PAGE.

Figure 36:
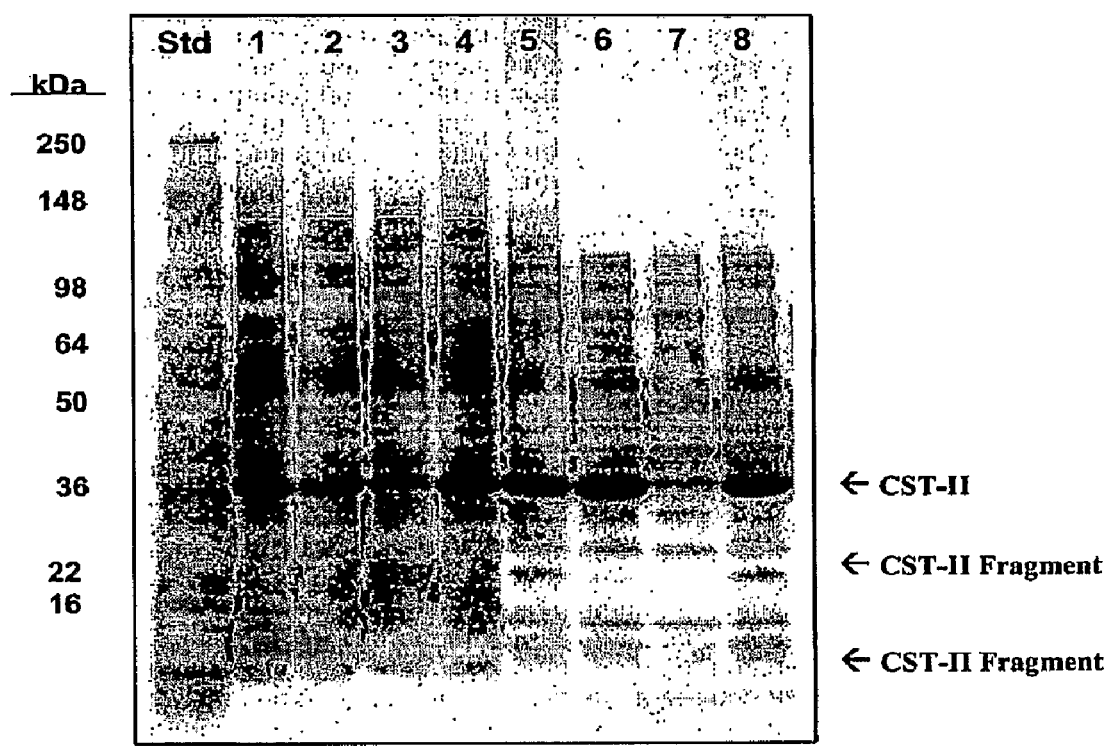

FIG. 36 provides SDS-PAGE Analysis of SUPERDEX™ 200 Fractions of CST-II Homogenation Experiment (Proteolysis Prevention). Std=SEEBLUE® Plus 2 (15 mcL) Lane 1: CST-II homogenate in 50 mM Tris, pH 8.3 (10 mcL). Lane 2: CST-II homogenate in 50 mM Tris, 10 mM EDTA, pH 8.3

(10 mcL). Lane 3: CST-II homogenate in 50 mM MES, pH 6.0 (10 mcL). Lane 4: CST-II homogenate in 50 mM Tris, pH 8.3 plus Protease Inhibitor Cocktail (10 mcL). Lane 5: CST-II homogenate in 50 mM Tris, pH 8.3 SEC-fraction (10 mcL). Lane 6: CST-II homogenate in 50 mM Tris, 10 mM EDTA, pH 8.3 SEC-fraction (10 mcL). Lane 7: CST-II homogenate in 50 mM MES, pH 6.0 SEC-fraction (10 mcL). Lane 8: CST-II homogenate in 50 mM Tris, pH 8.3 plus Protease Inhibitor Cocktail SEC-fraction. Sample homogenized at pH 4 not run on gel, since no CST-II peak was obtained from SUPERDEX™ 200 purification. 4-20% Tris-glycine SDS PAGE gel was stained by SIMPLYBLUE™ Safe Stain.

Figure 37:
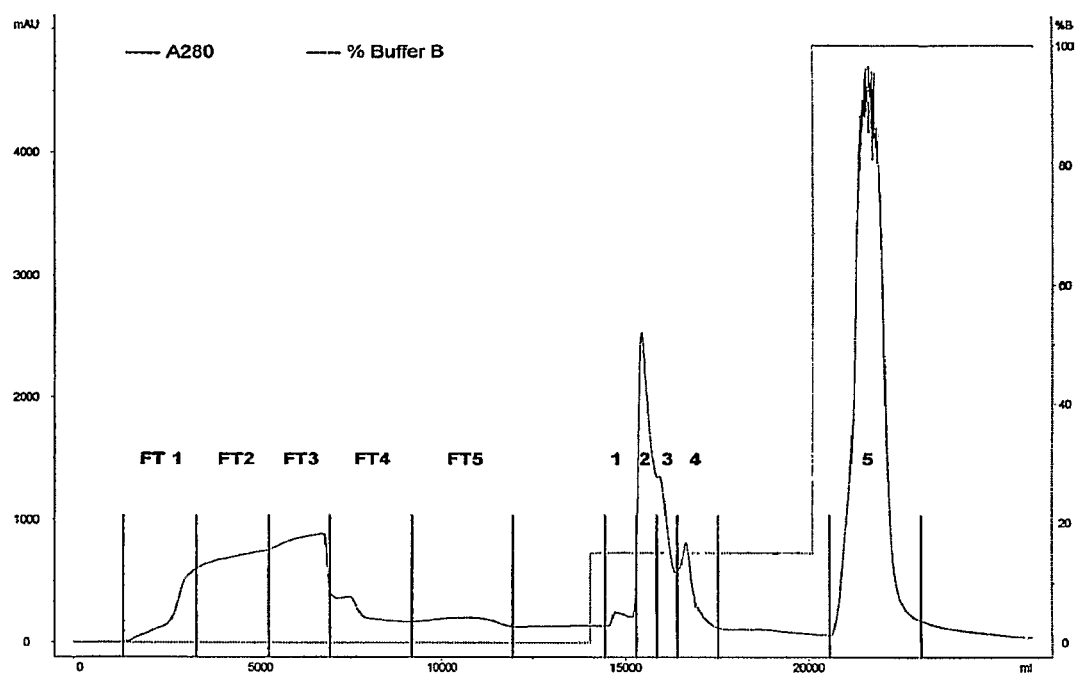

FIG. 37 provides Preparative Q-SEPHAROSE™ FF Purification of CST-II. Column: Vantage S Q-SEPHAROSE™ FF resin (1.5 L). Equilibration: 5 column volumes (V) 50 mM Tris, 0.005% TWEEN®-20, pH 8.3 (Buffer A). Loading: Clarified homogenate (150 g pellet with 10 mM EDTA, 1.5 L, conducitivity 6.1 ms/cm). Column was washed with 5 CV Buffer A. Step gradient elution with Buffer B (1 M NaCl in Buffer A): 5 CV at 15% Buffer B, 5 CV at 100% Buffer B. Flow rate: 100 mL/min (49 cm/h). Absorbance at 280 nm. Fractions were sampled for SDS-PAGE (FIG. 36) and CST-II assay (Table 5). Q-SEPHAROSE™ Elution Fraction 2 (600 mL) was collected for subsequent purification. FT=Flow Through.

Figure 38:
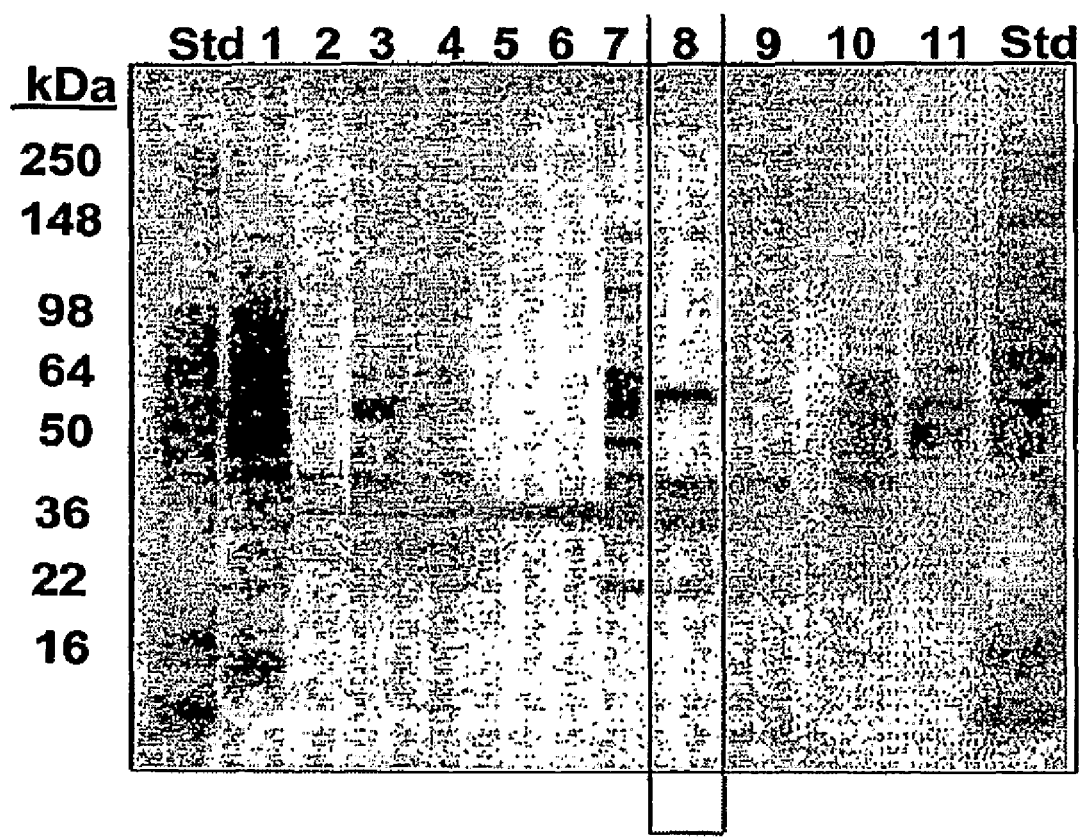
Figure 39:
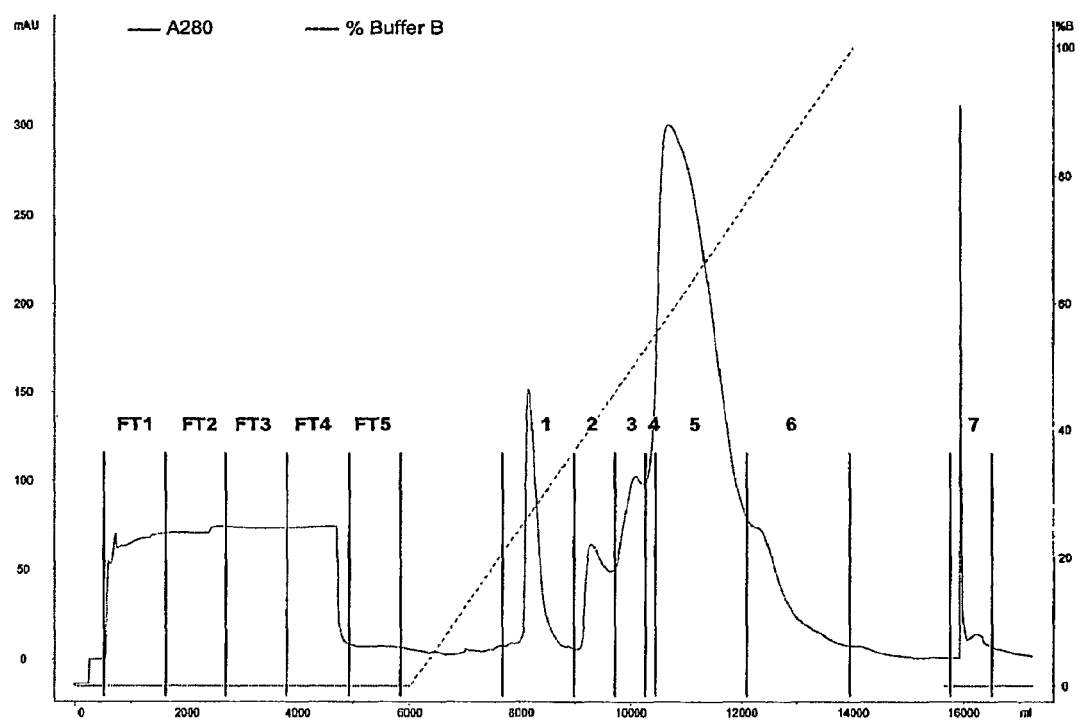

FIG. 38 provides SDS-PAGE Analysis of Fractions from Preparative Q-SEPHAROSE™ FF Purification of CST-II. Std=SEEBLUE® Plus 2 (15 mcL). Lane 1: CST-II Homogenate (5 mcL). Lane 2: Q-SEPHAROSE™ Flow Through Fraction 1 (FIG. 35) (15 mcL). Lane 3: Q-SEPHAROSE™ Flow Through Fraction 2 (15 mcL). Lane 4: Q-SEPHAROSE™ Flow Through Fraction 3 (15 mcL). Lane 5: Q-SEPHAROSE™ Flow Through Fraction 4 (15 mcL). Lane 6: Q-SEPHAROSE™ Flow Through Fraction 5 (15 mcL). Lane 7: Q-SEPHAROSE™ Elution Fraction 1 (30 mcL). Lane 8: Q-SEPHAROSE™ Elution Fraction 2 (2.5 mcL, 10 mcg). Lane 9: Q-SEPHAROSE™ Elution Fraction 3 (5 mcL). Lane 10: Q-SEPHAROSE™ Elution Fraction 4 (10 mcL). Lane 11: Q-SEPHAROSE™ Elution Fraction 5 (1 mcL). 4-20% Tris-glycine SDS PAGE gel was stained with SIMPLYBLUE™ Safe Stain. Q-SEPHAROSE™ Elution Fraction 2 (shown in lane 8) was prepared for subsequent purification FIG. 39 provides Preparative Hydroxyapatite Type II (20 micron) Purification of CST-II. Column: XK50 Hydroxyapatite Type II—20 micron (320 mL). Equilibration: 5 column volumes (CV) 10 mM sodium phosphate, 0.005% TWEEN®-20, pH 6.5 (Buffer A). Loading: Q SEPHAROSE™ Elution Fraction 2 (600 mL, FIG. 35) (pH adjusted, diluted, TWEEN®-20 adjusted and 0.2 micron filtered: 4.2 L, pH=6.54, conductivity=4.0 ms/cm, A280=1.004 AU). Column was washed with 5 CV Buffer A. Gradient elution from 0-100% Buffer B over 25 CV (Buffer B=1.5 M sodium chloride, 10 mM sodium phosphate, 0.005% TWEEN®-20, pH 6.5), 5 CV of 100% Buffer B, followed by 5 CV 500 mM sodium phosphate, pH 6.5. Flow rate: 39.3 mL/min (120 cm/h) Absorbance at 280 nm. Fractions were sampled for SDS-PAGE (FIG. 38) and CST-II assay. Elution Fraction Pool 5 was collected for subsequent purification. FT=Flow Through.

Figure 40:
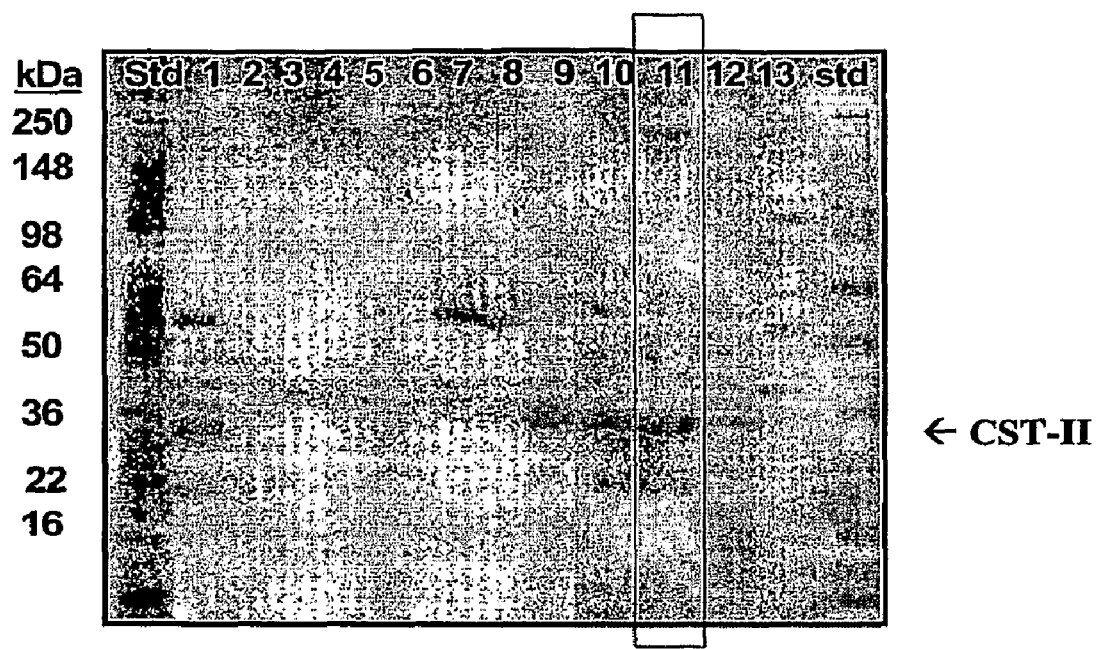

FIG. 40 provides SDS-PAGE Analysis of Fractions from Preparative Hydroxyapatite (HA) Type II (20 micron) Purification of CST-II. Std=SEEBLUE® Plus 2 (15 mcL). Lane 1: CST-II Q-SEPHAROSE™ Elution Fraction 2 (10 mcg). Lane 2: HA Flow Through Fraction 1 (FIG. 39) (20 mcL). Lane 3: HA Flow Through Fraction 2 (20 mcL). Lane 4: HA Flow Through Fraction 3 (20 mcL). Lane 5: HA Flow Through Fraction 4 (20 mcL). Lane 6: HA Flow Through Fraction 5 (20 mcL). Lane 7: HA Elution Pool 1 (20 mcL). Lane 8: HA Elution Pool 2 (20 mcL). Lane 9: HA Elution Pool 3 (20 mcL). Lane 10: HA Elution Fraction 4 (20 mcL). Lane 11: HA Elution Fraction 5 (10 mcg). Lane 12: HA Elution Fraction 6 (10 mcL). Lane 13: HA Elution Fraction 7 (20 mcL). 4-20% Tris-glycine SDS PAGE gel was stained with SIMPLYBLUE™ Safe Stain. Hydroxyapatite Type II Elution fraction 5 (shown in lane 11) was prepared for subsequent purification.

Figure 41:
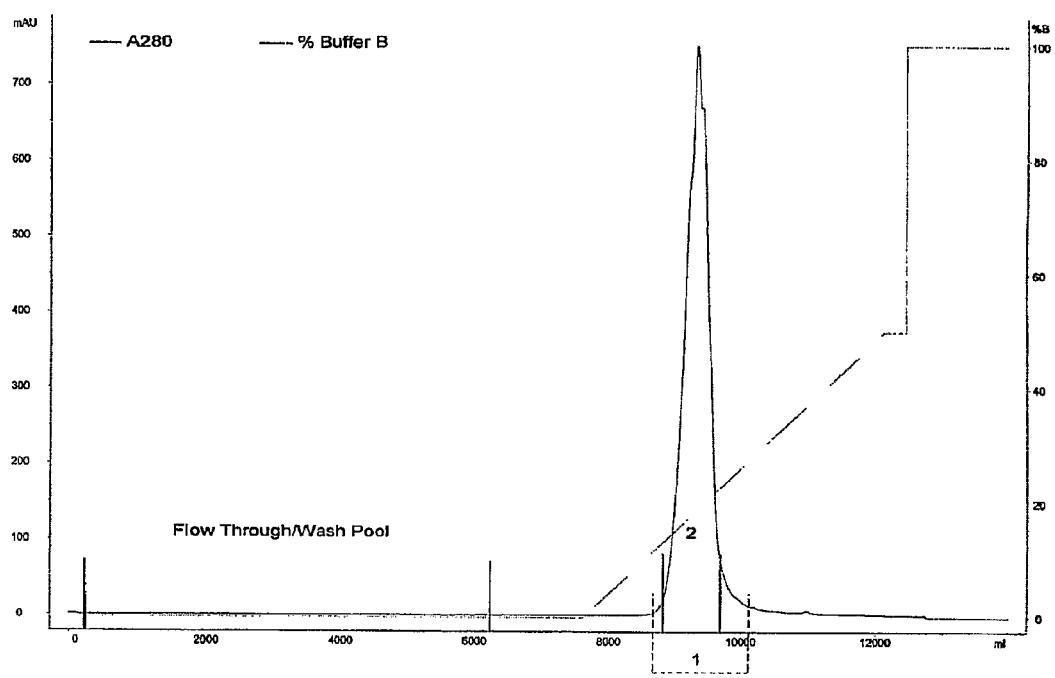

FIG. 41 provides Preparative SP SEPHAROSE™ HP Purification of CST-II. Column: XK50 SP-SEPHAROSE™ HP (300 mL). Equilibration: 5 column volumes (CV) 25 mM MES, 0.005% TWEEN®-20 (buffer A). Loading: CST-II partially purified by Q SEPHAROSE™ and Hydroxyapatite Type If (20 micron) (HA Elution Pool 5 , FIG. 37, 1.65 L) (dialyzed, diluted, 0.2 micron filtered, 6 L, pH=6.03, conductivity=3.9 ms/cm A280:0.291 Au). Column was washed with 5 CV Buffer A. Elution gradient from 0-50% Buffer B over 15 CV (Buffer B=1 M NaCl, in Buffer A), hold at 15% Buffer B for 1 CV, 5 CV 100% Buffer B. Flow rate 39.3 mL/min (120 cm/h). Absorbance at 280 nm. Fractions were sampled for SDS-PAGE (FIG. 40) and CST-II assay (Table 7). SP SEPHAROSE™ HP Elution Pool 2 chosen for further processing and formulation.

Figure 42:
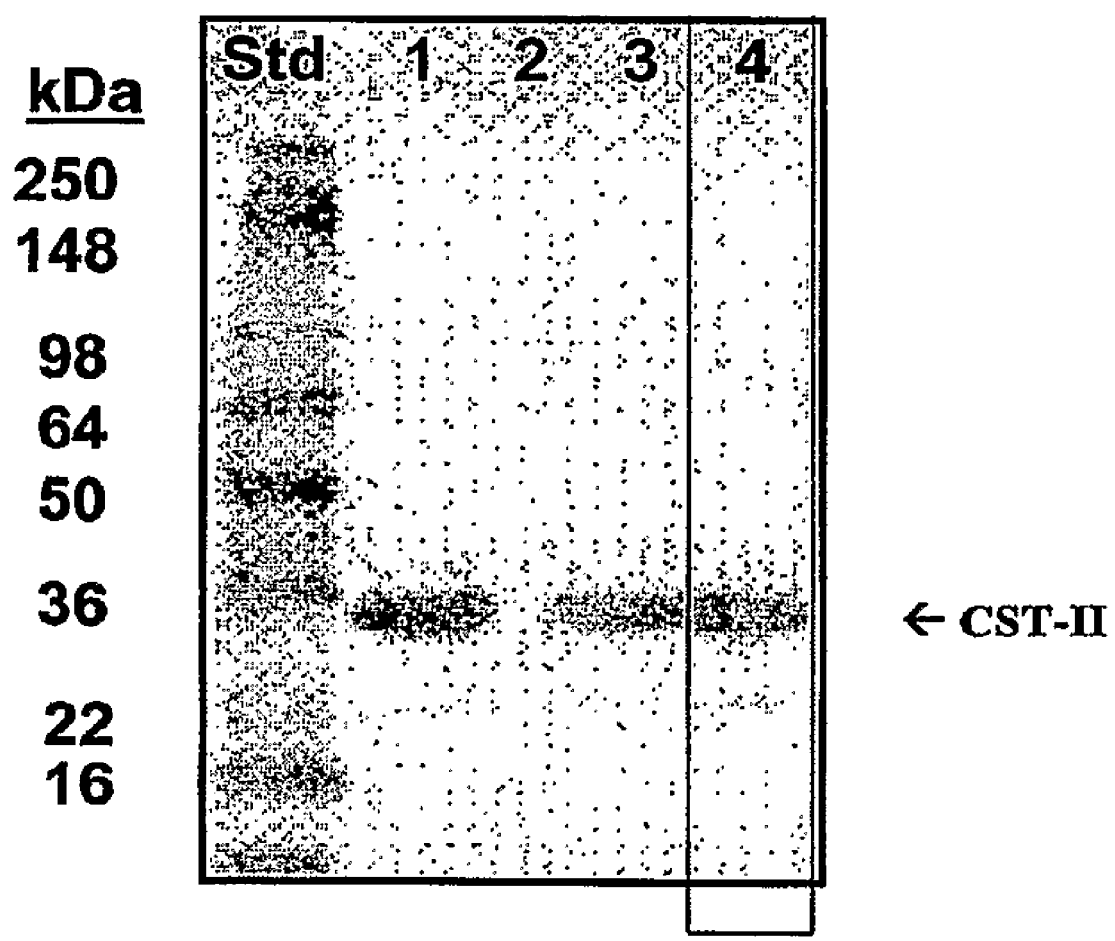

FIG. 42 provides SDS-PAGE Analysis of Fractions of Preparative SP-SEPHAROSE™ HP Purification of CST-II. Std=SEEBLUE® Plus 2 (15 mcL). Lane 1: CST-II purified by Q-SEPHAROSE™ and Hydroxyapatite Type II (20 micron) (Elution Fraction 5, 19.4 mcL, 10 mcg). Lane 2: SP-SEPHAROSE™ HP Flow Through/Wash pool (30 mcL). Lane 3: SP-SEPHAROSE™ HP Elution Pool 1 (10 mcg). Lane 4: SP-SEPHAROSE™ HP Elution Pool 2 (10 mcg). 4-20% Tris-glycine SDS PAGE gel was stained with SIMPLYBLUE™ Safe Stain. SP-SEPHAROSE™ HP Elution Pool 2 (shown in lane 4) was chosen for final formulation.

Figure 43:
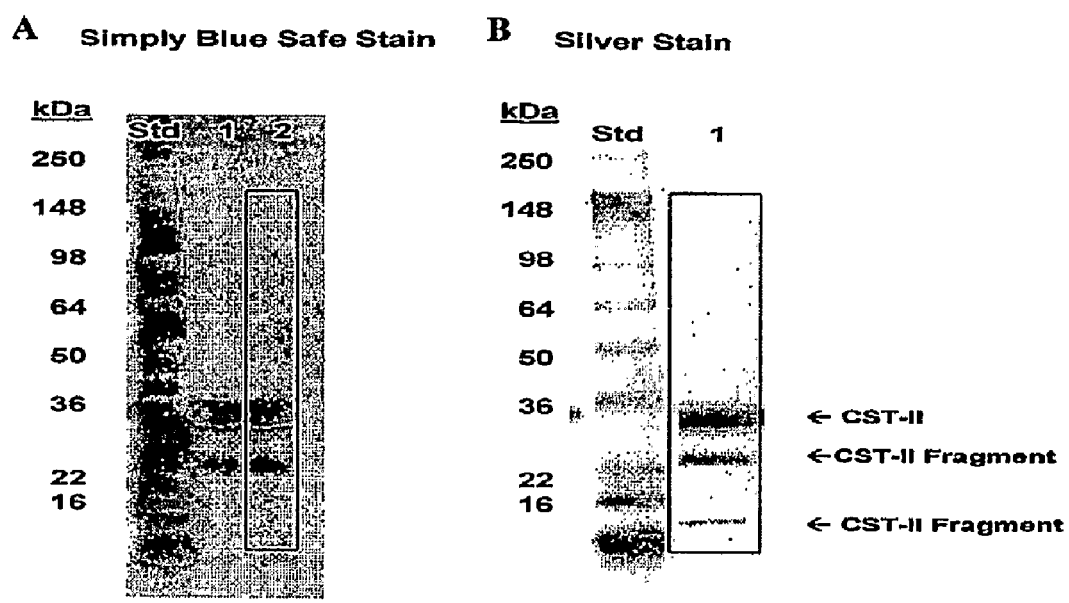

FIG. 43 provides SDS-PAGE Analysis of Formulated CST-II. SIMPLYBLUE™ Safe Stain Gel (A): Std=SEEBLUE® Plus 2 (15 mcL). Lane 1: SEPHAROSE™ HP Fraction Pool 2 (FIG. 39, 10 mcg). Lane 2: Formulated CST-II (10 mcg). 4-20% Tris-glycine SDS PAGE was stained with SIMPLYBLUE™ Stain Safe stain. Silver Stain gel (B): Std=SEEBLUE® Plus 2 (15 mcL). Lane 1: Formulated CST-II (8 mcg). 4-20% Tris-glycine SDS PAGE gel was Silver stained with Wako Silver Stain kit.

Figure 44:
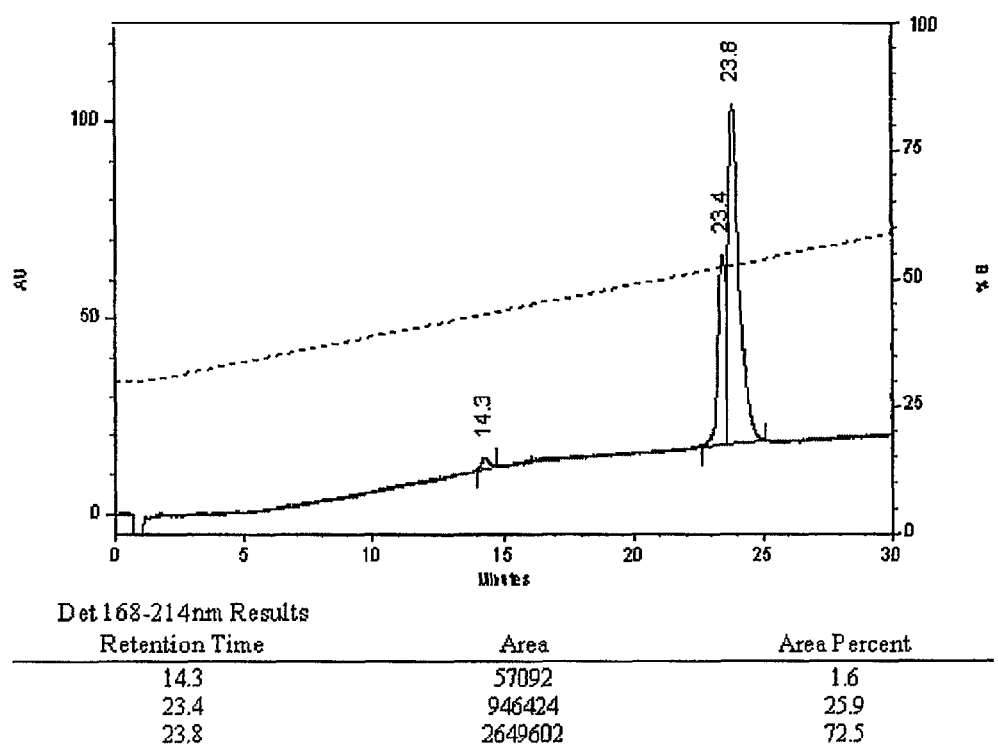

FIG. 44 provides purity analysis by HPLC of Formulated CST-II. $C_3$ RP HPLC conditions: Column; ZORBAX® 300SB-C3 (150.times.2.1 mm, 5 micron), P/N 883750-909; S/N USL B001354. Detector: Beckman SYSTEM GOLD® 168, diode array, UV 214 nm. Column Temp; 45° C. Flow rate: 0.6 mL/min. Eluents: A: 0.1% TFA in water; B: 0.09% TFA in acetonitrile. Gradient: 40% B for 1 min, then 40% to 60% B in 20 min (0.0%/min), from 60% to 80% in 2 min, isocratic for 1 min, 80% to 40% in 2 min, isocratic at 40% B for 6 min. Injection: 4 mcg of purified CST-II. Small peak eluting at 14.3 minutes is CST-II proteolysis fragment (.about.10 kDa).

DETAILED DESCRIPTION OF THE INVENTION

I. Introduction

The present invention provides a tagged-sialyltransferase protein that is expressed in bacteria at levels that are higher than those of the untagged parent sialyltransferase protein.

The invention also provides expression vectors and host cells that can be used to obtain the higher levels of protein production.

II. Definitions

As used herein "sialyltransferase polypeptide" refers to a protein that has sialyltransferase activity and that comprises sialyltransferase motif A and sialyltransferase motif B as disclosed herein. As used herein "sialyltransferase motif A" refers to an amino acid sequence found in sialyltransferase polypeptides, i.e., DVFRCNQFYFED/E, (SEQ ID NO:11), and conservatively modified variants of that sequence. Thus, sialyltransferase motif A refers to DVFRCNQFYFED, (SEQ ID NO:13), and DVFRCNQFYFEE, (SEQ ID NO:14), and conservatively modified variants of those sequences, as well. As used herein "sialyltransferase motif B" refers to an amino acid sequence found in sialyltransferase polypeptides, i.e., RITSGVYMC, (SEQ ID NO:12) and conservatively modified variants of that sequence. In general sialyltransferase motif A is found amino terminal relative to sialyltransferase B in a sialyltransferase polypeptide. Spacing between the two sialyltransferase motifs is not critical. In some embodiments, about 30, 35, 40, 44, 45, 50, 55, 60, 65, 70, 75, 80, 85, 86, 87, 88, 89, 90, 91, 92, 93, 94, 95, 96, 97, 98, 99, 100, 105, or 110 amino acid residues separate the two motifs. Typically, spacing between the two motifs is between e.g., 80 and 100 residues or between 90 and 95 residues, and for some embodiments is usually, e.g., 91, 92, or 93 amino acid residues. Sialyltransferase motifs are described further in International Application PCT/CA2005/001432, filed Sep. 16, 2005, which is herein incorporated by references for all purposes. Sialyltransferase proteins can be from prokaryotic organisms, such as bacteria. In some embodiments, sialyltransferase proteins are from *Campylobacter*. In a further embodiment, sialyltransferase proteins are from *Campylobacter jejuni*. *Campylobacter* sialyltransferase proteins include, e.g., CstI, CstII, and CstIII proteins.

In some embodiments, sialyltransferase protein refers to a polypeptide that has at least 85%, 86%, 87%, 88%, 89%, 90%, 91%, 92%, 93%, 94%, 95%, 96%, 97%, 98% or 99% identity to SEQ ID NO:4 or SEQ ID NO:5. The sialyltransferase polypeptide has sialyltransferase activity, i.e., the protein catalyzes the transfer of a donor substrate, such as an activated sialic acid molecule, to an acceptor substrate, such as an oligosaccharide, glycolipid, or glycoprotein. This group of sialyltransferase polypeptides includes proteins that catalyze addition of the sialic acid residue in an α2,3 linkage, proteins that catalyze addition of the sialic acid residue in an α2,8 linkage, and dual function proteins that catalyze addition of the sialic acid residue in an α2,3 linkage and an α2,8 linkage. In one embodiment, the sialyltransferase polypeptide is from *Campylobacter jejuni*, e.g., a CSTII polypeptide. Examples of *Campylobacter* sialyltransferase proteins are found in, e.g., U.S. Pat. No. 6,503,744 issued Jan. 7, 2003 and U.S. Pat. No. 6,699,705 issued Mar. 2, 2004, both of which are herein incorporated by reference; and sequences disclosed in the following accession numbers: CAA40567, CAB73395, AAL09368, AAL36462, ZP_00322176, ZP_00321441, ZP_00155359; ZP_00156191, AAL05990, AAG43979, AAK03258, AAF13495, AAK96001, AAK91725, AAL06004, CAB73395, AAL09368, NP_245125, and AAL36462.

As used herein, a "truncated sialyltransferase polypeptide" or grammatical variants, refers to a sialyltransferase polypeptide that has been manipulated to remove at least one amino acid residue, relative to a wild type sialyltransferase polypeptide that occurs in nature, so long as the truncated sialyltransferase polypeptide retains enzymatic activity. For example, *C. jejuni* Cst-I polypeptides comprising amino acids 1 though about 285 are active; *C. jejuni* Cst-II polypeptides comprising amino acids 1 though about 255 are active; and *C. jejuni* Cst-III polypeptides comprising amino acids 1 though about 255 are active.

As used herein, a "tagged sialyltransferase protein or polypeptide" refers to a sialyltransferase that is encoded by a nucleic acid sequence that includes the amino acid tag MGS at the amino terminus of the protein. In some embodiments a protein expressed by that nucleic acid begins with the methionine of the MGS. In other embodiments, proteolytic degradation of the expressed protein can occur and the produced protein is a mixture of proteins, including proteins that begin with the methionine, glycine or serine of the MGS tag or the native methionine of the sialyltransferase. In a further embodiment, the majority of the produced protein begins with the glycine of the MGS sequence. In one embodiment, between 50 and 99% of the tagged sialyltransferase protein starts with the glycine of the MGS sequence. In another embodiment, 50%, 51%, 55%, 60%, 65%, 70%, 75%, 80%, 85%, 90%, 91%, 92%, 93%, 94%, 95%, 96%, 97%, 98%, or 99% of the tagged sialyltransferase protein starts with the glycine of the MGS sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed sialyltransferases. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, Proteins (1984)).

The cells and methods of the invention are useful for producing a sialylated product, generally by transferring a sialic acid moiety from a donor substrate to an acceptor molecule. The cells and methods of the invention are also useful for producing a sialylated product sugar comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl (N-acetylneuraminyl).

The term "sialic acid" or "sialic acid moiety" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as NeuSAc, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O13 $C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

A "sialylated product saccharide" refers an oligosaccharide, polysaccharide (e.g., heparin, carragenin, and the like) or a carbohydrate moiety, either unconjugated or conjugated to a glycolipid or glycoprotein, e.g., a biomolecule, that includes a sialic acid moiety. Any of the above sialic acid moieties can be used as well as PEGylated sialic acid derivatives. In some embodiments other sugar moieties, e.g., fucose, galactose, glucose, GalNAc, or GluNAc, are also added to the acceptor substrate to produce the sialylated product saccharide. Examples of sialylated product saccharides include, e.g., sialylactose.

The term "PEG" refers to poly(ethylene glycol). PEG is an exemplary polymer that has been conjugated to peptides. The use of PEG to derivatize peptide therapeutics has been demonstrated to reduce the immunogenicity of the peptides and prolong the clearance time from the circulation. For example, U.S. Pat. No. 4,179,337 (Davis et al.) concerns non-immunogenic peptides, such as enzymes and peptide hormones coupled to polyethylene glycol (PEG) or polypropylene glycol. Between 10 and 100 moles of polymer are used per mole peptide and at least 15% of the physiological activity is maintained.

An "acceptor substrate" or an "acceptor saccharide" for a glycosyltransferase, e.g. a sialyltransferase, is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate can vary for different types of a particular glycosyltransferase. Accordingly, the term "acceptor substrate" is taken in context with the particular glycosyltransferase of interest for a particular application. Acceptor substrates for sialyltransferases and additional glycosyltransferases, are described herein.

A "donor substrate" for glycosyltransferases is an activated nucleotide sugar. Donor substrates for sialyltransferases, for example, are activated sugar nucleotides comprising the desired sialic acid. For instance, in the case of NeuAc, the activated sugar is CMP-NeuAc. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

The term "contacting" is used herein interchangeably with the following: combined with, added to, mixed with, passed over, incubated with, flowed over, etc.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

"Commercial scale" refers to gram scale production of a sialylated product in a single reaction. In preferred embodiments, commercial scale refers to production of greater than about 50, 75, 80, 90, 100, 125, 150, 175, or 200 grams of sialylated product.

The recombinant proteins of the invention can be constructed and expressed as a fusion protein with a molecular "purification tag" at one end, which facilitates purification or identification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO:19) or a substantially identical variant thereof. Other suitable tags are known to those of skill in the art, and include, for example, an affinity tag such as a hexahistidine peptide (SEQ ID NO:20), which will bind to metal ions such as nickel or cobalt ions or a myc tag. Proteins comprising purification tags can be purified using a binding partner that binds the purification tag, e.g., antibodies to the purification tag, nickel or cobalt ions or resins, and amylose, maltose, or a cyclodextrin. Purification tags also include maltose binding domains and starch binding domains. Purification of maltose binding domain proteins is known to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468,374, filed May 5, 2003, herein incorporated by reference in its entirety.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms nucleic acid, "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression, may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "fusion sialyltransferase polypeptide" or a "fusion glycosyltransferase polypeptide" of the invention is a polypeptide that contains a glycosyltransferase catalytic domain and a second catalytic domain from an accessory enzyme (e.g., a CMP-Neu5Ac synthetase). The fusion polypeptide is capable of catalyzing the synthesis of a sugar nucleotide (e.g., CMP-NeuAc) as well as the transfer of the sugar residue from the sugar nucleotide to an acceptor molecule. Typically, the catalytic domains of the fusion polypeptides will be at least substantially identical to those of glycosyltransferases and fusion proteins from which the catalytic domains are derived. In some embodiments, the a CMP-sialic acid synthase polypeptide and a sialyltransferase polypeptide are fused to form a single polypeptide. Many sialyltransferase enzymes are known to those of skill and can be used in the methods of the invention. For example, a fusion between a *Neisseria* CMP-sialic acid synthase polypeptide and a *Neisseria* sialyltransferase protein is described in, e.g., WO99/31224 and Gilbert et al., *Nat. Biotechnol.* 16:769-72 (1998). Other fusions can be used in the invention, for example, between a *Neisseria* CMP-sialic acid synthase polypeptide and a *Campylobacter* sialyltransferase.

An "accessory enzyme," as referred to herein, is an enzyme that is involved in catalyzing a reaction that, for example, forms a substrate or other reactant for a glycosyltransferase reaction. An accessory enzyme can, for example, catalyze the formation of a nucleotide sugar that is used as a sugar donor moiety by a glycosyltransferase. An accessory enzyme can also be one that is used in the generation of a nucleotide triphosphate that is required for formation of a nucleotide sugar, or in the generation of the sugar which is incorporated into the nucleotide sugar.

A "catalytic domain" refers to a portion of an enzyme that is sufficient to catalyze an enzymatic reaction that is normally carried out by the enzyme. For example, a catalytic domain of a sialyltransferase will include a sufficient portion of the sialyltransferase to transfer a sialic acid residue from a sugar donor to an acceptor saccharide. A catalytic domain can include an entire enzyme, a subsequence thereof, or can include additional amino acid sequences that are not attached to the enzyme or subsequence as found in nature.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other sialylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (located on the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. I is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, $M=5$, $N=-4$, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:3 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

III. Sialyltransferase Polypeptides

The sialyltransferase polypeptides of the inventions typically comprise two motifs: sialyltransferase motif A, DVFRCNQFYFED/E (SEQ ID NO:11), and conservatively modified variants of that sequence and sialyltransferase motif B, RITSGVYMC (SEQ ID NO:12), and conservatively modified variants of that sequence. In some embodiments, the sialyltransferase polypeptides comprise either the sialyltransferase motif A DVFRCNQFYFED (SEQ ID NO:11) or DVFRCNQFYFEE (SEQ ID NO:11). and sialyltransferase motif B RITSGVYMC (SEQ ID NO:12). The sialyltransferase polypeptides of the invention catalyze the transfer of a sialic acid moiety from a donor substrate to an acceptor substrate.

In some embodiments the sialyltransferase polypeptides also comprise other amino acid residues that appear to be important for enzymatic activity. For example, the structure of Cst-II from *Campylobacter jejuni* strain OH4384 has been solved. (See, e.g., Chiu et al., *Nat. Struc. Mol. Biol.* 11:163-170 (2004)). Mutational analysis of the Cst-II enzyme demonstrated that, for example the arginine residue of sialyltransferase motif B is required for activity. The arginine residue of sialyltransferase motif B is referred to as R129 in Cst-II and correlates to R165 of the sialyltransferase consensus sequence of FIG. 1. Other amino acid residues that appear to be important for catalytic activity include Cst-II Y156, Cst-II Y162 and Cst-II H188. Thus, in some embodiments, the sialyltransferase polypeptides comprise sialyltransferase motif A, sialyltransferase motif B and an amino acid residue corresponding to consensus Y192; or sialyltransferase motif A, sialyltransferase motif B and an amino acid residue corresponding to consensus-Y192 and an amino acid residue corresponding to consensus Y199 or H226; or sialyltransferase motif A, sialyltransferase motif B and an amino acid residue corresponding to consensus Y199; or sialyltransferase motif A, sialyltransferase motif B and an amino acid residue corresponding to consensus Y199 and an amino acid residue corresponding to consensus H226; or sialyltransferase motif A, sialyltransferase motif B and an amino acid residue corresponding to consensus H226; sialyltransferase motif A, sialyltransferase motif B and an amino acid residue corresponding to consensus Y192, an amino acid residue corresponding to consensus Y199 and an amino acid residue corresponding to consensus H226.

Other amino acid residues can be important for enzymatic activity based on the structural data and can be included in sialyltransferase polypeptides with sialyltransferase motifs A and B, e.g., amino acid residues corresponding to consensus residues N44, N86, Q93, D190, F191, S198, F215, or Y222. Those of skill will note on reviewing FIG. 1, that at consensus residues S198, Y222, and F215, other amino acids can be tolerated. Also, N86 and Q93 are deleted from sialyltransferase polypeptides, e.g., from some *H. influenzae* sialyltransferase polypeptides. The above amino acids residues can be included in a sialyltransferase polypeptide, i.e., a polypeptide singly or in any combination, including combinations with amino acid residues corresponding to consensus Y192, Y199 or H226.

The sialyltransferase polypeptides can also be modified, so long as they maintain sialyltransferase activity. Modifications include truncations, described supra, and, in some embodiments, site directed mutagenesis of the protein.

Site directed mutagenesis can be used to alter the acceptor specificity of a sialyltransferase polypeptide comprising conserved sequence motifs. Some sialyltransferase polypeptides are able to sialylate an acceptor molecule by forming α2,3 and/or α2,8 linkages. For example CstII enzymes from *C. jejuni* strains OH4382, OH4384, O:10, and O:41 are all able to form α2,3 and/or α2,8 linkages. Mutation of Asn51 to a threonine residue eliminated the ability of CstII from OH4282, OH4384 to add sialic acid in an α2,8 linkage. However, mutation of Thr51 to asparagines in a monofunctional O:19 strain, resulted in an enzyme that was able to a sialic acid in both an α2,3 as well as an α2,8 linkage. (See, e.g., Gilbert et al., *J. Biol. Chem.* 277:327-337 (2002).

Site directed mutagenesis can be used to alter overall enzyme activity or protein stability. In addition, a mutation of residue Ile53 to a serine or glycine in CstII enzymes from *C. jejuni* strains OH4382, OH4384 resulted in large increases in enzymatic activity. See, e.g., Chiu et al., *Nat. Struct. Mol. Biol.* 11:163-70 (2004)

IV. Isolation of Nucleic Acids Encoding Sialyltransferase Polypeptides

Nucleic acids that encode sialyltransferase polypeptides for use in the present invention are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning* 13 *A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a sialyltransferase polypeptide can be prepared by any suitable method described above, including, for example, cloning and restriction of appropriate sequences with restriction enzymes. In one preferred embodiment, nucleic acids encoding sialyltransferase polypeptides are isolated by routine cloning methods. A nucleotide sequence of a sialyltransferase polypeptide as provided in, for example, SEQ ID NO:4 and 5, or other sequence database (see above) can be used to provide probes that specifically hybridize to a gene encoding a sialyltransferase polypeptide; or to an mRNA that encodes a sialyltransferase polypeptide (e.g., in a Southern or Northern blot). Once the target nucleic acid encoding a sialyltransferase polypeptide is identified, it can be isolated according to standard methods known to those of skill in the art (see, e.g., Sambrook et al. (1989) *Molecular Cloning: A Laboratory Manual, 2nd Ed., Vols.* 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length sialyltransferase polypeptide, or subsequences thereof, e.g., containing subsequences encoding at least a subsequence of a catalytic domain of a sialyltransferase polypeptide. These restriction enzyme fragments, encoding a sialyltransferase polypeptide or subsequences thereof, may then be ligated, for example, to produce a nucleic acid encoding a sialyltransferase protein.

A nucleic acid encoding a sialyltransferase polypeptide c, or a subsequence thereof, can be characterized by assaying for the expressed product. Assays based on the detection of the physical, chemical, or immunological properties of the expressed protein can be used. For example, one can identify a cloned sialyltransferase by the ability of a protein encoded by the nucleic acid to catalyze the transfer of a sialic acid moiety from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for $\alpha 2,3$-sialyltransferase, Lac-FCHASE is used as a substrate. To assay for $\alpha 2,8$-sialyltransferase, GM3-FCHASE is used as a substrate. (See, e.g., U.S. Pat. No. 6,503,744, which is herein incorporated by reference.) The reaction products of other glycosyltransferases can be detected using capillary electrophoresis, e.g., to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Wakarchuk, supra). Other methods for detection of oligosaccharide reaction products include thin layer chromatography and GC/MS and are disclosed in U.S. Pat. No. 6,503,744, which is herein incorporated by reference.

Also, a nucleic acid encoding a sialyltransferase polypeptide or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding sialyltransferase polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired sialyltransferase polypeptide or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the sialyltransferase protein or a protein subsequence thereof by site-directed mutagenesis. The plasmid containing the sialyltransferase-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Some nucleic acids encoding sialyltransferase proteins can be amplified using PCR primers based on the sequence of previously identified sialyltransferase proteins, e.g., Cst-I, (see, e.g., U.S. Pat. No. 6,689,604); Cst-II, (see, e.g., U.S. Pat.

No. 6,503,744); and Cst-III. Examples of PCR primers that can be used to amplify nucleic acid that encode sialyltransferase proteins include the following primer pairs:

```
For Cst-I nucleic acids:

CJ18F: 5' (41 mer, NdeI site in italics)
                                        (SEQ ID NO: 21)
5' C TTA GGA GGT CAT ATG ACA AGG ACT AGA ATG GAA
AAT GAA C 3'
and CJ40R: 3' with 6 His tail (60 mer. SalI site in
italics, (His)₆ tag in bold)
                                        (SEQ ID NO: 22)
5' CC TAG GTC GAC TCA TTA GTG GTG ATG GTG GTG ATG
TTC CCC TTT CTC AAA CTC TCT CTT C 3';

For Cst-II nucleic acids:

CJ-131:
                                        (SEQ ID NO: 23)
5' CTTAGGAGGTCATATGAAAAAAGTTATTATTGCTGGAAATG 3'
and CJ-132:
                                        (SEQ ID NO: 24)
5' CCTAGGTCGACTTATTTTCCTTTGAAATAATGCTTTATATC 3';

For Cst-III nucleic acids:

CstH-5p:
                                        (SEQ ID NO: 25)
5' GGGGGGCATATGAGTATGAATATTAATGCTTTG 3'
and CstH-3p:
                                        (SEQ ID NO: 26)
5' GGGGGGGTCGACTCATTATCTATTTTTATTTGCATATTTTTC 3'
```

In some bacteria, nucleic acids encoding sialyltransferase protein can be isolated by amplifying a specific chromosomal locus, e.g., the LOS locus of C. jejuni, and then identifying a sialyltransferase typically found at that locus (see, e.g., U.S. Pat. No. 6,503,744). Examples of PCR primers that can be used to amplify an LOS locus comprising nucleic acids encoding sialyltransferase protein include the following primer pairs:

```
CJ42: Primer in heptosylTase-II
                                        (SEQ ID NO: 27)
5' GC CAT TAC CGT ATC GCC TAA CCA GG 3' 25 mer CJ43: Primer in heptosylTase-I
                                        (SEQ ID NO: 28)
5' AAA GAA TAC GAA TTT GCT AAA GAG G 3' 25 mer
```

Other physical properties of a recombinant sialyltransferase polypeptide expressed from a particular nucleic acid, can be compared to properties of known sialyltransferases to provide another method of identifying suitable sequences or domains of the sialyltransferase polypeptide that are determinants of acceptor substrate specificity and/or catalytic activity. Alternatively, a putative sialyltransferase polypeptide gene or recombinant sialyltransferase polypeptide gene can be mutated, and its role as a sialyltransferase, or the role of particular sequences or domains established by detecting a variation in the structure of a carbohydrate normally produced by the unmutated, naturally-occurring, or control sialyltransferase polypeptide. Those of skill will recognize that mutation or modification of sialyltransferase polypeptides of the invention can be facilitated by molecular biology techniques to manipulate the nucleic acids encoding the sialyltransferase polypeptides, e.g., PCR.

Functional domains of newly identified sialyltransferase polypeptides can be identified by using standard methods for mutating or modifying the polypeptides and testing them for activities such as acceptor substrate activity and/or catalytic activity, as described herein. The functional domains of the various sialyltransferase polypeptides can be used to construct nucleic acids encoding sialyltransferases and the functional domains of one or more sialyltransferase polypeptides. These multi-sialyltransferase fusion proteins can then be tested for the desired acceptor substrate or catalytic activity.

In an exemplary approach to cloning nucleic acids encoding sialyltransferase proteins, the known nucleic acid or amino acid sequences of cloned sialyltransferases are aligned and compared to determine the amount of sequence identity between various sialyltransferases. This information can be used to identify and select protein domains that confer or modulate sialyltransferase activities, e.g., acceptor substrate activity and/or catalytic activity based on the amount of sequence identity between the sialyltransferases of interest. For example, domains having sequence identity between the sialyltransferases of interest, and that are associated with a known activity, can be used to construct sialyltransferase proteins containing that domain, and having the activity associated with that domain (e.g., acceptor substrate specificity and/or catalytic activity).

V. Expression of Sialyltransferase Polypeptides in Host Cells

In preferred the tagged sialyltransferase polypeptides of the invention are expressed in *E. coli* host cells. In a further preferred embodiment, *E. coli* strains JM109 or BNN93 are used as host cells.

In another preferred embodiment, the pcWin2 expression vector is used to express the tagged sialyltransferase protein in an *E. coli* host cell. The pcWin2 vector is known. See, e.g., WO/2005/067601 (2005).

Sialyltransferase proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizoblum* sp., *Erwinia* sp., *Escherichia* sp. (e.g., *E. coli*), *Bacillus*, *Pseudomonas*, *Proteus*, *Salmonella*, *Serratia*, *Shigella*, *Rhizobia*, *Vitreoscilla*, *Paracoccus* and *Klebsiella* sp., among many others. The cells can be of any of several genera, including *Saccharomyces* (e.g., *S. cerevisiae*), *Candida* (e.g., *C. utilis*, *C. parapsilosis*, *C. krusei*, *C. versatilis*, *C. lipolytica*, *C. zeylanoides*, *C. guilliermondii*, *C. albicans*, and *C. humicola*), *Pichia* (e.g., *P. farinosa* and *P. ohmeri*), *Torulopsis* (e.g., *T. candida*, *T. sphaerica*, *T. xylinus*, *T. famata*, and *T. versatilis*), *Debaryomyces* (e.g., *D. subglobosus*, *D. cantarellii*, *D. globosus*, *D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia*, *Enterobacter*, *Azotobacter*, *Erwinia*, *Klebsielia*, *Bacillus*, *Pseudomonas*, *Proteus*, and *Salmonella*.

Once expressed in a host cell, the sialyltransferase polypeptides can be used to produced sialylated products. For example, the sialyltransferase polypeptides can be isolated using standard protein purification techniques and used in in vitro reactions described herein to make sialylated products. Partially purified sialyltransferase polypeptides can also be used in in vitro reactions to make sialylated products as can the permeabilized host cells. The host cells can also be used in an in vivo system (e.g., fermentative production) to produce sialylated products.

Typically, the polynucleotide that encodes the sialyltransferase polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res*. (1980) 8: 4057), the tac promoter (DeBoer, et al., *Proc. Natl. Acad. Sci. U.S.A*. (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of sialyltransferase proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol*.; Tabor et al. (1985) *Proc. Nat'l. Acad. Sci. USA* 82:1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111, A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer, resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and *Current Protocols in Molecular Biology*, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as BLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g. murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The sialyltransferase polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3:151). In embodiments in which the sialyltransferase polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the fusion proteins are fused to a subsequence of protein A or bovine serum albumin (BSA), for example, to facilitate purification, secretion, or stability.

More than one recombinant protein may be expressed in a single host cell by placing multiple transcriptional cassettes in a single expression vector, or by utilizing different selectable markers for each of the expression vectors which are employed in the cloning strategy.

VI. Purification of Tagged Sialyltransferase Polypeptides

The sialyltransferase proteins of the present invention can be expressed as intracellular proteins or as proteins that are secreted from the cell, and can be used in this form, in the methods of the present invention. For example, a crude cellular extract containing the expressed intracellular or secreted sialyltransferase polypeptide can used in the methods of the present invention.

Alternatively, the sialyltransferase polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182: *Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the sialyltransferases polypeptides of the invention, the nucleic acids that encode the proteins can also include a coding sequence for a second epitope or "epitope tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the sialyltransferases polypeptide of the invention, and corresponding detection systems are known to those of skill in the art, and several are commercially available (e.g., "FLAG" (Kodak, Rochester N.Y.): Another example of a suitable tag is a polyhistidine sequence, which is capable of binding to metal chelate affinity ligands. Typically, six adjacent histidines (SEQ ID NO:20) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468, 374, filed May 5, 2003, herein incorporated by reference in its entirety.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the sialyltransferase polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

Once purified, the tagged sialyltransferase proteins of the invention are typically stored at a low temperature, e.g., $-20°$ C. One way to increase the stability of and decrease aggregation of the tagged sialyltransferase proteins is to store the proteins in solutions that include relatively high concentrations of glycerol. For example, the tagged sialyltransferase proteins of the invention can be stored in solutions that comprise between 20% and 95% glycerol. For example the storage solutions can include, e.g., 20%, 25%, 30%, 35%, 40%, 45%, 50%, 55%, 60%, 65%, 70%, 75%, 80%, 85%, 90%, or 95% glycerol. In a preferred embodiment, the storage solution includes between 40% and 60% glycerol. In another preferred embodiment, the storage solution includes about 50% glycerol. In a further preferred embodiment, the storage solution includes 50% glycerol. If necessary, the purified tagged sialyltransferase proteins can be introduced to a buffer or storage solution that includes the desired concentration of glycerol. Those of skill are aware of methods to change buffers or storage solutions, e.g., size exclusion chromatography, dialysis, and filtration, e.g., tangential flow filtration. These methods of buffer exchange can be practiced at any step of the protein purification protocol, not only as a final step before storage of the purified protein.

VII. Fusion Sialyltransferase Proteins

In some embodiments, the recombinant cells of the invention express fusion proteins that have more than one enzymatic activity that is involved in synthesis of a desired sialylated oligosaccharide. The fusion polypeptides can be composed of, for example, a tagged sialyltransferase polypeptide that is joined to an accessory enzyme, e.g., CMP-sialic acid synthase. Fusion proteins can also be made using catalytic domains or other truncations of the enzymes. For example, a polynucleotide that encodes a sialyltransferase polypeptide can be joined, in-frame, to a polynucleotide that encodes an enzyme involved in CMP-sialic acid synthesis. The resulting fusion protein can then catalyze not only the synthesis of the activated sialic acid molecule, but also the transfer of the sialic acid moiety to the acceptor molecule. The fusion protein can be two or more sialic acid cycle enzymes linked into one expressible nucleotide sequence. The fusion sialyltransferase polypeptides of the present invention can be readily designed and manufactured utilizing various recombinant DNA techniques well known to those skilled in the art. Exemplary fusion proteins are described in PCT Patent Application PCT/CA98/01180, which was published as WO99/31224 on Jun. 24, 1999 and which discloses CMP-sialic acid synthase from *Neisseria* fused with an α2,3-sialyltransferase from *Neisseria*. Those of skill will recognize that many other CMP-sialic acid synthase polypeptides and sialyltransferases can be fused for use in the invention. In some embodiments, a CMP-sialic acid synthase from *Neisseria* is fused to a sialyltransferase from *C. jejuni*. The *C. jejuni* sialyltransferase (Cst) can be a CstI, CstII, or CstIII enzyme. A full-length or truncated version of the *C. jejuni* sialyltransferase polypeptide can be used in the fusion sialyltransferase protein. In some embodiments, more that one fusion sialyltransferase polypeptide is expressed in the cell.

In some embodiments, the recombinant cells of the invention express fusion proteins that have more than one enzymatic activity that is involved in addition of at least one additional sugar residue, e.g., a non-sialic acid residue. These fusion polypeptides can be composed of, for example, a catalytic domain of a glycosyltransferase, e.g., not a sialyltransferase, that is joined to a catalytic domain of an accessory enzyme. The accessory enzyme catalytic domain can, for example, catalyze a step in the formation of a nucleotide sugar which is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. The polypeptides of the present invention can be readily designed and manufactured utilizing various recombinant DNA techniques well known to those skilled in the art. Suitable fission proteins are described in PCT Patent Application PCT/CA98/01180, which was published as WO99/31224 on Jun. 24, 1999, and include e.g., a UDP glucose epimerase fused in frame to a galactosyltransferase.

VIII. Donor Substrates and Acceptor Substrates

Suitable donor substrates used by the tagged sialyltransferase polypeptides and other glycosyltransferases in the methods of the invention include, but are not limited to, UDP-Glc, UDP-GlcNAc, UDP-Gal, UDP-GalNAc, GDP-Man, GDP-Fuc, UDP-GlcUA, and CMP-sialic acid and other activated sialic acid moieties. Guo et al., *Applied Biochem. and Biotech.* 68: 1-20 (1997)

Typically, acceptor substrates include a terminal galactose residue for addition of a sialic acid residue by an α2,3 linkage. For addition of a sialic acid residue in an α2,8 linkage, a second sialic acid residue is linked to a first sialic acid by an α2,8 linkage. Examples of suitable acceptors include a terminal Gal that is linked to GlcNAc or Glc by a β1,4 linkage, and a terminal Gal that is β1,3-linked to either GlcNAc or GalNAc. Suitable acceptors, include, for example, galactosyl acceptors such as Galβ1,4GlcNAc, Galβ1,4GalNAc, Galβ1,3 GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)). The terminal residue to which the sialic acid is attached can itself be attached to, for example, H, a saccharide, oligosaccharide, or an aglycone group having at least one carbohydrate atom. In some embodiments, the acceptor residue is a portion of an oligosaccharide that is attached to a protein, lipid, or proteoglycan, for example.

Suitable acceptor substrates used by the sialyltransferase polypeptides c and methods of the invention include, but are not limited to, polysaccharides and oligosaccharides. For example, lactose can be sialylated to form a sialylactose, e.g. 3' sialylactose. The sialyltransferases described herein can also be used in multienzyme systems to produce a desired product from a convenient starting material.

Suitable acceptor substrates used by the sialyltransferase polypeptides and methods of the invention include, but are not limited to, proteins, lipids, gangliosides and other biological structures (e.g., whole cells) that can be modified by the methods of the invention. These acceptor substrates will typically comprise the polysaccharide or oligosaccharide molecules described above. Exemplary structures, which can be modified by the methods of the invention include any a of a number glycolipids, glycoproteins and carbohydrate structures on cells known to those skilled in the art.

Examples of suitable acceptor substrates used in sialyltransferase-catalyzed reactions, and examples of suitable acceptor substrates used in sialyltransferase-catalyzed reactions are described in Guo et al., *Applied Biochem. and Biotech.* 68: 1-20 (1997), but are not limited thereto.

The present invention provides sialyltransferase polypeptides that are selected for their ability to produce oligosaccharides, glycoproteins and glycolipids having desired oligosaccharide moieties. Similarly, if present, accessory enzymes are chosen based on an desired activated sugar substrate or on a sugar found on the product oligosaccharide.

For synthesis of glycoproteins, one can readily identify suitable sialyltransferase polypeptides by reacting various amounts of a sialyltransferase polypeptide of interest (e.g., 0.01-100 mU/mg protein) with a glycoprotein (e.g., at 1-10 mg/ml) to which is linked an oligosaccharide that has a potential acceptor site for glycosylation by the sialyltransferase of interest. The abilities of the recombinant sialyltransferases proteins of the present invention to add a sugar residue at the desired acceptor site are compared, and a sialyltransferase polypeptide having the desired property (e.g., acceptor substrate specificity or catalytic activity) is selected.

In general, the efficacy of the enzymatic synthesis of oligosaccharides, glycoproteins, and glycolipids, having desired sialylated oligosaccharide moieties, can be enhanced through use of recombinantly produced sialyltransferase polypetitides of the present invention. Recombinant techniques enable production of the recombinant sialyltransferase polypeptides in the large amounts that are required for large-scale in vitro glycoprotein and glycolipid modification.

In some embodiments, suitable oligosaccharides, glycoproteins, and glycolipids for use by the sialyltransferase polypeptides and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

Preferably, when the acceptor saccharide is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

In one embodiment the tagged sialyltransferase proteins of the invention are used to add sialic acid residues to a erythropoietin protein. The added sialic acid residues can be modified, e.g., a PEGylated sialic acid residue. The tagged sialyltransferase proteins can be purified before being used in a sialylation reaction. Enzymatic methods of adding sialic acids residues, including PEGylated sialic acid, to proteins such as erythropoietin, are disclosed in WO 2006/127910, which is herein incorporated by reference for all purposes.

IX. Production of Sialylated Products

Tagged sialyltransferase polypeptides can be used to make sialylated products in in vitro reactions mixes or by in vivo reactions, e.g., by fermentative growth of recombinant microorganisms that comprise nucleotides that encode tagged sialyltransferase polypeptides.

A. In Vitro Reactions

The sialyltransferase polypeptides can be used to make sialylated products in in vitro reactions mixes. The in vitro reaction mixtures can include permeabilized microorganisms comprising the sialyltransferase polypeptides, partially purified sialyltransferase polypeptides, or purified sialyltransferase polypeptides; as well as donor substrates acceptor substrates, and appropriate reaction buffers. For in vitro reactions, the recombinant glycosyltransferase proteins, such as sialyltransferase polypeptides, acceptor substrates, donor substrates and other reaction mixture ingredients are combined by admixture in an aqueous reaction medium. Additional glycosyltransferases can be used in combination with the sialyltransferase polypeptides, depending on the desired sialylated product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For fucosyltransferases, the pH range is preferably maintained from about 6.0 to 8.0. For sialyltransferases, the range is preferably from about 5.5 to about 8.0.

Enzyme amounts or concentrations are expressed in activity units, which is a measure of the initial rate of catalysis. One activity unit catalyzes the formation of 10 82 mol of product per minute at a given temperature (typically 37° C.) and pH value (typically 7.5). Thus, 10 units of an enzyme is a catalytic amount of that enzyme where 10 μmol of substrate are converted to 10 82 mol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the glycoprotein to be glycosylated. For large-scale preparations, the reaction will often be allowed to proceed for between about 0.5-240 hours, and more typically between about 1-18 hours.

B. In Vivo Reactions

The tagged sialyltransferase polypeptides can be used to make sialylated products by in vivo reactions, e.g., fermentative growth of recombinant microorganisms comprising the sialyltransferase polypeptides. Fermentative growth of recombinant microorganisms can occur in the presence of medium that includes an acceptor substrate and a donor substrate or a precursor to a donor substrate, e.g., sialic acid. See, e.g., Priem et al., *Glycobiology* 12:235-240 (2002). The microorganism takes up the acceptor substrate and the donor substrate or the precursor to a donor substrate and the addition of the donor substrate to the acceptor substrate takes place in the living cell. The microorganism can be altered to facilitate uptake of the acceptor substrate, e.g., by expressing a sugar transport protein. For example, where lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of sialylated products is enhanced by manipulation of the host microorganism. For example, in *E. coli*, break down of sialic acid can be minimized by using a host strain that is lack CMP-sialate synthase (NanA-). (In *E. coli*, CMP-sialate synthase appears to be a catabolic enzyme.) Also in *E. coli*, when lactose is, for example, the acceptor saccharide or an intermediate in synthesizing the sialylated product, lactose breakdown can be minimized by using host cells that are LacZ-. Methods for in vivo synthesis of oligosaccharides, including oligosaccharides containing sialic acid are found in, e.g., Samain and Priem WO/2001/004341 (2001) and Johnson et al. WO/2006/034225 (2006).

C. Characterization of and Isolation of Sialylated Products

The production of sialylated products can be monitored by e.g., determining that production of the desired product has occurred or by determining that a substrate such as the acceptor substrate has been depleted. Those of skill will recognize that sialylated products such as oligosaccharide, can be identified using techniques such as chromatography, e.g., using paper or TLC plates, or by mass spectrometry, e.g., MALDI-TOF spectrometry, or by NMR spectroscopy. Methods of identification of sialylated products are known to those of skill in the art and are found, e.g., in U.S. Pat. No. 6,699,705, which is herein incorporated by reference for all purposes and in Varki et al., *Preparation and Analysis of Glycoconjugates*, in Current Protocols in Molecular Biology, Chapter 17 (Ausubel et al. eds, 1993).

In some embodiments, the tagged sialyltransferase polypeptides and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the preselected saccharide residue is linked to at least about 30% of the potential acceptor sites of interest. More preferably, the preselected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the preselected saccharide residue attached to the acceptor substrate of interest), the recited percentages include such pre-attached saccharide residues.

The term "altered" refers to the glycoprotein or glycolipid of interest having a glycosylation pattern that, after application of the sialyltransferase polypeptides and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are sialyltransferase polypeptides and methods of using such proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the sialyltransferase polypeptides and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 30%, 40%, 50%, 60%, 70%, and even still more preferably is at least 80%, 90%, or 95%.

The products produced using sialyltransferase polypeptides can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Example 1

Construction of CSTII Expression Vectors

The *Campylobacter* sialyltransferase II (CSTII) nucleic acid was isolated from plasmid pcWori/CSTII. See, e.g., Gilbert, et al., *J. Biol. Chem.*, 275: 3896-3906 (2000). Host *E. coli* cells were grown on 250 mL of Martone L-Broth with 10 mg/ml ampicillin for approximately 16 hr. Cells were then harvested by centrifugation at 5000 RPM for 15 minutes at 4° C. The plasmid DNA was isolated as described in the manual accompanying the Qiagen HiSpeed Plasmid Maxi Kit.

Using the PCR technique, a BamHI site was added immediately before the initiating ATG of CstII. Double STOP codons followed by an XhoI site were introduced at the 3' end of the CstII gene. The protein encoded by this construct encompasses the natural protein sequence for Cst-II with three additional amino acids (MGS) at the amino terminus (SEQ ID NO:2). After subcloning the BamHI-XhoI fragment into the pcWin2 expression vector, competent *E. coli* cells (TOP10 cells, Invitrogen) were transformed with the ligation mixture.

Transformants were selected on Martone LB agar plates containing 50 micrograms/mL of kanamycin. Colonies were selected from the kanamycin plates and were grown in liquid medium with kanamycin. Plasmid DNA was isolated using a Qiagen Qiaprep Miniprep kit. Plasmid DNA was incubated with restriction digest enzymes NdeI and XhoI, both from New England Biolabs. The digested DNA was analyzed on an agarose gel to determine the restriction pattern of the plasmid. A plasmid with the expected restriction pattern for insertion of CSTII to pcWin2 was selected and sequenced on both strands, confirming the expected CSTII nucleic acid sequence.

Figure 1:
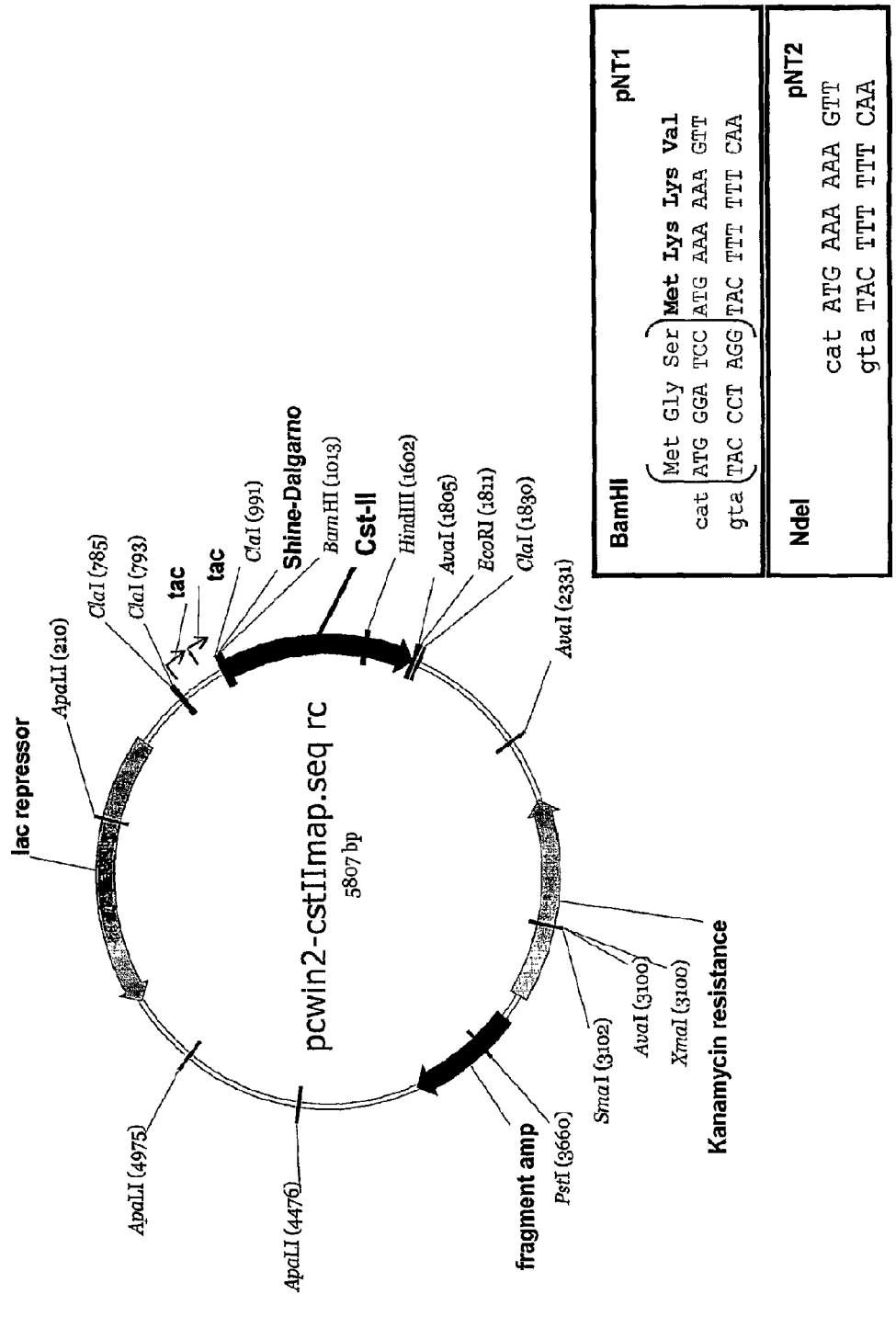

A second CSTII plasmid (pNT2) was constructed to remove the upstream initiation codon. pNT2 was generated from pNT1 using PCR and the appropriate primers. The sequence of pNT2 was determined by double stranded sequencing. The 540 CSTII nucleic acid sequences of pNT1 and pNT2 are shown in FIG. 1, as are the N-terminal amino acid sequences.

Example 2

Expression of CSTII Protein

CSTII protein expression from plasmids pNT1 and pNT2 was tested by growing transformed BNN93 cells on a 10 L scale and isolating protein from the cells. Expression plasmid pNT2 did not express CSTII protein. Expression plasmid pNT1 did express CSTII protein. (Data not shown.) The sequence of the CSTII protein expressed from plasmid pNT1 was analyzed. The expressed CSTII protein begins with MGS MKK (SEQ ID NO:29) and also expresses stably as with either GSMKK (SEQ ID NO:30) and MKK at the N-terminus of the protein as confirmed by N-terminal protein sequencing.

Fermentation conditions for improved expression of CSTII from pNT1 were determined. Parameters tested included: 1) Fermentation in simple media (designated E1.0) or rich media (designated E6.0); 2) *E. coli* K-12 host cell line selection using strains JM109 or BNN93 transformed pNT1; and 3) Mode of dissolved oxygen (DO) regulation during fermentation.

An inoculation culture of *E. coli* cells transformed with pNT1 was grown in soy LB medium with kanamycin. The inoculation culture was used to inoculate a ten liter production culture of, e.g., simple or rich media. Bacterial growth was monitored by reading the optical density of the culture at 600 nm.

When the OD600 of the production culture was between 0.6 and 1.0, CSTII expression was induced by addition IPTG to reach a final concentration of 1.0 mM IPTG. The induced cultures were incubated overnight at 37° C. for a total incubation of twenty-four hours. Fifty or two hundred mL aliquots were removed from the production cultures beginning four hours after addition of IPTG and continued at intervals until the final harvest.

At harvest, the final OD of the *E. coli* cultures was measured. The *E. coli* cells were harvested from the production culture by centrifugation at 5000 rpm for twenty minutes. Supernatants were discarded; the cell pellets were weighed and stored at –80° C.

The pellets were thawed and resuspended in 20 mM Tris HCl, pH 8.5 at a ratio of 10.0 mL/g wet weight. The cells were disrupted by two passages through an ice-packed Microfluidizer at 14,000PSI. Lysed cells were centrifuged at 5000 RPM for 20 minutes. The supernatants were separated from the pellets and 1.0 ml of supernatant was filtered through a 0.2 micron syringe filter. The filter lysed cells were used for both SDS-PAGE analysis and enzyme activity determinations.

Protein samples were run on Nu-Page gels using Novex pre-cast 12% Bis-Tris-gels in Novex XCELL. Samples were prepared by mixing 25 microliters of protein solution with 25 microliters of 2× loading buffer and 4 microliters of 1M DTT followed by heating at 98° C. for 6 minutes. Ten microliters from each sample were loaded onto the gel and run at a constant voltage of 120V. The electrophoresis run was stopped when marker dye reached the bottom of the gel. Gels were washed with water twice for one minute each time and then microwaved for one minute under high power. Gels were stained with Simply Blue Safestain by microwaving for one minute at high power followed by incubation for fifteen minutes at room temperature with gentle shaking. The gel was destained with water to clarify the background.

A capillary electrophoresis (CE) based enzyme assay was used to measure activity of the expressed CSTII. The acceptor substrate was FCHASE [(6-Fluorescein-5-Carboxamido) Hexanoic Acid Succimidyl Ester] labeled siallyllactose. The donor substrate was CMP-NeuAc. The enzymatic assay was known. See, e.g., Wakarchuk, W. W. and Cunningham, A. M., *Methods Mol. Biol.*, 213:263-274 (2003)). After reaction was stopped, the mixture was diluted and directly applied to capillary electrophoresis monitored by an LIF (laser induced fluorescence) detector. The product was eluted one-half minute later than the acceptor and the result is calculated and expressed as Unit/liter. The control assay included the mix of reagent buffers without enzyme

CONCLUSIONS

A tagged (MGS) CSTII protein was expressed form expression plasmid pNT1. A non-tagged CSTII protein was not expressed from expression plasmid pNT2. Using the pNT1 expression vector CSTII from *Campylobacter jejuni* was produced in *E. coli* strains JM109 and BNN93. CSTII production was determined both by analysis of protein expression and enzymatic activity.

Higher levels of CSTII activity was obtained using rich medium as compared to simple medium. Enzyme activity values ranged from 200-500 U/Liter of E6.0 fermentation media, while E1.0 production media gave 100 U/Liter of fermentation media.

Higher levels of CSTII activity was obtained in the *E. coli* host strain BNN93 as compared to the JM109 strain. Enzyme activity values ranged from 200-300 Units/Liter of fermentation media for JM109, in E6.0 media, as compared to 200-500 U/Liter of fermentation media for BNN93 cells in E6.0 media.

Fermentation of *E. coli* expressing CSTII with the stir to airflow cascade priority gave a higher titer of enzyme activity (500 U/L as compared to 360 U/L) and was less problematic in terms of foaming than the airflow to stir cascade mode for regulating dissolved oxygen.

Example 3

Purification of CSTII Protein Expressed from pNT

*E. coli* cells that express the pNT1 plasmid were grown as above and then harvested by centrifugation and stored at −80° C. Cell pellets thawed and resuspended in 50 mM Tris, 5 mM EDTA, pH 8.3, (10 mL/g). The cell pellets were homogenized with two passes through a microfluidizer. The lysate was centrifuged at 15,00033 G for twenty minutes and the supernatent was passed through a 0.2 um filter. The lysate was used for the purification methods described below. An exemplary purification protocol is provided in FIG. 4.

Methods

Protein Concentration Determination (A280). The protein concentration was determined using a spectrophotometer at a fixed absorbance of 280 nm (A280). Prior to the A280 measurement, the spectrophotometer was zeroed (autozero) using the appropriate buffer. The protein concentration was determined using an extinction coefficient of 1 AU=1.012 mg CST-II.

SDS-PAGEAnalysis. Invitrogen 4-20% Tris Glycine gels were used. All samples were prepared under reducing conditions (mixed 1:1 with SDS Sample Buffer containing 0.1 M DTT), (Non-reducing gels: sample was mixed 1:1 with SDS Sample Buffer containing no DTT). All samples were heated at 85° C. for 5 min unless otherwise specified. Gels were run at a constant voltage of 200V for 60 min. After electrophoresis, the proteins were stained with a Simply Blue Safe stain solution for 60 min. Silver stained gels were prepared using the Wako Silver stain kit following the manufacturer's protocol. See Blue Plus 2 molecular weight marker was used as a standard on each gel, containing: myosin (250 kDa), phosphorylase (148 kDa), BSA (98 kDa, glutamic dehydrogenase (64 kDa), alcohol dehydrogenase (50 kDa), carbonic anhydrase (36 kDa), lysozyme (22 kDa), aprotinin (6 kDa), and insulin B-chain (4 kDa). The protein bands were visualized and scanned with an HP Scanjet 7400 C, and the image of the gel was optimized with the HP Precision Scan Program.

Protein Purity by HPLC. Protein purity was determined by C3 RP HPLC chromatography (Zorbax 300SB-C3, 150×2.1 mm, 5 μm) using the following two solutions; A, 0.1% TFA in water, and B, 0.09% TFA in ACN. The mobile phase was run as a gradient from 40-60% B over 20 min at 0.5 mL/min at 40° C. The column was re-equilibrated by running the gradient from 95-40% B over 1 min, and then isocratic for 10 min.

bCST-II Enzyme Activity Assay. Clarified CST-II homogenate samples (10 mcL) were typically diluted with 50 mM HEPES, 0.02% Tween-20, pH 7.5 (Dilution Buffer) for activity assay (~1/120 to 1/140:10 mcL homogenate+1190 mcL Dilution Buffer or 10 mcL+1390 meL Dilution Buffer). Purified CST-II samples (10 mcL) were diluted to 0.08-0.012 mg protein/mL with Dilution Buffer. Diluted CST-II enzyme samples were assayed according to the previously described CST-II assay protocol (see Neose Research Report, Capillary Electrophoresis Based Sialyltransferase Assay to Monitor CST-II Enzyme Activity, Feb. 17, 2006).

Cell Disruption by Microfluidization. Cell pellets from BNN93 CST-II fermentation harvests were stored at −80° C. In initial experiments, the cell pellet was resuspended in 20 mM Tris, pH 8.3 (1 g/7.5 mL buffer). All subsequent experiments utilized 5 mM or 10 mM EDTA in 50 mM Tris, pH 8.3. Upon resuspension, the pellet was homogenized with two passes over a microfluidizer set at 16,000-18,000 PSI. The system was rinsed with an additional 2.5 mL of buffer per gram of pellet to collect any material that remained in the system after the cell pellet homogenization was completed. The final homogenate concentration was 1 g cell pellet/lb mL buffer.

Clarification. The BNN93 cell homogenate was immediately centrifuged at 12000×G for 60 minutes on a centrifuge equipped with a fixed angle rotor (Sorval) at 4° C. The supernatant was filtered using an AcroPak-20 filter (0.2 micron). The filtered homogenate was stored only briefly at 4° C. until purification.

Amino Acid N-terminal Sequencing Purified CST-II samples were analyzed by N-terminal sequencing for the first 10 (or more) amino acids. Purified CST-II was mixed 1:1 with SDS Tris-Glycine sample buffer with or without any reducing agent (DTT) and was heat denatured at 85° C. for 6 minutes. The denatured sample was loaded onto multiple lanes of 4-20% SDS Tris-Glycine gels. The gels were run under reducing or non-reducing, denaturing conditions at 125 V for 118 min. and were left unstained for electroblotting to a PVDF membrane. The SDS-PAGE gels were electroblotted using a Biorad Mini Trans-Blot Cell. The transfer buffer was 10 mM CAPS (pH=11.0) with 10% methanol. The proteins were transferred to an Applied Biosystems ProBlott PVDF membrane with 0.1-0.2 82 m pore size. The transfer was run for 158 minutes at 110 Volts for each gel. The transferred bands were visualized with Coomassie Blue protein stain. The bands were excised from the PVDF membranes for sequence analysis on an Applied Biosystems Procise 492HT Amino Acid Sequencer. The samples were analyzed with a pulse-liquid PVDF method. The data was analyzed with SequencPro version 2.1 software supplied by Applied Biosystems.

Table 12 provides the results of amino acid sequencing of purified CST-II protein. The figure demonstrates that the majority of the CST-II protein began GSMK. . . (SEQ ID NO:38), starting with the glycine residue of the MGS tag. A small amount of the purified CST-II protein began with the native MKK. . . sequence.

Analysis of Multiple CST-II HPLC Peaks. Isolation of CST-II Fractions from RP-HPLC. The CST-II fractions were isolated by RP-HPLC using conditions described herein. Fractions were collected from four injections (total ~100 µg CST II). Each fraction was concentrated by SpeedVac, reducing the volume by half and removing most of the acetonitrile. A small portion (~5%) of the remaining volume was analyzed on RP-HPLC to compare the profile of the purified fraction to that of the starting material. The remaining samples were lyophilized to dryness. Since fraction 3 was not apparently enriched adequately after the first isolation, it was re-purified by dissolving the lyophilized material in water, injecting it all on RP-HPLC, and collecting fraction 3 again. A small portion of the re-purified fraction 3 was diluted with water and analyzed by RP-HPLC. The remaining re-purified fraction 3 was lyophilized to dryness. The lyophilized fractions were then analyzed by QToF MS (as described below) and SDS-PAGE.

Q-ToF MS Analysis. The protein sample CST-II was injected for RP-HPLC/q-ToF MS analysis without prior sample preparation. An LC-Packings (Sunnyvale, Calif.) microcapillary system was used for injection and chromatography analysis. A Famos™ microinjection autosampler injected 1.3 microliters of the sample. Solvents A (0.1% (v/v) formic acid in H2O) and B (0.1% (v/v) formic acid in Acetonitrile) were used as eluants. An Ultimate™ capillary pump set a flow rate of 4 microliters/minute and pumped a gradient starting from 25% B to 95% B in 43 minutes. A QStar-XL (Applied Biosystems, Foster City, Calif.) mass spectrometer was connected on-line to the LC-Packings system. It was operated in standard, positive-ion mode with an electrospray ionization (ESI) source. The time-of-flight (TOF) analyzer acquired an m/z range of 400 to 3000. The raw data for the intact protein was deconvoluted within Analyst QSTM software over a mass range of 25000 Da to 35000 Da. Endotoxin Determination. Endotoxin contamination was determined using Limulus Amebocyte Lysate (LAL) assay (BioWhittaker, Kinetic-QCL Kit, Cat#: 50-650 U) (Neose QC160). Briefly, the LAL reaction is enzyme mediated assay, and endotoxin catalyzes the activation of a proenzyme in the LAL. The initial rate of activation is determined by the concentration of endotoxin present. The activated enzyme catalyzes the release of p-nitroaniline (pNA) from the colorless substrate Ac-Ile-Ala-Arg-pNA. The pNA release is measured photometrically at 405 nm. The concentration of endotoxin in a sample is calculated from its reaction time by comparison to the reaction time of solutions containing known amounts of endotoxin standard.

Anion Exchange Chromatography.

Figure 5:
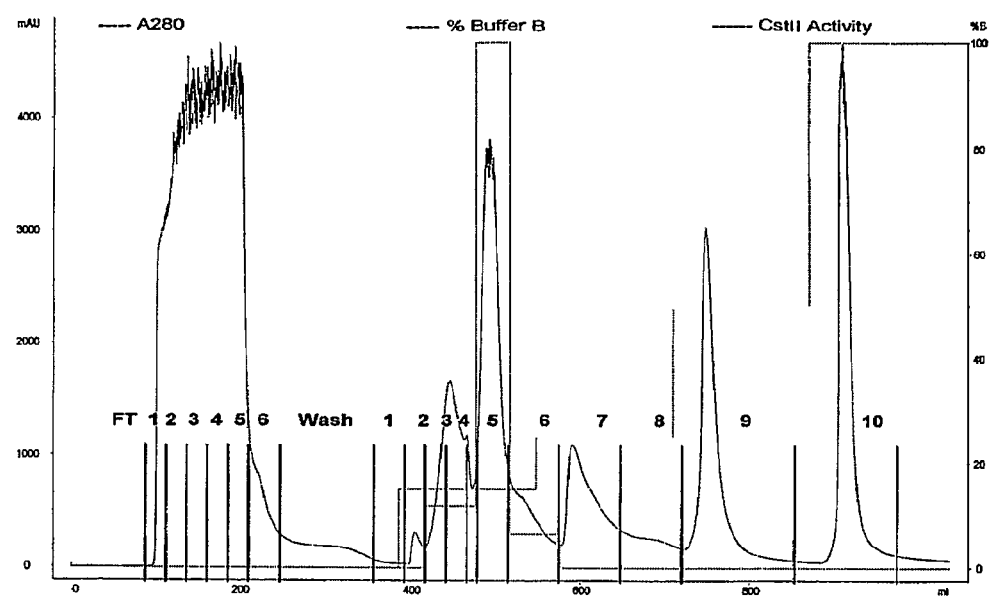

Q-SEPHAROSE™ Chromatography—Step Gradient. An XK26 chromatography column was packed with Q-SEPHAROSE™ Fast Flow resin (Q-FF) (40 mL) and attached to an AKTA Explorer 100 LC system continuously monitoring absorbance at 280 nm. The column was equilibrated with 5 column volumes (CV) 20 mM Tris, pH 8.3 (Buffer A). Clarified E. coli homogenate containing CST-II (a 13 g cell pellet prepared as described above without addition of EDTA, 130 mL) was loaded onto the prepared column at a flow rate of 115 cm/hr. Unbound material was washed from the column using 5 CV of Buffer A. The CST-II was eluted at a flow rate of 115 cm/hr with the following step gradient using Buffer B (1 M NaCl in Buffer A): 4 CV at 15% Buffer B, 4 CV at 25% Buffer B, 4 CV at 50% Buffer B (FIG. 5). Fractions were sampled for SDS-PAGE analysis and CST-II enzyme activity assay (FIGS. 5 and 6). The purified CST-II activity was found in the 15% B elution step. CST-II-containing fractions were pooled, formulated with 50% glycerol and stored at −20° C. to preserve activity.

Q-SEPHAROSE™ Chromatography—Step Gradient (No Dilution of the Loading Solution). An XK16 chromatography column was packed with Q-SEPHAROSE™ Fast Flow (Q-FF) resin (20 mL) and attached to an AKTA Explorer 100 LC system continuously monitoring absorbance at 280 nm. The column was equilibrated with 5 column volumes (CV) 50 mM Tris, pH 8.3 (Buffer A). The conductivity of the clarified E. coli homogenate containing CST-II (a 2 g cell pellet as prepared above containing 5 mM EDTA, 20 mL) was 4.66 ms/cm and the sample loaded onto the prepared column at a flow rate of 115 cm/hr. Unbound material was washed from the column with 5 CV Buffer A. The CST-II was eluted at a flow rate of 115 cn/hr with the following step gradient using Buffer B (1 M NaCl in Buffer A): 5 CV at 15% Buffer B, 5 CV at 100% Buffer B (FIG. 7A). Fractions were analyzed by SDS-PAGE and the CST-II enzyme activity assay (FIGS. 7A and 8, Table 1). The purified CST-II activity was found in the 15% B elution step. CST-II-containing fractions were pooled, formulated with 50% glycerol and stored at −20° C. to preserve activity.

TABLE 1

Recovery of CST-II Enzyme Activity from Q-SEPHAROSE ™ FF.

| Q-SEPHAROSE ™ Elution | Load (Units) | FT/Wash (Units) | Elution (Units) | Elution (mg Protein) | Specific Activity (U/mg protein) | Recovery (%) |
|---|---|---|---|---|---|---|
| Step Gradient (Undiluted Load Solution) | 40.8 | 12.7 | 19.5 | 154.5 | 0.126 | 47.8 |
| Step Gradient (Diluted Load Solution) | 40.8 | 4.6 | 27.6 | 194 | 0.142 | 67.6 |
| Linear Gradient (Diluted Load Solution) | 40.8 | 4.6 | 13.1 | 93.4 | 0.149 | 32.1 |

Recovery; Total units CST-II recovered from column divided by the total units in the clarified homogenate loaded .times. 100.
FT = Flow Through.

Q-SEPHAROSE™ Chromatography—Step Gradient (Dilution of the Loading Solution).

An XK16 chromatography column was packed with Q-SEPHAROSE™ Fast Flow (Q-FF) resin (20 mL) and attached to an AKTA Explorer 100 LC system continuously monitoring absorbance at 280 nm. The column was equilibrated with 5 column volumes (CV) 50 mM Tris, pH 8.3 (Buffer A). The conductivity of clarified E. coli homogenate containing CST-II (a 2 g cell pellet prepared as described above with 5 mM EDTA, 20 mL) was 4.66 ms/cm. The clarified homogenate was diluted 1:1 with Buffer A (20 mL), the conductivity was 3.3 ms/cm, and the sample loaded onto the prepared column at a flow rate of 115 cm/hr. Unbound material was washed from the column with 5 CV Buffer A. The CST-II was eluted at a flow rate of 115 cm/hr with the following step gradient with Buffer B (1 M NaCl in Buffer A): 5 CV at 15% Buffer B, 5 CV at 100% Buffer B (FIG. 7B). Fractions were analyzed by SDS-PAGE and the CST-II enzyme activity assay (FIGS. 7B and 8, Table 1). The purified CST-II activity was found in the 15% B elution step. CST-II containing fractions were pooled, formulated with 50% glycerol and stored at −20° C. to preserve activity.

Q-SEPHAROSE™ Chromatography—Linear Gradient. An XK16 chromatography column was packed with Q-SEPHAROSE™ Fast Flow (Q-FF) resin (20 mL) and attached to an AKTA Explorer 100 LC system continuously monitoring absorbance at 280 nm. The column was equilibrated with 5 column volumes (CV) 50 mM Tris, pH 8.3 (Buffer A). The conductivity of clarified *E. coli* homogenate containing CST-II (a 2 g cell pellet prepared as described above with 5 mM EDTA, 20 mL) was m 4.66 ms/cm. The clarified homogenate was diluted 1:1 with Buffer A (20 mL), the conductivity was 3.3 ms/cm, and the sample loaded onto the prepared column at a flow rate of 115 cm/hr. Unbound material was washed from the column with 5 CV Buffer A. The CST-II was eluted at a flow rate of 115 cm/hr with the following linear gradient with Buffer B (1 M NaCl in Buffer A): 0-15% Buffer B over 10 CV followed by 5 CV at 100% Buffer B (FIG. 9). Fractions were analyzed by SDS-PAGE and the CST-II enzyme activity assay. CST-II containing fractions were pooled, formulated with 50% glycerol and stored at −20° C. to preserve activity.

Q-SEPHAROSE™ results. Q-SEPHAROSE™ FF was evaluated as an initial CST-II capture step. CST-II bound effectively to Q-SEPHAROSE™ and could be eluted using a step gradient (NaCl). The purified enzyme lacked many of the *E. coli* proteins present in the crude homogenate. When low concentrations of EDTA were used to reduce proteolysis, dilution of the loading solution was required to reduce the conductivity and to maximize the binding capacity of the Q-SEPHAROSE™ resin. A linear gradient elution with NaCl could also be used to purify the CST-II on Q-SEPHAROSE™. Chromatography using source 15Q resin was also effective (chromatogram not shown).

Cation Exchange Chromatography.

SP-SEPHAROSE™ High Performance (HP) Chromatography—pH 6.8. An XK16 chromatography column was packed with SP-SEPHAROSE™ HP resin (20 mL) and attached to an AKTA Explorer 100 LC system continuously monitoring absorbance at 280 nm. The column was equilibrated with 5 column volumes (CV) 25 mM sodium phosphate, pH 6.8 (Buffer A).

A sample of CST-II partially purified by Q-SEPHAROSE™ and stored at −20° C. (24 mL, A280: 0.434 AU, 50% glycerol) was diluted with 24 mL of 100 mM sodium phosphate, pH 6.8 to adjust the pH and then further diluted with 2.5 mM sodium phosphate, pH 6.8 (82 mL) to reduce the conductivity to 3.8 ms/cm (A280:0.855 AU). The conditioned sample was filtered using a 250 mL Nalgene filter (0.2 micron) and was loaded onto the prepared column at a flow rate of 150 cm/hr and washed with buffer A until the absorbance at 280 nm returned to baseline values. The CST-II was eluted at 80 cm/hr with a gradient with Buffer B (1 M NaCl in Buffer A): 0-100% Buffer B over 10 CV (FIG. 10). Fractions were analyzed by SDS-PAGE (FIG. 1). CST-II-containing fractions were pooled, formulated with 50% glycerol and stored at −20° C. to preserve activity.

SP-SEPHAROSE™ HP Chromatoaraphy—pH 6.0. An XK16 chromatography column was packed with SP-SEPHAROSE™ HP resin (20 mL) and attached to an AKTA Explorer 100 LC system continuously monitoring absorbance at 280 nm. The column was equilibrated with 5 column volumes (CV) 25 mM MES, pH 6.0 (Buffer A). A sample of CST-II partially purified by Q-SEPHAROSE™ and stored at −20° C. (20 mL, A280:0.434 AU, 50% glycerol) was diluted with 20 mL of 100 mM MES, pH 6.0 to adjust the pH and then further diluted with 25 mM MES, pH 6.0 (40 mL) to reduce the conductivity to 2.4 ms/cm (A280:1.20 AU). The conditioned sample was filtered through a 250 mL Nalgene filter unit (0.2 micron) and was loaded onto the prepared column at a flow rate of 150 cm/hr and washed with Buffer A until the absorbance at 280 nm returned to baseline values. The CST-II was eluted at 80 cm/hr with a gradient with Buffer B (1 M NaCl in Buffer A): 0-100% Buffer B over 10 CV (FIG. 12). Fractions were analyzed by SDS-PAGE (FIG. 13). CST-II containing fractions were pooled, formulated with 50% glycerol and stored at −20° C. to preserve activity.

Results of Cation Exchange Chromatography. SP-SEPHAROSE™ HP was evaluated as a second chromatography step to follow the Q-SEPHAROSE™ FF purification. This step was introduced to eliminate the *E. coli* impurities (Glyceraldehyde-3-phosphate dehydrogenase and osmotically inducible protein: resistance protein, N-terminal sequencing results not shown) (FIGS. 12 and 13). Very little binding of the CST-II was observed to the SP resins using chromatography conditions of pH 6.8 even though this pH was below the theoretical pI of CST-II (7.5). CST-II effectively bound to the SP resin at pH 6.0 in 25 mM MES buffer and could be eluted using a salt gradient.

Hydroxyapatite Purification Step.

Hydroxyapatite Type I (40 micron) Chromatography (1 mL). A Tricorn 5 column was packed with Hydroxyapatite Type I resin (40 micron) (1 mL) and attached to an AKTA Explorer 100 LC system continuously monitoring absorbance at 280 nm. The column was equilibrated with 5 CV5 nM sodium phosphate, pH 6.5 (Buffer A). A sample of CST-II that had been partially purified by Q-SEPHAROSE™ and SP-SEPHAROSE™ HP and stored at −20° C. (1 mL, 50% glycerol, A280:1.22 AU) was diluted with 5 mM sodium phosphate, pH 6.5 (3 mL). The sample was loaded onto the prepared column at 153 cm/hr (0.5 mL/min). Unbound material was washed from the column with 10 CV Buffer A. The CST-II was eluted with a gradient of Buffer B (1.5 M NaCl in Buffer A): from 0-100% B over 20 CV (FIG. 14A). Fractions were sampled for SDS-PAGE (FIG. 15). CST-II-containing fractions were pooled and formulated with 50% glycerol and stored at −20° C. to preserve activity.

Hydroxyapatite Type II (40 micron) Chromatography (1 mL). A Tricorn 5 column was packed with Hydroxyapatite Type II resin (40 micron) (1 mL) and attached to an AKTA Explorer 100 LC system continuously monitoring absorbance at 280 nm. The column was equilibrated with 5 CV5 mM sodium phosphate, pH 6.5 (Buffer A). A sample of CST-II that had been partially purified by Q-SEPHAROSE™ and SP-SEPHAROSE™ HP and stored at −20° C. (1 mL, 50% glycerol, A280:1.22 AU) was diluted with 5 mM sodium phosphate, pH 6.5 (3 mL). The sample was loaded onto the prepared column at 153 cm/hr (0.5 mL/min). Unbound material was washed from the column with 10 CV Buffer A. The CST-II was eluted with a gradient of Buffer B (1.5 M NaCl in Buffer A): from 0-100% B over 20 CV (FIG. 14B). Fractions were analyzed by SDS-PAGE (FIG. 15). CST-II-containing fractions were pooled, formulated with 50% glycerol and stored at −20° C. to preserve activity.

Hydroxyapatite Type II (40 micron) Chromatography (10 mL). An XK16 column was packed with Hydroxyapatite Type II resin (40 micron) (10 mL) and attached to an AKTA Explorer 100 LC system continuously monitoring absorbance at 280 .mu.m. The column was equilibrated with 5 CV5 mM sodium phosphate, pH 6.5 (Buffer A). A sample of CST-II that had been partially purified by Q-SEPHAROSE™ and stored at −20° C. (30 mL, 50% glycerol, A280:5.56 AU) was diluted with 5 mM sodium phosphate, pH 6.5 (120 mL). The pH was adjusted to 6.0 with 1 M HCl and then filtered through a Nalgene filter unit (0.2 micron). The sample (150 mL, conductivity: 1.65 ms/cm, A280:1.043) was loaded onto the prepared column at 119 cm/hr (4 mL/min). Unbound material was washed from the column with 5 CV Buffer A until the absorbance at 280 nm reached baseline values. The CST-II was eluted with a gradient of Buffer B (1.5 M NaCl in Buffer A): from 0-100% B over 20 CV, followed by 5 CV of 500 mM sodium phosphate, pH 6.5 (FIG. 16). Fractions were analyzed by SDSPAGE (FIG. 17). CST-II-containing fractions were pooled, formulated with 50% glycerol and stored at −20° C. to preserve activity.

Results of Hydroxyapatite (HA) Chromatography. Hydroxyapatite (HA) chromatography, type I or type II, was used to purify CST-II. The Type II resin offered slightly better resolution and removed some of the other major E. coli impurities that had co-eluted on Q-SEPHAROSE™ (Oligopeptide transport: periplasmic binding protein, N-terminal sequencing results not shown).

Hydrophobic Interaction Chromatography (HIC).

CST-II Peed Conditioning. CST-II, partially purified by Q-SEPHAROSE™, formulated with 50% glycerol and stored at −20° C. was used for these experiments. CST-II purified by Q-SEPHAROSE™ (1 mL) was diluted into 2 M NaCl, 25 mM Tris-HCl, pH 7.2 (Buffer B, 14 mL) and concentrated to 0.1 mL in a Centricon Plus-20 (5000 Da MWCO) centrifugal filter. The CST-II was diluted again with Buffer B (10 mL) and concentrated to 0.2 mL. The concentrated CST-II was diluted with Buffer B (0.8 mL) to a final volume of 1.0 mL (A280:4.23 mg).

Phenyl SEPHAROSE™ (High sub) Chromatography. A prepacked Phenyl SEPHAROSE™ high sub column (1 mL, GE Healthcare) was connected to a Varian HPLC system that monitored the absorbance at 280 nm. The column was washed with 30 mL 25 mM Tris-HCl, pH 7.2, (Buffer A) and equilibrated with 50 mL 2 M NaCl, 25 mM Tris-HCl, pH 7.2 (Buffer B) at a flow rate of 0.5 mL/min. The conditioned, Q-SEPHAROSE™ purified CST-II (1.0 mL as described above) was loaded onto the prepared column. The column was washed for 10 minutes with Buffer B (5 CV) at 0.5 mL/min to remove unbound material. Bound protein was eluted using the following gradient: 10-40 min, 100-0% B; 40-60 min, 100% Buffer A. Five fractions were collected and analyzed by SDS-PAGE (FIGS. 18-19). Fractions were stored at 4° C.

Phenyl SEPHAROSE™ (Low sub) Chromatography. A prepacked Phenyl SEPHAROSE™ low sub column (1 mL, GE Healthcare) was connected to a Varian HPLC system that monitored the absorbance at 280 nm. The column was washed with 30 mL 25 mM Tris-HCl, pH 7.2 (Buffer A), and equilibrated with 50 mL 2 M NaCl, 25 mM Tris-HCl, pH 7.2 (Buffer B) at a flow rate of 0.5 mL/min. The conditioned, Q-SEPHAROSE™ purified CST-II (1.0 mL as described above) was loaded onto the prepared column. The column was washed for 10 min with Buffer B (5 CV) at a flow rate of 0.5 mL/min to remove unbound material. Bound protein was eluted using the following gradient: 10-25 min, 100-0% Buffer B; 25-50 min, 100% Buffer A. Five fractions were collected and analyzed by SDS-PAGE (FIGS. 20-21). Fractions were stored at 4° C.

Phenyl SEPHAROSE™ (Low sub) Chromatography with 20% Ethylene Glycol. A prepacked Phenyl SEPHAROSE™ low sub column (1 mL, GE Healthcare) was connected to a Varian HPLC system that monitored the absorbance at 280 nm. The column was washed with 25 mM Tris-HCl, pH 7.2, 20% ethylene glycol (Buffer A, 30 mL), and equilibrated with 67% Buffer B (3 M NaCl, 25 mM Tris-HCl, pH 7.2) in Buffer A (50 mL) at a flow rate of 1.0 mL/min. The conditioned, Q-SEPHAROSE™-purified CST-II (1.0 mL as described above) was loaded onto column. The column was washed and eluted using the following gradient: 0-10 min, 67% Buffer B in 25 mM Tris-HCl with 20% ethylene glycol, pH 7.2 (Buffer A); 10-25 min, 67-0% Buffer B; 25-50 min, 100% Buffer A. Four fractions were collected and analyzed by SDS-PAGE (FIGS. 22-23). Fractions were stored at 4° C.

Butyl SEPHAROSE™ Chromatography with 20% Ethylene Glycol. A prepacked Butyl SEPHAROSE™ column (1 mL, GE Healthcare) was connected to a Varian HPLC system that monitored the absorbance at 280 nm. The column was washed with 25 mM Tris-HCl, pH 7.2, 20% ethylene glycol (Buffer A, 30 mL), and equilibrated with 50% Buffer B (3 M NaCl in 25 mM Tris-HCl, pH 7.2) in Buffer A (50 mL) at a flow rate of 1.0 mL/min. The conditioned Q-SEPHAROSE™-purified CST-II (1 mL as described above) was injected onto column. The column was washed and the product eluted using the following gradient: 0-10 min, 50% Buffer B in 25 mM Tris-HCl with 20% ethylene glycol, pH 7.2 (Buffer A); 10-20 min, 50-0% Buffer B; 20-30 min, Buffer A. Two fractions were collected and analyzed by SDS-PAGE (FIGS. 24-25). Fractions were stored at 4° C.

Results of Hydrophobic Interaction Chromatography (HIC). Phenyl SEPHAROSE™ chromatography (HIC) was evaluated as an alternative to the hydroxyapatite or SP-SEPHAROSE™ HP purification steps. Initial experiments with phenyl SEPHAROSE™ (high substitution) revealed that CST-II bound very tightly and was not readily eluted. When phenyl SEPHAROSE™ (low substitution) was used the recovery was only slightly better, but the material that was eluted was highly purified. Addition of 20% ethylene glycol to the HIC elution buffer greatly improved the recovery of CST-II while maintaining the purification resolution (FIGS. 20 and 21). Butyl SEPHAROSE™ provided even better recoveries and purification of the CST-II when 20% ethylene glycol was used in the elution buffer.

Other Purification Methods

Effects of Buffer Excipients on CST-II Stability During Cellulose Acetate Filtration. CSTII purified by Q-SEPHAROSE™ was buffer exchanged using cellulose acetate centrifugal filters in the presence of a panel of excipients and monitored for evidence of loss of protein or aggregation by measuring the absorbance at 280 nm and % transmittance at 600 nm. CST-II purified by Q SEPHAROSE™ (5.2 mL, 25 mM Tris, 100 mM NaCl, 50% glycerol, pH 8.3, A280:0.909 AU) was diluted with 50 mM sodium phosphate, pH 6.5 (5.2 mL) and the pH was adjusted to 6.5 with 3 drops of 1 M monobasic sodium phosphate. The absorbance at 280 nm and % transmittance at 600 nm of the pH-adjusted CST-II solution was measured using a spectrophotometer (GE Healthcare). The CST-II solution was divided into 10 aliquots (1 mL). Each CST-II aliquot was diluted with 3 mL of one of the following ten excipient solutions: 1. 0.01 M NaCl, 0.01 M sodium phosphate, pH 6.5; 2. 0.1 M NaCl, 0.01 M sodium phosphate, pH 6.5; 3. 0.2 M NaCl, 0.01 M sodium phosphate, pH 6.5; 4. 0.5 M sucrose, 0.01 M NaCl, 0.01 M sodium phosphate, pH 6.5; 5. 0.1 M mannitol, 0.01 M NaCl, 0.01 M sodium phosphate, pH 6.5; 6. 0.1 M mannitol, 0.5 M sucrose, 0.01 M NaCl, 0.01 M sodium phosphate, pH 6.5; 7. 10% v/v glycerol, 0.01 M NaCl, 0.01 M sodium phosphate, pH 6.5; 8. 0.1 M sorbitol, 0.01 M NaCl, 0.01 M sodium phosphate, pH 6.5; 9. 0.02% TWEEN®-20, 0.01 M NaCl, 0.01 M sodium phosphate, pH 6.5; 10. 0.1 M trehalose, 0.01 M NaCl, 0.01 M sodium phosphate, pH 6.5.

The diluted CST-II solutions were each concentrated to 0.5 mL using separate Amicon Ultra 4 (10 kDa MWCO) centrifugal filters at 4° C. The concentrated samples (0.5 mL) were rediluted with the corresponding buffer (0.5 mL) and concentrated again to 0.5 mL. The samples were rediluted (0.5 mL) and concentrated (0.5 mL) again two more times for a total of 4 concentration steps. The final CST-II solution in the filters was removed, each filter washed with their respective buffer (0.5 mL), combined and the final CST-II solution volume adjusted to exactly 1.0 mL with the appropriate buffer. Each sample was measured immediately for % Transmittance (600 nm) and then centrifuged at 5000.times.G for 20 min (4° C.) to settle any particulate matter. The absorbance of each solution was measured at 280 nm using the corresponding buffer as a blank for each reading (% T600 and A280) (Table 2). The absorbance (280 nm) of each excipient solution was measured against water as a control. Each centrifuged CST-II solution was analyzed by SDS-PAGE (30 mcL) (FIG. 26). Effects of Buffer Excipients on CST-II Stability during Polyethersulfone (Biomax) Filtration. CST-II purified by Q-SEPHAROSE™ was buffer exchanged using polyethersulfone (PES, Biomax) centrifugal filters in the presence of selected excipients (see below) and monitored for evidence of loss of protein or aggregation by measuring the absorbance at 280 nm and % transmittance at 600 nm. CST-II purified by Q-SEPHAROSE™ (4.5 mL, 25 mM Tris, 100 mM NaCl, 50% glycerol, pH 8.3, A280:0.909 AU) was diluted with 50 mM sodium phosphate, pH 6.5 (4.5 mL) and the pH was adjusted to 6.5 with 3 drops of 1 M monobasic sodium phosphate. The absorbance at 280 nm and % transmittance at 600 nm of the pH adjusted CST-II solution was measured. Aliquots of the pH-adjusted CST-II solution (2.0 mL) were diluted with 4.0 mL of one of the following excipient solutions (6.0 mL total volume) in Centricon Plus-20 (Biomax 5, 5000 Da MWCO) centrifugal filters: 1. 0.01 M sodium phosphate, 0.01 M NaCl, pH 6.5; 2. 0.02% TWEEN®-20, 0.1 M NaCl, 0.01 M sodium phosphate, pH 6.5; 3. 0.5 M sucrose, 0.02% TWEEN®-20, 0.1 M NaCl, 0.01 M sodium phosphate, pH 6.5. The diluted CST-II solutions were concentrated to approximately 2 mL each at 4° C. The concentrated samples (2 mL) were rediluted with the corresponding buffer (2 mL) and concentrated again to 2 mL. The samples were rediluted and concentrated again two more times for a total of 4 concentration steps. During the final concentration step, the samples were concentrated to about 0.5 mL and the retentate was removed from the unit. The Centricon units were rinsed with approximately 1.5 mL of the appropriate buffer and the rinsings were pooled with the concentrated solutions to give a final measured volume of 2.0 mL. The % Transmittance (600 nm) and absorbance (280 nm) of each concentrated solution and buffer control was measured exactly as described above (Table 3).

TABLE 2

Effects of Excipients on the Recovery of CST-II using Cellulose Acetate Centrifugal Filters.

| Condition* | Excipient A280 | Buffer Exchanged CST-II | | |
|---|---|---|---|---|
| | | % T600 | A280 | Recovery (%) |
| Buffer | 0.000 | 96.6 | 0.143 | 33.5 |
| 0.1M NaCl | −0.029 | 97.8 | 0.163 | 38.2 |
| 0.2M NaCl | −0.021 | 99.4 | 0.149 | 34.9 |
| 0.5M Sucrose | 0.001 | 94.2 | 0.181 | 42.4 |
| 0.1M Mannitol | 0.004 | 96.0 | 0.144 | 33.7 |
| 0.5M Sucrose + 0.1M Mannitol | 0.012 | 95.6 | 0.186 | 43.6 |
| 10% Glycerol | −0.030 | 96.4 | 0.169 | 39.6 |
| 0.1M Sorbitol | 0.085 | 94.8 | 0.160 | 37.5 |
| 0.02% TWEEN ® 20 | −0.022 | 98.0 | 0.221 | 51.8 |
| 0.1M Trehalose | 0.059 | 97.4 | 0.581 | 136 |

Absorbance (280 nm) and % Transmittance (600 nm) readings were taken after CST-II (purified by Q-SEPHAROSE ™) concentration/buffer exchange into 10 mM sodium phosphate, 10 mM sodium chloride, pH 6.5 buffer containing the excipient shown. The corresponding excipient solution was used as a blank for each A280 and % T600 reading on the spectrophotometer.
Excipient A280: Absorbance (280 nm) of the excipient solution vs. the 10 mM sodium phosphate, 10 mM sodium chloride, pH 6.5.
Recovery (%) calculated as absorbance (280 nm) value divided by the absorbance (280 nm) of the CST-II before concentration/buffer exchange × 100.

TABLE 3

Effects of Excipients on the Recovery of CST-II using Polyethersulfone (Biomax) Centrifugal Filters.

| Condition | % T600 | A280 | Recovery (%) |
|---|---|---|---|
| Buffer | 97.2 | 0.139 | 32.3 |
| 0.1 M NaCl, 0.02% TWEEN ® 20 | 98.2 | 0.18 | 41.8 |
| 0.1 M NaCl, 0.02% TWEEN ® 20, 0.5 M Sucrose | 97.6 | 0.185 | 43 |

Absorbance (280 nm) and % Transmittance (600 nm) readings were taken after CST-II (purified by Q SEPHAROSE ™) concentration/buffer exchange into 10 mM sodium phosphate, 10 mM sodium chloride, pH 6.5 buffer containing the excipient shown. The corresponding excipient solution was used as a blank for each A280 and % T600 reading on the spectrophotometer.
Recovery (%) calculated as absorbance (280 nm) value divided by the absorbance (280 nm) of the CST-II before concentration/buffer exchange × 100.

Effects of Dialysis on CST-II Stability. CST-II purified by Q-SEPHAROSE™ was buffer exchanged by dialysis and monitored for evidence of loss of protein by measuring the absorbance at 280 nm. Two aliquots of Q-SEPHAROSE™ purified CST-II (1.0 mL, 25 mM Tris, 100 mM NaCl, 50% glycerol, pH 8.3, A280:0.909 AU) were diluted with either 10 mM sodium phosphate, 10 mM NaCl, pH 6.5 (1 mL) or 10 mM Tris-HCl, 10 mM NaCl, pH 8.5 (1.0 mL). The absorbance (280 nm) of each solution was measured using a spectrophotometer (GE Healthcare). Each diluted CST-II solution was injected into a SLIDE-A-LYZER® dialysis cassette (3500 Da MWCO, Pierce) according to the manufacturer's instructions. The cassettes were dialyzed against the corresponding buffers for 8 hr with gentle stirring at 4° C. The dialyzed CST-II samples were removed from the SLIDE-A-LYZER® cassettes and the volume, absorbance (280 nm) and % transmittance (600 nm) were measured. The protein concentrations and total protein mass were calculated. The amount of CST-II recovered from this process was determined by dividing the protein mass from the dialyzed CST-II solution by that of the original diluted CST-II solution (Table 4).

TABLE 4

Recovery of CST-II Enzyme Activity
after Dialysis at pH 6.5 and 8.5.

| Dialysis Condition | Pre-Dialysis | | Post Dialysis | | | |
|---|---|---|---|---|---|---|
| | Volume (mL) | A280 | Volume (mL) | % T600 | A280 | Recovery (%) |
| pH 6.5 | 2 | 0.438 | 3.7 | 98.2 | 0.157 | 66.3 |
| pH 8.5 | 2 | 0.456 | 3.8 | 97.2 | 0.162 | 67.5 |

Absorbance at 280 nm and % transmittance at 600 nm were measured after concentration/buffer exchange of CST-II (purified by Q-SEPHAROSE ™). The corresponding dialysis buffer was used as a blank for each A280 and % T600 reading on the spectrophotometer.
Recovery (%) calculated as (absorbance at 280 nm value multiplied by the volume after dialysis) divided by (the absorbance (280 nm) multiplied by the concentration before dialysis) × 100.

Combination of Methods

Small scale purifications of CST-II were performed to determine which combination of the purification methods (Q-SEPHAROSE™ FF-gradient elution, Hydroxyapatite Type II (40 micron), and SP-SEPHAROSE™ HP chromatographies) performed best. After the Q-SEPHAROSE™ chromatography step, the same purity of CST-II could be attained by combining hydroxyapetite and SP-SEPHAROSE™ in any order (data not shown)

Figure 4:
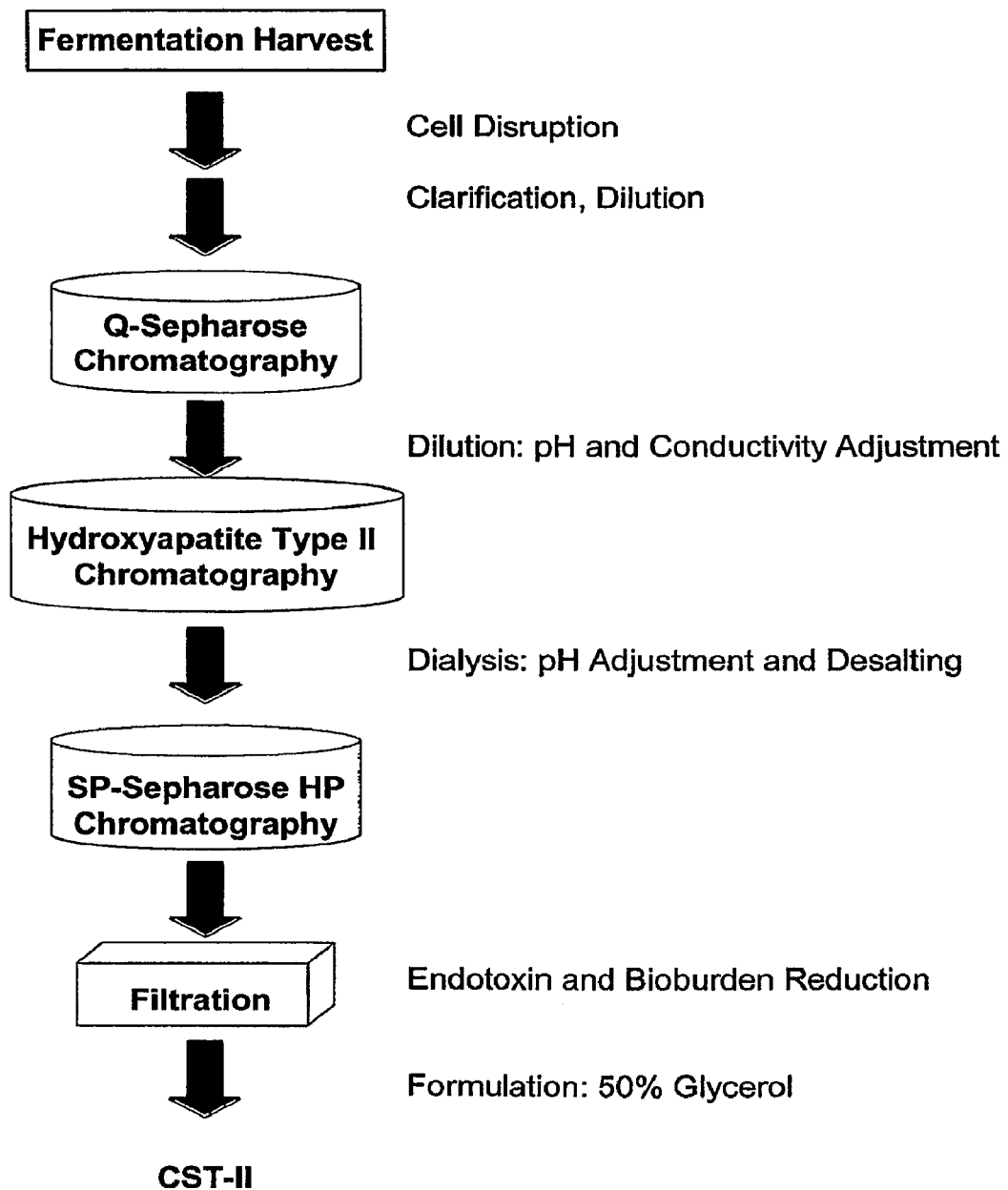

A complete small scale purification process of CST-II was then performed using Q-SEPHAROSE™ FF-gradient elution, Hydroxyapatite Type II (40 micron), and SP-SEPHAROSE™ HP chromatographies as shown in FIG. 4, except that between each chromatography step, the CST-II was buffer exchanged and/or concentrated using centrifugal filters as necessary to prepare for the next chromatography. The CST-II was assayed for activity and the protein concentration measured by A280 at each stage (Tables 5 and 6). This process afforded a high purity CST-II, however, the overall recovered enzyme activity and mass recoveries were extremely low as a result of a low recovery from the gradient elution of the Q SEPHAROSE™ chromatography combined with protein losses during the buffer exchange and concentration steps (Table 6). In addition, a white precipitate was observed during loading of the hydroxyapatite column that resulted in significant back pressure. A brief study to determine methods to prevent the CST-II loss resulting from protein aggregation or denaturation during these process steps was undertaken.

TABLE 5

Process Development Results of the Preliminary
CST-II Purification Process.

| Process Step | Step Recovery (%) | Overall Recovery (%) |
|---|---|---|
| Harvest | 100% | 100% |
| Q-SEPHAROSE ™ | 16.2 | 16.2 |
| Hydroxyapatite Type II | 5.8* | 0.93* |
| SP-SEPHAROSE ™ HP/Final Formulation | 56.2 | 2.3 |

Step Recovery (%): calculated as total units CST-II in the fraction pool divided by the total units CST-II in the Elution Fraction of the prior step × 100. Overall Recovery (%) calculated as total CST-II activity (units) recovered from purification step divided by total units at start of process (cell homogenate) × 100.
*The high sodium chloride concentration in Hydroxyapatite elution pool inhibits the CST-II activity assay giving inaccurate results. The enzyme concentration was not high enough (due to the low recovery) to successfully reduce the salt concentration by dilution and obtain an accurate CST-II activity value.

TABLE 6

Mass Recovery of CST-II after Buffer Exchange/Concentration
Steps between Chromatographies from the Preliminary Process.

| Buffer Exchange of Elution Pool | Step Recovery (%) |
|---|---|
| Harvest | na |
| Q-SEPHAROSE ™ Elution Pool Buffer Exchange | 45 |
| Hydroxyapatite Type II Elution Pool Buffer Exchange | 87 |
| SP SEPHAROSE ™ HP Elution Pool Buffer Exchange | 72 |

Determined the amount of protein lost during the conditioning (buffer exchange/concentration) of CST-II in preparation to load on the next column.
Step Recovery: Total mg protein recovered from a buffer exchange/concentration step divided by the total units CST-II before buffer exchange/concentration × 100.

CST-II purified by Q-SEPHAROSE™ FF was concentrated and buffer exchanged using two different types of centrifugal filter membranes (cellulose acetate and polyether sulfone). Excipients were added to the buffers to determine if these reagents were capable of preventing or reducing the loss of CST-II protein during this process as judged by absorbance measurements (280 nm) and SDS PAGE (Tables 2 and 3 and FIG. 26). Trehalose (0.1 M trehalose) appeared promising although a potential absorbing (280 nm) contaminant made the interpretation difficult. TWEEN®-20 was the most beneficial excipient, although a significant loss of CST-II was still observed (by absorbance at 280 nm).

Dialysis was evaluated as an alternative to buffer exchange using centrifugal filters. Two buffers were tested and for both, the recoveries of CST-II (partially purified by Q-SEPHAROSE™ ) were greater than 66% (based on absorbance at 280 nm) (Table 4). These results were far superior to the typical recoveries for centrifugal filtration units (33%), therefore, dialysis was chosen as a substitute process for any buffer exchange step.

Although the recovery of enzyme activity for the dialysis and centrifugal filtration experiments were not obtained, the observed decrease in overall protein amount, as reflected by the absorbance readings at 280 nm, are consistent with the loss of CST-II protein and enzyme activity during the small scale purification of enzyme (Table 6). Protein was lost during the concentration and filtration steps and was observed on the filtration membranes as a white floculant precipitate (tangential flow filtration, data not shown). This loss significantly decreased the overall CST-II recovery (Table 5).

Production of CST-II (Small Scale)

Cell Disruption by Microfluidization. Cell Pellet from BNN93 CST-II fermentation harvest (10 g, stored at −80° C.) was homogenized in 50 mM Tris, 10 mM EDTA, pH 8.3 and clarified as previously described. The homogenate was divided into two 50 mL samples. Tween-20 (0.02%) was added to one of the 50 mL homogenate samples and the other was left untreated.

Clarification. BNN93 cell homogenates (2.times.50 mL) were immediately centrifuged at 15000.times.G for 20 minutes on a centrifuge equippend with a fixed angle rotor (Sorval) at 4° C. The supernatants were filtered using 75 mm Nalgene filter (from a 1 L filter unit, 0.2 micron) and collected into a 150 mL Nalgene bottle. The filtered homogenate samples were kept at 4° C. briefly until purification on Q-SEPHAROSE™ FF.

Q-SEPHAROSE™ Chromatography using a Step Gradient (No TWEEN®-20). An XK26 chromatography column was packed with Q-SEPHAROSE™ FF resin (50 mL) and attached to an AKTA Explorer 100 LC system continuously monitoring absorbance at 280 nm. The column was equilibrated with 5 column volumes (CV) 50 mM Tris, pH 8.3

(Buffer A). The clarified *E. coli* homogenate containing CST-II (a 5 g cell pellet was prepared as described above containing 10 mM EDTA, 50 mL) was diluted with Buffer A (150 mL) and the conductivity was measured (3.12 ms/cm). The sample was loaded onto the column at a flow rate of 113 cm/hr (10 mL/min). Unbound material was washed from the column with 5 CV Buffer A. The CST-II was eluted at a flow rate of 113 cm/hr (10 mL/min) with the following step gradient with Buffer B (1 M NaCl in Buffer A): 4 CV at 15% Buffer B, 4 CV at 100% Buffer B (FIG. 27). Fractions were sampled for SDS-PAGE (FIG. 28). The purified CST-II was found in the 15% Buffer B elution step. Fractions containing CST-II were pooled and a 0.5 mL sample was formulated with 50% glycerol and stored at −20° C. to preserve activity.

Q-SEPHAROSE™ Chromatography using a Step Gradient (with TWEEN®-20). An XK26 chromatography column was packed with Q-SEPHAROSE™ FF resin (50 mL) and attached to an AKTA Explorer 100 LC system continuously monitoring absorbance at 280 nm. The column was equilibrated with 5 column volumes (CV) 50 mM Tris, pH 8.3 containing 0.005% TWEEN®-20 (Buffer A). Clarified *E. coli* homogenate containing CST-II (a 5 g cell pellet was prepared as described above containing 10 mM EDTA, 50 mL) and TWEEN®-20(0.02%) was diluted with Buffer A (150 mL) and the conductivity measured (3.12 ms/cm). The diluted CST-II was loaded onto the prepared column at a flow rate of 113 cm/hr (10 mL/min). Unbound material was washed from the column with 5 CV Buffer A. The CST-II was eluted at a flow rate of 113 cm/h (10 mL/min) with the following step gradient with Buffer B (1 M NaCl in Buffer A): 4 CV at 15% Buffer B, 4 CV at 100% Buffer B (FIG. 27). Fractions were analyzed by SDS-PAGE (FIG. 26). The purified CST-II was found in the 15% B elution step. CST-II containing fractions were pooled and a 0.5 mL sample was formulated with 50% glycerol and stored at −20° C. to preserve activity. The remainder of the CST-II fraction pool was stored at 4° C. prior to further purification on Hydroxyapatite Type II chromatography.

Hydroxyapatite Type II Chromatography (40 micron) (with TWEEN®-20). An XK16 column was packed with Hydroxyapatite Type II resin (40 micron) (10 mL, 6.0 g) and attached to an AKTA Explorer 100 LC system continuously monitoring absorbance at 280 nm. The column was equilibrated with 5 CV 5 mM sodium phosphate, pH 6.5 containing 0.005% TWEEN® 20 (Buffer A). A 5.0 mL sample of CST-II that had been partially purified by Q-SEPHAROSE™ containing TWEEN® 20, see above, (FIG. 27, Fraction 1) and stored at 4° C. was slowly diluted into 50 mM sodium phosphate, pH 6.5 (5 mL) while monitoring pH. The pH was adjusted from 6.8 to 6.5 with an additional 0.5 mL of the 50 mM sodium phosphate buffer, pH 6.5. The sample (10.5 mL) was further diluted with 10 mM sodium phosphate, pH 6.5 containing 0.005% TWEEN®-20 (29.5 mL) to reduce the phosphate concentration. The diluted CST-II was filtered through a 0.2 micron filter, the pH and conductivity were measured (pH 6.53, 4.99 ms/cm, A280=1.022 AU) and the solution was loaded onto the prepared column at 120 cm/hr (4 mL/min). Unbound material was washed from the column with 5 CV Buffer A. The CST-II was eluted with a gradient of Buffer B (1.5 M NaCl in Buffer A): from 0-100% Buffer B over 25 CV, followed by 5 CV of 500 mM sodium phosphate, pH 6.5 (FIG. 29). Fractions were analyzed by SDS-PAGE (FIG. 30). CST-II-containing fractions were pooled and a 0.5 mL sample was formulated with 50% glycerol and stored at −20° C. to preserve activity. The remainder of the CST-II fraction pool was stored at 4° C. prior to further purification on SP-SEPHAROSE™ HP.

Hydroxyapatite Type II Chromatography (20 micron) (with TWEEN®-20). An XK16 column was packed with Hydroxyapatite Type II resin (20 micron) (10 mL, 6.0 g) and attached to an AKTA Explorer 100 LC system continuously monitoring absorbance at 280 nm. The column was equilibrated with 5 CV 5 mM sodium phosphate, pH 6.5 containing 0.005% TWEEN® 20 (Buffer A). A 5.0 mL sample of CST-II that had been partially purified by Q-SEPHAROSE™ containing TWEEN®-20, see above, (FIG. 27, Fraction 1) and stored at 4° C. was slowly diluted into 50 mM sodium phosphate, pH 6.5 (5 mL) while monitoring pH. The pH was adjusted from 6.8 to 6.5 with an additional 0.5 mL of the 50 mM sodium phosphate buffer, pH 6.5. The sample (10.5 mL) was further diluted with 10 mM sodium phosphate, pH 6.5 containing 0.005% TWEEN®-20 (29.5 mL) to reduce the phosphate concentration. The diluted CST-II was filtered through a 0.2 micron filter, the pH and conductivity were measured (pH 6.53, 4.99 ms/cm, A280=1.022 AU) and the solution was loaded onto the prepared column at 120 cm/hr (4 mL/min). Unbound material was washed from the column with 5 CV Buffer A. The CST-II was eluted with a gradient of Buffer B (1.5 M NaCl in Buffer A): from 0-100% Buffer B over 25 CV, followed by 5 CV of 500 mM sodium phosphate, pH 6.5 (FIG. 29). Fractions were analyzed by SDS-PAGE (FIG. 30). CST-II-containing fractions were pooled and a 0.5 mL sample was formulated with 50% glycerol and stored at −20° C. to preserve activity. The remainder of the CST-II fraction pool was stored at 4° C. prior to further purification on SP-SEPHAROSE™ HP.

SP-SEPHAROSE™ HP Chromatography—pH 6.0 (40 micron HA fractions). An XK16 chromatography column was packed with SP-SEPHAROSE™ HP resin (10 mL) and attached to an AKTA Explorer 100 LC system continuously monitoring absorbance at 280 nm. The column was equilibrated with 5 column volumes (CV) 25 mM MES, pH 6.0 containing 0.005% TWEEN® 20 (Buffer A). A sample of CST-II partially purified by Q-SEPHAROSE™ and Hydroxyapatite Type II (40 micron) stored at 4° C., see above, (35 mL, 0.005% TWEEN®-20) was adjusted to 0.02% TWEEN®-20 and dialyzed overnight against 25 mM MES, 10 mM NaCl, pH 6.0 (4 L, conductivity: 1.91 ms/cm) in Snakeskin dialysis tubing at 4° C. (see above). The dialyzed sample was filtered through a 50 mL Tube Top filter (0.2 micron) and the final volume was 42.3 mL, pH 6.0, conductivity: 3.6 ms/cm, A280:0.261.

The filtered sample was loaded onto the prepared column at a flow rate of 120 cm/hr (4 mL/min) and washed with 5 CV Buffer A. The CST-II was eluted at 120 cm/hr (4 mL/min) with a gradient with Buffer B (1 M NaCl in Buffer A): 0-50% Buffer B over 15 CV, held at 50% Buffer B for 1 CV and then any tightly bound material was eluted with 5 CV of 100% Buffer B (FIG. 31). Fractions were analyzed by SD S-PAGE (FIG. 30). Fractions containing CST-II were pooled and a 0.5 mL sample was formulated with 50% glycerol and stored at −20° C. to preserve activity. The remainder of the CST-IT fractions pool (25 mL) was formulated.

SP-SEPHAROSE™ HP Chromatography—pH 6.0 (20 micron HA fractions). The CST-II purified by HA type II (20 micron) chromatography was purified using SP-SEPHAROSE™ HP in the same manner as described above (SP-SEPHAROSE™ HP chromatography—20 microns) (FIG. 31). The fractions containing the CST-II were combined after analysis by SDS PAGE (FIG. 30). The pooled product fractions were formulated as described below.

Formulation of CST-II. The remainder of the CST-II fraction pools (25 mL, each) from the SP-chromatography steps, see above, were concentrated to 5 mL in an Amicon Ultra-15

(10 kDa MWCO) spin concentrator and diluted with Formulation Buffer (25 mM MES, 200 mM NaCl, pH 6.0, 10 mL) and reconcentrated to a final volume of 5 mL, each. The buffer exchanged CST-II pools were filtered through MUSTANG® E Acrodisc units that had been preconditioned with Formulation Buffer. After filtration the filters were rinsed with an additional 1.5 mL of Formulation buffer and the filtrates were pooled and diluted with equal volumes of glycerol (6.5 mL, each) to yield CST-II in a final formulations of 12.5 mM MES, 100 mM NaCl, 0.0125% TWEEN®-20, pH 6.0. The samples were stored immediately at −20° C.

Results of production of CST-II (small scale). A purification scheme was developed based on the results of the process steps described above. These include the use of Q-SEPHAROSE™ FF, hydroxyappetite type II and SP-SEPHAROSE™ chromatographies to purify CST-II (FIG. 4). A small scale test purification process was performed to determine the process durability and determine product recoveries. The CST-II was homogenized in Tris buffer at pH 8.3 with 10 mM EDTA and clarified in the presence and absence of TWEEN®-20. The CST-II was captured on Q-SEPHAROSE™ (with and without TWEEN®-20) and eluted with the NaCl step gradient to maximize recovery (FIGS. 27 and 28).

The partially purified CST-II pool containing TWEEN®-20 was diluted, split and purified over either an Hydroxyapatite Type II (40 micron) or a Hydroxyapatite Type II (20 micron) resin (FIGS. 29 and 30). The 20 micron resin was found to provide slightly improved resolution between the CST-II and a closely eluting 60 kDa E. coli protein impurity (oligopeptide transport: periplasmic binding protein, N-terminal sequencing result not shown). The 40 micron and 20 micron hydroxyapatite pools were individually dialyzed and purified over SP SEPHAROSE™ HP (FIGS. 30 and 31). The CST-II recoveries were both estimated to be approximately 22% based on enzyme activity.

Analysis of CST-II During Purification

CST-II Proteolysis. Attempted Separation of Proteolytic Fragments by Size Exclusion (SEC). A sample of CST-II purified (Q-SEPHAROSE™ Hydroxyapatite Type II, and SP-SEPHAROSE™ HP) and formulated as described above (250 mcL, 711 mcg of protein) was injected onto a SUPERDEX™ 200 10/30GL column attached to an AKTA Explorer 100 LC system continuously monitoring absorbance at 280 nm. The sample was chromatographed with 50 mM sodium phosphate, 150 mM NaCl, pH 7.2 at a flow rate of 0.5 mL/min (FIG. 32). Fractions were analyzed by SDS-PAGE (FIG. 33).

Test for Proteolytic Activity. CST-II was collected after each chromatography step from the small scale process described above (Q-SEPHAROSE™, HA-Type II (20 micron), and SP SEPHAROSE™ HP) and were stored immediately with 50% glycerol in elution buffer at −20° C. in the following buffers; 1. Q-SEPHAROSE™, 25 mM Tris-HCl, 75 mM NaCl, 50% glycerol, pH 8.3; 2. HA-Type II (20 micron), 5 mM sodium phosphate, 550 mM NaCl, 50% glycerol, pH 6.5; and, 3. SP-SEPHAROSE™ -HP, 12.5 mM MES, 85 mM NaCl, 50% glycerol, pH 6.0. Each sample (10 mcg each) was incubated 14 hr at 32° C. and analyzed by SDS-PAGE to determine if additional proteolysis of the CST-II was observed relative to samples stored at −20° C. (FIG. 34).

Prevention of CST-II Proteolysis During Cell Pellet Homogenation. Samples of cell pellet (2.0 g each) from BNN93 CST-II fermentation harvest (stored at −80° C.) were resuspended in one of the following test buffers (20 mL): Condition 1. 50 mM Tris-HCl, pH 8.3; Condition 2. 50 mM Tris-HCl, 10 mM EDTA, pH 8.3; Condition 3. 50 mM MES, pH 6.0; Condition 4. 50 mM sodium acetate, pH 4.0; Condition 5. 50 mM Tris-HCl, pH 8.3 with 500 uL Calbiochem Protease Inhibitor Cocktail Set II (containing 20 mM AEBSF, 1.7 mM Bestatin, 200 micromolar E-64, 85 mM EDTA, 2 mM Pepstatin).

Cells were microfluidized and clarified as previously described. Samples of the clarified homogenates were filtered through Pall syringe filters (0.2 micron) and injected onto a SUPERDEX™ 200 10/30GL column that had been previously equilibrated with the corresponding homogenization buffer for each sample containing also 150 mM NaCl. The samples were chromatographed on an AKTA Explorer 100 LC system continuously monitoring absorbance at 280 nm (FIG. 35). The CST-II peak pools were collected and analyzed by SDS-PAGE (FIG. 36).

Results of CST-II characterization. CST-II is a tetrameric protein. N-terminal sequencing confirmed that two protein species were purified from the BNN93 cell fermentation: the expected 260 amino acid (MKK . . . NINF)(SEQ ID NO:5; SEQ ID NO:31) species, and a 262 amino acid (GSMKK . . . NINF)(SEQ ID NO:15) species thought to arise from alternate initiation of translation of the pNTI expression vector. The ratio of the GSMKK (262 amino acid)(SEQ ID NO:15) species to the MKK (260 amino acid)(SEQ ID NO:5) species in the purified protein was found to be approximately 90:10.

Analysis of CST-II Proteolysis. During the development of a purification process, proteolysis of CST-II was observed. Analysis of these fragments by N-terminal sequencing and LC/Q-ToF MS confirmed the presence of two proteolytic fragments of CSTII in the purified sample. The addition of EDTA to the homogenization buffer slightly reduced but did not totally prevent the proteolysis.

The proteolysis fragments of CST-II were not separable by any of the chromatography methods utilized. Using analytical methods, the proteolyzed C-terminal fragment could be observed by reverse phase HPLC. CST-II is known to form an oligomeric species consistant with a tetramer in solution. Therefore, it was not surprising that size exclusion chromatography did not separate the proteolytic impurities either. Each of the CST-II elution pools (Q-SEPHAROSE™, hydroxyapatite, SP-SEPHAROSE™ HP, stored at −20° C.) were tested for residual proteolytic activity by extended incubation at 32° C. SDS PAGE analysis revealed no further proteolysis of CST-II had occurred in any of the chromatography elution pools, indicating that the protease(s) had been removed during the Q-SEPHAROSE™ chromatography step (FIG. 34)

As a result of the above data, the E. coli homogenization and clarification steps were examined as the potential source of the proteolysis. A series of experiments were devised to reduce or eliminate the proteolysis during the homogenization of the E. coli cell pellets (stored at −80° C.). Cell pellets were homogenized by microfluidation using a panel of buffers from pH 4 to pH 8.3 in the presence and absence of EDTA and a protease inhibitor cocktail (Calbiochem). The homogenized and clarified samples were purified by SEC (FIG. 35) and the fractions containing CST-II were analyzed by SDS PAGE (FIG. 36). Variations in the pH did not reduce proteolysis, however, CST-II was found to be unstable using the pH 4 conditions. Only the presence of EDTA resulted in any observable decrease in proteolysis. EDTA was therefore included in all subsequent cell disruption and clarification steps. The two main proteolysis fragments appeared to be present regardless of the method utilized to prevent proteolysis including the use of a protease cocktail. These results suggest that the proteolysis event is difficult to prevent and may occur during fermentation or harvest of the CST-II.

Analysis of Multiple CST-II HPLC Peaks. While exploring purification methods, it was observed that CST-II purified using a combination of Q-SEPHAROSE™, hydroxyapatite and SP SEPHAROSE™ HP contained three closely running bands at very similar molecular weights on an SDS-PAGE gel using non-reducing conditions. This is in contrast to a single band that was observed from the same purified CST-II on SDS PAGE gels using reducing conditions. The N-terminal amino acid sequences (Edman sequencing) of the three bands from the non-reducing SDS PAGE gel were identical to the CST-II amino terminus. In addition, three peaks were observed for the purified CST-II when analyzed by RP HPLC using non-reducing conditions. Each of the RP-HPLC peaks was isolated and re-analyzed by RP-HPLC, SDS PAGE and QToF/MS (MS: peaks 1 and 2 only). The MS analysis confirmed (within experimental variability) that the species in the two major fractions represented the intact CST-II protein. The RP-HPLC and SDS PAGE analysis data of each isolated RP-HPLC peak surprisingly showed that the three species interconverted upon storage and handling. The multibanding pattern observed for CST-II by SDS-PAGE (non-reducing conditions) and the multiple peaks observed by RP-HPLC may be due to the presence of different forms of intramolecular disulfide-bonded species of CST-II. CST-II has 6 unpaired cysteine residues that were previously shown to be in a reduced state by X-ray crystallography (C. P. Chiu, et. al. Nature Structural and Molecular Biology. 11, 163-170, February 2004). Four of these cysteine residues have intramolecular distances that may allow for intramolecular disulfide bond formation upon handling in an aerobic environment.

Purification of CST-II (Large Scale)

Cell Disruption by Microfluidization. Cell pellets from BNN93 CST-II fermentation harvests were stored at −80° C. Cell pellet (150 g) was resuspended in 50 mM Tris, 10 mM EDTA, pH 8.3 (1 g/7.5 mL buffer). Upon resuspension, the pellet was homogenized with two passes over a microfluidizer set at 16,000-18,000 PSI. The system was rinsed with an additional 2.5 mL buffer per gram pellet (375 mL) to collect any material in system due to hold up volume. The final homogenate concentration was 1 g cell pellet/10 mL buffer (1.5 L). Tween-20 was added to the homogenate (0.02% v/v) prior to clarification.

Clarification. The BNN93 cell homogenate (1:5 L) was immediately centrifuged at 500033 G for 120 minutes on a centrifuge equipped with a swinging bucket rotor (Sorval) at 4° C. The supernatant was filtered using a Cuno Zeta Plus Biocap (0.2 micron). After filtration the pH and conductivity were measured; pH=8.31, and conductivity=6.1 ms/cm. The filtered homogenate was stored at 4° C. for less than 1 hour prior to purification.

Q-SEPHAROSE™ Chromatography. An Amicon Vantage S chromatography column (12.5 cm id) was packed with Q-SEPHAROSE™ FF resin (1.5 L) and attached to an AKTA Explorer 100 LC system continuously monitoring absorbance at 280 nm. The column was equilibrated with 5 column volumes (CV) 50 mM Tris, 0.005% TWEEN®-20, pH 8.3 (Buffer A). The clarified homogenate (1.5 L) was diluted with Buffer A (4.5 L) to reduce conductivity: (after dilution: pH 8.34, 3.2 ms/cm). The diluted homogenate (6 L) was applied to the prepared column at 49 cm/hr (100 mL/min). When load was complete, unbound material was washed from the gradient of Buffer B (1 M NaCl in Buffer A): 4 CV at 15% Buffer B; 4 CV at 100% Buffer B (FIG. 37). Fractions were analyzed by SDS-PAGE and the CST-II enzyme activity determined (FIG. 38, Table 7). The purified CST-II fractions were pooled (Elution Fraction 2, FIG. 35, 600 mL) and a 0.5 mL aliquot was taken and formulated with 50% glycerol and stored at −20° C. to preserve activity. The remaining CST-II was stored at 4° C. for approximately 36 h until further purification on hydroxyapatite.

TABLE 7

CST-II Enzyme Activity Recovery after Purification on Q-SEPHAROSE ™ FF.

| Fraction Pool | Activity (U/mL) | Volume (mL) | Total Units | Step Recovery (%) |
|---|---|---|---|---|
| Homogenate | 1.72 | 1500 | 2790 | 100 |
| Q-SEPHAROSE ™ FT Fraction 1 | 0.011 | 2000 | 22 | 0.8 |
| Q-SEPHAROSE ™ FT Fraction 2 | 0.071 | 2000 | 142 | 5.1 |
| Q-SEPHAROSE ™ FT Fraction 3 | 0.124 | 2000 | 248 | 8.9 |
| Q-SEPHAROSE ™ FT Fraction 4 | 0.03 | 2000 | 60 | 2.2 |
| Q-SEPHAROSE ™ FT Fraction 5 | 0.09 | 2000 | 180 | 6.5 |
| Q-SEPHAROSE ™ FT Fraction/wash pool | 0.049 | 10000 | 490 | 17.6 |
| Q-SEPHAROSE ™ Elution Fraction 1 | 0.078 | 550 | 43 | 1.5 |
| Q-SEPHAROSE ™ Elution Fraction 2 | 4.017 | 600 | 2410 | 86.4 |
| Q-SEPHAROSE ™ Elution Fraction 3 | 0.553 | 550 | 304 | 10.9 |
| Q-SEPHAROSE ™ Elution Fraction 4 | 0.07 | 600 | 42 | 1.5 |
| Q-SEPHAROSE ™ Elution Fraction 5 | 0.087 | 600 | 52 | 1.9 |

The homogenate is prepared from 150 grains of cell pellet (15 L CST-II fermentation produced 320.7 grams cell pellet).
Step Recovery (%): calculated as total units CST-II in the individual fraction pool divided by the total units CST-II in the homogenate × 100.
Q-SEPHAROSE ™ Elution Fraction 2 was collected and prepared for subsequent purification. FT Fraction = Flow Through Fraction.

Hydroxyapatite Type II Chromatography (20 micron). An XK50 (GE Healthcare) chromatography column was packed with Hydroxyapatite Type II resin (Biorad, 20 micron) (320 mL) and attached to an AKTA Explorer 100 LC system continuously monitoring absorbance at 280 nm. The column was equilibrated with 5 CV of 5 mM sodium phosphate, 0.005% TWEEN®-20, pH 6.5. The CST-II purified by Q-SEPHAROSE™ FF (FIG. 37, Elution Fraction 2) (600 mL) was slowly added to 50 mM monobasic sodium phosphate (600 mL) while continually monitoring the pH. The pH was adjusted to 6.65 by the addition of an additional 60 mL of the 50 mM monobasic sodium phosphate. The CST-II solution (660 mL) was then further diluted with 10 mM sodium phosphate, 0.005% TWEEN®-20, pH 6.5 (Buffer A, 3.6 L) to decrease the overall sodium phosphate concentration (final volume 4.2 L). The conditioned CST-II solution was filtered (1 L Nalgene filter bottles, 0.2 micron) and the pH, conductivity and absorbance at 280 nm were measured; pH 6.54; conductivity, 4.0 ms/cm; and, A280=1.004 AU. The filtered CST-II was loaded onto the prepared column at 120 cm/hr (39.3 mL/min). Unbound material was washed from column with 5 CV Buffer A. The CST-II was eluted at 120 cm/hr (39.3 mL/min) with a gradient of Buffer B (1.5 M NaCl in Buffer A): from 0-100% Buffer B in 25 CV; followed by 5 CV of 100% Buffer B, followed by 5 CV of 500 mM sodium phosphate, pH 6.5 (FIG. 39). Fractions were sampled for SDS-PAGE and CST-II assay (FIG. 40, Table 8). The purified CST-II fractions were pooled (Elution Fraction 5, FIG. 39, 1.65 L) and a 0.5 mL aliquot was taken and formulated with 50% glycerol and stored at −20° C. to preserve activity. The remaining CST-II was stored at 4° C. for approximately 36 h until further purification on SP-SEPHAROSE™ HP.

TABLE 8

Recovery of CST-II Enzyme Activity after Hydroxyapatite Type II (20 micron) Purification.

| Fraction | Activity (U/mL) | Volume (mL) | Total Units | Step Recovery (%) |
|---|---|---|---|---|
| Q SEPHAROSE ™ Fraction 2 | 4.017 | 600 | 2410 | 100 |
| Hydroxyapatite Load | 0.477 | 4200 | 2003 | 83.1 |
| Hydroxyapatite FT/Wash pool | Below Range | 4500 | 0 | 0 |
| Hydroxyapatite Elution Fraction 1 | Below Range | 750 | 0 | 0 |
| Hydroxyapatite Elution Fraction 2 | 0.013 | 560 | 7 | 0.3 |
| Hydroxyapatite Elution Fraction 3 | 0.279 | 600 | 167 | 6.9 |
| Hydroxyapatite Elution Fraction 4 | 0.425 | 100 | 43 | 1.8 |
| Hydroxyapatite Elution Fraction 5 | 0.918 | 1650 | 1515 | 62.9 |
| Hydroxyapatite Elution Fraction 6 | 0.151 | 1150 | 174 | 7.2 |
| Hydroxyapatite Elution Fraction 7 | Below Range | 250 | 0 | 0 |

Step Recovery (%): calculated as total units CST-II in the individual fraction pool divided by the total units CST-II in the Q-SEPHAROSE ™ FF (QFF) Elution Fraction 2 × 100.
Hydroxyapatite Type II Elution Fraction 5 was collected and prepared for subsequent purification. FT = Flow Through Fraction.

SP-SEPHAROSE™ HP Chromatography. An XK50 (GE Healthcare) chromatography column was packed with SP SEPHAROSE™ HP resin (300 mL) and attached to an AKTA Explorer 100 LC system continuously monitoring absorbance at 280 nm. The column was equilibrated with 5 CV of 25 mM MES, 0.005% TWEEN®-20, pH 6.0 (Buffer A). The CST-II purified on Hydroxyapatite Type II (20 micron) (FIG. 39, Elution Fraction 5, 1.65 L, 0.005% TWEEN® 20) was adjusted to 0.02% TWEEN®-20 and dialyzed overnight against 25 mM MES, 10 mM NaCl, pH 6.0 (19 L, conductivity; 1.9 ms/cm) at 4° C. The volume of the dialyzed CST-II solution was 2.2 L and the pH and conductivity were measured (pH 6.3; conductivity, 11.3 ms/cm). The dialyzed CST-II was further diluted with Buffer A (3.8 L) and filtered (1 L Nalgene filter bottles, 0.2 micron). The pH, conductivity and absorbance (280 nm) of the filtered solution were measured (pH 6.03; conductivity, 3.9 ms/cm; A280=0.291 AU) and the solution (6 L) was loaded on the prepared column at 120 cm/hr (39.3 mL/min). Unbound material was washed from the column at the same flow rate with 5 CV of Buffer A. CST-II was eluted from the column with a gradient of Buffer B (1 M NaCl in Buffer A): 0-50% Buffer B over 15 CV, held at 15% Buffer B for 1 CV, and then any tightly bound material was eluted with 5 CV of 100% Buffer B (FIG. 41). The fractions were analyzed by SDS PAGE (FIG. 42) and the CST-II enzyme activity determined (Table 9). The purified CST-II fractions were pooled (Elution Pool 2, FIG. 41, 648 mL), a 0.5 mL aliquot was taken and formulated with 50% glycerol and stored at −20° C. to preserve activity. The remaining CSTII was stored at 4° C. for approximately 16 hours prior to final formulation.

TABLE 9

Recovery of CST-II Enzyme Activity Recovery after SP-SEPHAROSE ™ HP Chromatography.

| Fraction | Activity (U/mL) | Volume (mL) | Total Units | Step Recovery (%) |
|---|---|---|---|---|
| Hydroxyapatite Elution Fraction 5 | 0.918 | 1650 | 1515 | 100 |
| SP-SEPHAROSE ™ HP FT/Wash pool | Below Range | 6000 | 0 | 0 |
| SP-SEPHAROSE ™ HP Elution pool 2 | 1.67 | 648 | 1082 | 71.4 |
| MUSTANG ® E/Final Formulation | 0.563 | 1460 | 822 | 54.3 |

Step Recovery (%): calculated as total units CST-II in the fraction pool divided by the total units CST-II in the Hydroxyapatite (HA) Elution Fraction 5 × 100.
SP-SEPHAROSE ™ HP Elution pool 2 was collected and formulated. FT = Flow Through Fraction.

Final Formulation. The SP-SEPHAROSE™ HP pooled CST-II (Elution Pool 2, 648 mL, A280:2.19 AU) was composed of fractions that eluted between 14.7-22% Buffer B (25 mM MES, 1 M NaCl, 0.005% TWEEN® 20, pH 6.0) corresponding to an average NaCl concentration of 183.5 mM (18.35% Buffer B) (FIG. 41). The sodium chloride concentration was adjusted to 200 mM by the addition of 5 M NaCl (2.14 mL). The concentration of TWEEN®-20 was increased from 0.005% to 0.02% by the addition of 10% TWEEN®-20 (0.975 mL). A MUSTANG® E capsule filter (10 mL) was preconditioned with 25 mM MES, pH 6.0 (130 mL). The adjusted CST-II solution (650 mL) was passed through the MUSTANG® E capsule filter at a flow rate of 100 mL/min and the filtrate collected in a sterile Nalgene container (2 L). The capsule was rinsed with 25 mM MES, 200 mM NaCl, 0.02% TWEEN®-20, pH. 6.0 (approximately 100 mL) to reduce loss from filter hold up. The CST-II solution was passed over a Nalgene filtration unit (1 L, 0.2 micron) to remove a trace amount of stringy precipitate that was observed. The filtered CST-II solution (730 mL, A280=1.825 AU) was diluted (1:1) with glycerol (730 mL) in a sterile Nalene bottle (2 L) to yield CST-II in a final formulation of 12.5 mM MES, 100 mM NaCl, 0.01% TWEEN® 20, 50% glycerol, pH 6.0 (1.43 L). The sample was stored immediately at −20° C. The formulated CST-II was analyzed by SDS PAGE (FIG. 43), RP-HPLC (FIG. 44), CST-II enzyme activity (Tables 9 and 10) and endotoxin concentration.

TABLE 10

CST-II Process Summary.

| Process Step | Total Protein (mg) | Total Units | Endotoxin (EU/mg) | Purification Factor | Recovery (%) |
|---|---|---|---|---|---|
| Homogenate (150 g) | na | 2790 | 192200* | na | 100 |
| Q-SEPHAROSE ™ | 4772.7 | 2410 | 303 | na | 86.4 |
| Hydroxyapetite Type II | 1679.3 | 1515 | <49 | 1.79 | 54.3 |

TABLE 10-continued

CST-II Process Summary.

| Process Step | Total Protein (mg) | Total Units | Endotoxin (EU/mg) | Purification Factor | Recovery (%) |
|---|---|---|---|---|---|
| SP-SEPHAROSE ™ HP | 1402.3 | 1082 | 2.98 | 0.86 | 38.8 |
| Final Formulation | 1316.5 | 822 | 0.987 | 0.81 | 29.5 |

Note:
*Endotoxin is reported as EU/mL at the Harvest of the enzyme. The specific activity of the purified CST-II is 0.624 U/mg protein. Recovery (%) calculated as total CST-II activity recovered from purification step divided by total units at start of process (2790 Units) × 100.

Results of large scale CST-II purification. CST-II from 150 grams of *E. coli* BNN93 cell pellet (less than half of a single 15 L fermentation) was homogenized in the presence of EDTA and clarified in the presence of TWEEN®-20. The clarified homogenate was captured on a 1.5 L Q-SEPHAROSE™ (Fast Flow) column and eluted with a NaCl step gradient in the presence of TWEEN®-20 (FIGS. 35 and 36). The CST-II activity was recovered from the Q-SEPHAROSE™ step in 86% yield (step recovery) based on enzyme activity (Table 8). The Q-SEPHAROSE™ elution pool was diluted into sodium phosphate buffer and captured on Hydroxyapatite Type II (20 micron) resin. The CST-II was eluted in the presence of TWEEN®-20 in a greater than 75% step recovery of enzyme activity (FIGS. 39 and 38, Table 8). The Hydroxyapatite elution pool was dialyzed into MES buffer with TWEEN®-20 and purified by SR SEPHAROSE™ HP chromatography (FIGS. 41 and 42, Table 9). The CST-II was eluted with NaCl and a tight fraction pool (Elution Pool 2) was collected to a high concentration of the enzyme. A tighter fraction pool was used to maintain a high protein concentration after this step thereby eliminating the need to concentrate the CST-II prior to formulation (Elution Pool 2 vs. Elution Pool 1) (FIG. 41, Table 11). The purified CST-II was filtered to reduce endotoxin and bioburden and formulated in 50% glycerol. The overall recovery of enzyme activity for the entire process was nearly 30% (Table 10). The resulting CST-II enzyme had a specific activity of 0.624 U/mg and a purity of greater than 98% by RP-HPLC analysis (Table 12, FIGS. 43 and 44).

TABLE 11

Comparison of Two SP SEPHAROSE ™ HP Product Elution Pools.

| SP-SEPHAROSE ™ HP | Volume (mL) | A280 | Total mg |
|---|---|---|---|
| Elution Pool 1 | 1128 | 1.40 | 1560.5 |
| Elution Pool 2 | 648 | 2.19 | 1402.3 |

TABLE 12

N-terminal Amino Acid Sequence of Purified CST-II under Reducing Conditions.

| Band | \multicolumn{10}{c}{N-Terminal Amino Acid Sequence} |
|---|---|---|---|---|---|---|---|---|---|---|

| Band | 1 | 2 | 3 | 4 | 5 | 6 | 7 | 8 | 9 | 10 |
|---|---|---|---|---|---|---|---|---|---|---|
| CST-II (Major) | G | S | M | K | K | V | I | I | A | G |
| CST-II (Minor) | M | K | K | V | I | I | A | G | N | G |
| A (Major) | G | S | M | K | K | V | I | I | A | G |
| A (Minor) | M | K | K | V | I | I | A | G | N | G |
| B (Major) | G | S | M | K | K | V | I | I | A | G |
| B (Minor) | M | K | K | V | I | — | — | — | — | — |
| C (Major) | N | L | L | K | L | A | — | — | — | — |
| C (Minor) | L | A | P | N | F | K | — | — | — | — |
| C (Minor) | F | K | N | D | N | S | — | — | — | — |

Protein bands identified on the electroblot (PVDF) of an SDS-PAGE gel (FIG. 50) were excised for individual analysis as described in the Methods section. The N-terminal sequences of the two expected species of CST-II are shown. Only CST-II protein was detected.

CST-II Major; the predominant protein sequenced for purified total CST-II.

CST-II Minor; the minor CST-II sequence detected estimated to be about 10% of total purified total CST-II.

Band A: CST-II (intact), major and minor expected N-termini observed.

Band B: CST-II N-terminal fragment, major and minor expected N-termini observed.

Band C: CST-II internal fragment with ragged end starting at $N^{172}$, $L^{176}$ and $F^{180}$ (based on GSMKK species (SEQ ID NO: 30)).

CONCLUSION

An extensive panel of chromatography methods was evaluated for the purification of CST-II form plasmid pNT1 expressed in *E. coli* BNN93 cells. Four efficient purification methodologies were identified that included Q SEPHAROSE™ capture, Hydroxyapatite Type II, SP SEPHAROSE™ HP and Butyl SEPHAROSE™ . Using these chromatography methods, a scalable 3-step process (Q SEPHAROSE™ FF, Hydroxyapatite Type II and SP SEPHAROSE™ HP) was developed for the production of CST-II (FIG. 4). Dilution and dialysis steps were utilized in place of buffer exchange filtration in order to minimize the loss of CST-II. This process successfully produced 822 Units of CSTII from 150 grams of cell pellet (2786 Units of crude enzyme activity) to greater than 98% purity with a 29.5% overall yield based on enzyme activity (Table 10).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A tagged sialyltransferase protein comprising a sialyltransferase polypeptide, wherein the sialyltransferase polypeptide comprises an amino acid sequence with at least 95% amino acid sequence identity to SEQ ID NO: 4, wherein the sialyltransferase polypeptide has a methionine-glycine-serine (MGS) tag at the amino terminus, and wherein the tagged sialyltransferase protein has sialyltransferase activity.

2. The tagged sialyltransferase protein of claim 1, wherein the sialyltransferase polypeptide is truncated.

3. The tagged sialyltransferase of claim 1, wherein the sialyltransferase polypeptide is SEQ ID NO: 4.

4. The tagged sialyltransferase protein of claim 1, wherein the protein begins with a mixture of methionine, glycine or serine.

5. A tagged sialyltransferase protein comprising a sialyltransferase polypeptide, wherein the sialyltransferase polypeptide comprises an amino acid sequence with at least 95% amino acid sequence identity to SEQ ID NO:4, wherein the sialyltransferase polypeptide has a methionine-glycine-serine (MGS) tag at the amino terminus, wherein the sialyltransferase polypeptide comprises sialyltransferase motif A (SEQ ID NO: 11) and sialyltransferase motif B (SEQ ID NO: 12), and wherein the tagged sialyltransferase protein has sialyltransferase activity.

6. A method of producing a sialylated oligosaccharide product comprising:
   a) contacting an acceptor substrate comprising an oligosaccharide with the tagged sialyltransferase of claim 1, and with a donor substrate comprising a sialic acid moiety; and
   b) allowing transfer of the sialic acid moiety from the donor substrate to the acceptor substrate, thereby producing the sialylated oligosaccharide product.

7. The method of claim 6, wherein the sialylated oligosaccharide product is produced in vitro.

8. The method of claim 6, wherein the sialylated oligosaccharide product is produced in vivo.

* * * * *